US009181318B2

(12) United States Patent
Satoshi

(10) Patent No.: US 9,181,318 B2
(45) Date of Patent: Nov. 10, 2015

(54) METHOD OF SCREENING A DRUG SUCH AS INSULIN SECRETAGOGUE

(75) Inventor: Inouye Satoshi, Yokohama (JP)

(73) Assignee: JNC Corporation, Tokyo (JP)

( * ) Notice: Subject to any disclaimer, the term of this patent is extended or adjusted under 35 U.S.C. 154(b) by 337 days.

(21) Appl. No.: 12/659,604

(22) Filed: Mar. 15, 2010

(65) Prior Publication Data

US 2010/0240038 A1     Sep. 23, 2010

(30) Foreign Application Priority Data

Mar. 16, 2009  (JP) ................. 2009-063279

(51) Int. Cl.
  *C12P 21/04*   (2006.01)
  *C12Q 1/68*    (2006.01)
  *C07K 14/62*   (2006.01)
  *C12N 9/02*    (2006.01)
  *C12Q 1/66*    (2006.01)
  *G01N 33/50*   (2006.01)
  *G01N 33/74*   (2006.01)

(52) U.S. Cl.
  CPC .............. *C07K 14/62* (2013.01); *C12N 9/0069* (2013.01); *C12Q 1/66* (2013.01); *G01N 33/502* (2013.01); *G01N 33/74* (2013.01); *C07K 2319/61* (2013.01); *G01N 2333/62* (2013.01)

(58) Field of Classification Search
  None
  See application file for complete search history.

(56) References Cited

U.S. PATENT DOCUMENTS

| 6,194,176 B1 * | 2/2001 | Newgard et al. .............. 435/69.4 |
| 2008/0076156 A1 * | 3/2008 | Inouye et al. ................. 435/69.7 |

FOREIGN PATENT DOCUMENTS

| EP | 1 875 927 | 1/2008 | | |
| JP | 2008-99669 | 5/2008 | | |
| WO | WO 99/49019 | * | 9/1999 | ............... C12N 9/00 |
| WO | 00/20619 | 4/2000 | | |
| WO | 03/088916 | 10/2003 | | |
| WO | 2005/037226 | 4/2005 | | |
| WO | 2009/012359 | 1/2009 | | |
| WO | 2012/171024 | 12/2012 | | |

OTHER PUBLICATIONS

SCORE Result for SEQ ID No. 10; Mar. 2012.*
SCORE Result for SEQ ID No. 8; Mar. 2012.*
Score Report SEQ ID No. 10 Newgard et al downloaded Oct. 19, 2012.*
Score Report SEQ ID No. 8 Bryan et al downloaded Oct. 19, 2012.*
Tang Dissertation entitled Genetic Engineering of Non-Beta-Cells for Regulated Insulin Secretion (Nov. 2003).*
Tannous in Codon-Optimized Gaussia Luciferase cDNA for Mammalian Gene Expression in Culture and in Vivo (Molecular Therapy vol. 11, No. 3, Mar. 2005, pp. 435-443).*
UK Search Report dated Jul. 8, 2010 in Application No. GB1004167.1.
A. E. Pouli et al., "Insulin Targeting to the Regulated Secretory Pathway after Fusion with Green Fluorescent Protein and Firefly Luciferase", Biochem. J., vol. 331, pp. 669-675, 1998.
Ohara-Imaizumi et al., "Imaging Exocytosis of Single Insulin Secretory Granules with Evanescent Wave Microscopy", The Journal of Biological Chemistry, vol. 277, No. 6, pp. 3805-3808, Feb. 8, 2002.
Takahashi et al., "Fusion Pore Dynamics and Insulin Granule Exocytosis in the Pancreatic Islet", Science, vol. 297, pp. 1349-1352, Aug. 23, 2002.
Inouye et al., "Imaging of Luciferase Secretion from Transformed Chinese Hamster Ovary Cells", Proc. Natl. Acad. Sci., vol. 89, pp. 9584-9587, Oct. 1992.
Suzuki et al., "Real-Time Bioluminescence Imagining of a Protein Secretory Pathway in Living Mammalian Cells Using Gaussia Luciferase", FEBS Letters, vol. 581, pp. 4551-4556, 2007.
United Kingdom Office Action issued Mar. 21, 2014 in corresponding United Kingdom Application No. GB1004167.1.
Christian E. Badr et al., "A Highly Sensitive Assay for Monitoring the Secretory Pathway and ER Stress", PLos ONE, vol. 2, Issue 6, Jun. 2007, e571, pp. 1-8.
Office Action issued Mar. 18, 2014 in corresponding Japanese Application No. 2009-063279, with English translation.
Office Action issued Oct. 15, 2013 in corresponding GB Patent Application No. 1309636.7.
Takahiro Suzuki et al., "Video-Rate Bioluminescence Imaging of Matrix Metalloproteinase-2 Secreted from a Migrating Cell", PLoS One, vol. 6, Issue 9, Article No. e25243, Sep. 2011.
Li-Lun Ho et al., "Penta-$O$-galloyl-$\beta$-D-glucose inhibits the invasion of mouse melanoma by suppressing metalloproteinase-9 through down-regulation of activator protein-1", European Journal of Pharmacology, vol. 453, 2002, pp. 149-158.

* cited by examiner

*Primary Examiner* — Catherine S Hibbert
(74) *Attorney, Agent, or Firm* — Wenderoth, Lind & Ponack, L.L.P.

(57) ABSTRACT

The screening method of the present invention is useful for screening drugs such as insulin secretagogues having an insulin secretagogue activity with minimized side effects (hypoglycemia induction, etc.). The transformant in which a polynucleotide encoding the fusion protein used for the screening method is introduced, the screening kit comprising the transformant, etc. are also useful for screening excellent drugs.

5 Claims, 9 Drawing Sheets

METHOD OF SCREENING A DRUG SUCH AS INSULIN SECRETAGOGUE

FIELD OF THE INVENTION

The present invention relates to a method of screening a drug such as an insulin secretagogue. More specifically, the present invention relates to a method of screening a drug such as insulin secretagogue using the luminescence imaging method, and so on.

BACKGROUND OF THE INVENTION

Insulin is a hormone that plays an important role in regulating glucose metabolism. Insulin produced from Langerhans' islet β cells in the pancreas is secreted by exocytosis. The secreted insulin acts on cells having insulin receptors to stimulate glucose uptake into cells. Blood sugar levels in the body are maintained in the optimal range by the action of insulin.

Diabetes mellitus, which is a representative disease associated with insulin, is classified into Type I diabetes mellitus and Type II diabetes mellitus.

In Type I diabetes mellitus, the response to insulin is maintained and blood sugar levels can be controlled by the administration of insulin formulations (e.g., animal insulin preparations extracted from the bovine or swine pancreas; human insulin preparations synthesized by a genetic engineering technique using *Escherichia coli* or a yeast), or by the administration of insulin secretagogues (for example, sulfonylureas (e.g., tolbutamide, glibenclamide, gliclazide, chlorpropamide, tolazamide, acetohexamide, glyclopyramide, glimepiride, glipizide, glybuzole, etc.), repaglinide, senaglinide, nateglinide, mitiglinide, etc.).

The insulin preparations are classified as rapid-acting, regular-acting, intermediate-acting, long-acting, mixed (rapid-acting+intermediate-acting, regular-acting+intermediate-acting), long-acting soluble preparations, and the like, based on time of action. These insulin preparations are appropriately administered depending on the symptoms and conditions of the patient.

As described above, a variety of drugs are known as insulin secretagogues but these drugs involve problems that preprandial hypoglycemia, postprandial hyperglycemia, etc. tend to occur.

Extracellular release (secretion) of a secretory protein is mediated by a mechanism that trafficking vesicles fuse with cell membranes (exocytosis). The total internal reflection fluorescence method (TIRF method) and the fluorescence imaging method (two-photon molecular excitation method) using the excitation of two photons are known as techniques for the visualization of exocytosis.

It has been reported that secretion of the fused protein of enhanced GFP, which is one of fluorescent proteins, with insulin (insulin-EGFP) was observed by the total internal reflection fluorescence method (J. Biol. Chem. 277, 3805-3808 (2002)). More specifically, the phenomenon of exocytosis with the trafficking vesicles containing insulin-EGFP fusion protein was observed from the adhesive part of cells on the side of a glass-bottom dish.

It has been reported that fluorescent dyes were permeated into the spaces where cells are closely adhered to each other, and the secretory vesicles containing insulin fused the cell membranes to form the omega-type structure was observed by the two-photon molecular excitation method (Science, 297, 1349-1352 (2002)).

However, both the total internal reflection fluorescence method and the two-photon molecular excitation method have problems that localization of the exocytotic sites on the whole cells cannot be identified and the secreted proteins cannot be quantified, etc.

It has been reported that the exocytotic secretion of luciferase was observed by the bioluminescence imaging method, using Vargula luciferase (Proc. Natl. Acad. Sci., USA, 89, 9584-9587 (1992)).

It has been reported that the process for the secretion of the fused protein (DBHsp-GLase) of the signal peptide sequence (DBHsp) of human DBH (dopamine β-hydroxylase) with *Gaussia* luciferase (GLase) was observed by the bioluminescence imaging method, (FEBS Letters, 581, 4551-4556 (2007)).

However, no report is known of observation of the exocytotic secretion of functional proteins and functional polypeptides such as hormones, growth factors, etc., by the bioluminescence imaging method.

Matrix metalloproteinase (MMP) is a superfamily of zinc-dependent endopeptidases and involved in the degradation of the major components of extracellular matrix and connective tissues that inhibit motility of cells.

MMP, especially a gelatinase is known to be associated with metastasis and diffusion of cancers. For example, MMP-2 and MMP-9, which are gelatinases, are known to rise in a particular tumor promoting event. MMP-2 and MMP-9 degrade type IV collagen as the main components of the basal membrane and denatured collagen (gelatin) to induce tumor metastasis. It is also known that disruption of vascular membranes mainly composed of type IV collagen plays an important role in tumor metastasis.

SUMMARY OF THE INVENTION

Under the foregoing circumstances, it has been desired to develop a method of drug screening such as screening of insulin secretagogues having a more potent insulin secretagogue activity with minimized side effects (hypoglycemia induction, etc.) or the like.

It has also been desired to provide a method of drug screening such as screening of more effective tumor metastasis inhibitors (MMP-2 inhibitors, etc.) or the like.

As a result of extensive investigations to solve the problems above, the present inventors have found that by using cells transformed by polynucleotides encoding the fusion proteins of preproinsulins and luciferases, insulin secretion from the cells can be observed by the bioluminescence imaging method thereby to determine localization of the exocytotic sites over the entire cells, quantify the amount of insulin secreted from the cells, and so on.

It has also been found that by using cells transformed by polynucleotides encoding the fusion proteins of pro-MMP-2 and luciferases, secretion of MMP-2 from the cells can be observed by the bioluminescence imaging method thereby to quantify the amount of MMP-2 secreted from the cells, assess diffusion kinetics outside the cells, and so on.

Based on these findings, the inventors have continued further investigations and come to accomplish the present invention.

That is, the present invention provides the following features, and so on.

(1) A method of screening a substance regulating insulin secretion from a cell, which comprises using a cell transformed by a polynucleotide encoding a fusion protein of preproinsulin and a luciferase.

(2) The screening method according to (1) above, wherein the luciferase is a secretory luciferase.

(3) The screening method according to (2) above, wherein the secretory luciferase is *Gaussia* luciferase.

(4) The screening method according to (3) above, wherein *Gaussia* luciferase is a protein of any one of (a) through (d) below:
 (a) a protein comprising the amino acid sequence of SEQ ID NO: 8;
 (b) a protein consisting of an amino acid sequence in which at least one amino acid residue is deleted, substituted, inserted and/or added in the amino acid sequence of SEQ ID NO: 8, and having a luciferase activity;
 (c) a protein consisting of an amino acid sequence having at least 90% identity to the amino acid sequence of SEQ ID NO: 8, and having a luciferase activity; and,
 (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having a luciferase activity.

(5) The screening method according to (4) above, wherein *Gaussia* luciferase is a protein of any one of (a) through (d) below:
 (a) a protein consisting of the amino acid sequence of SEQ ID NO: 8;
 (b) a protein consisting of an amino acid sequence comprising deletion, substitution, insertion and/or addition of one to several amino acid residues in the amino acid sequence of SEQ ID NO: 8, and having a luciferase activity;
 (c) a protein consisting of an amino acid sequence having at least 90% identity to the amino acid sequence of SEQ ID NO: 8, and having a luciferase activity; and,
 (d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having a luciferase activity.

(6) The screening method according to any one of (1) to (5) above, wherein preproinsulin is a polypeptide of any one of (e) through (h) below:
 (e) a polypeptide consisting of the amino acid sequence of SEQ ID NO: 10;
 (f) a polypeptide comprising a polypeptide consisting of an amino acid sequence comprising deletion, substitution, insertion and/or addition of one to several amino acid residues in the amino acid sequence of SEQ ID NO: 10, and having an insulin activity;
 (g) a polypeptide comprising a polypeptide consisting of an amino acid sequence having at least 90% identity to the amino acid sequence of SEQ ID NO: 10, and having an insulin activity; and,
 (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 9, and having an insulin activity.

(7) The screening method according to (6) above, wherein preproinsulin consists of a signal peptide of preproinsulin and the polypeptide of any one of (i) through (l) below:
 (i) a polypeptide consisting of the amino acid sequence of SEQ ID NO: 4;
 (j) a polypeptide comprising a polypeptide consisting of an amino acid sequence comprising deletion, substitution, insertion and/or addition of one to several amino acid residues in the amino acid sequence of SEQ ID NO: 4, and having an insulin activity;
 (k) a polypeptide comprising a polypeptide consisting of an amino acid sequence having at least 90% identity to the amino acid sequence of SEQ ID NO: 4, and having an insulin activity; and,
 (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having an insulin activity.

(8) The screening method according to (7) above, wherein the signal peptide of preproinsulin is a polypeptide consisting of the amino acid sequence of SEQ ID NO: 6.

(9) The screening method according to (1) through (8) above, wherein the fusion protein is a polypeptide of any one of (m) through (p) below:
 (m) a polypeptide consisting of the amino acid sequence of SEQ ID NO: 12;
 (n) a polypeptide comprising a polypeptide consisting of an amino acid sequence comprising deletion, substitution, insertion and/or addition of one to several amino acid residues in the amino acid sequence of SEQ ID NO: 12, and having an insulin activity;
 (o) a polypeptide comprising a polypeptide consisting of an amino acid sequence having at least 90% identity to the amino acid sequence of SEQ ID NO: 12, and having an insulin activity; and,
 (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11, and having an insulin activity.

(10) The screening method according to (1) through (9) above, which further comprises the step of detecting luminescence using a CCD camera or a photon counting camera.

(11) A polynucleotide encoding a fusion protein of preproinsulin and a luciferase.

(12) The polynucleotide according to (11) above, wherein the luciferase is a secretory luciferase.

(13) The polynucleotide according to (12) above, wherein the secretory luciferase is *Gaussia* luciferase.

(14) The polynucleotide according to (13) above, wherein *Gaussia* luciferase is a protein of any one of (a) through (d) below:
 (a) a protein comprising the amino acid sequence of SEQ ID NO: 8;
 (b) a protein consisting of an amino acid sequence in which at least one amino acid residue is deleted, substituted, inserted and/or added in the amino acid sequence of SEQ ID NO: 8, and having a luciferase activity;
 (c) a protein consisting of an amino acid sequence having at least 90% identity to the amino acid sequence of SEQ ID NO: 8, and having a luciferase activity; and,
 (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having a luciferase activity.

(15) The polynucleotide according to (14) above, wherein *Gaussia* luciferase is a protein according to any one of (a) through (d) below:
 (a) a protein consisting of the amino acid sequence of SEQ ID NO: 8;

(b) a protein consisting of an amino acid sequence comprising deletion, substitution, insertion and/or addition of one to several amino acid residues in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having a luciferase activity.

(16) The polynucleotide according to any one of (1) through (15) above, wherein preproinsulin is a polypeptide according to any one of (e) through (h) below:

(e) a polypeptide consisting of the amino acid sequence of SEQ ID NO: 10;

(f) a polypeptide comprising a polypeptide consisting of an amino acid sequence comprising deletion, substitution, insertion and/or addition of one to several amino acid residues in the amino acid sequence of SEQ ID NO: 10, and having an insulin activity;

(g) a polypeptide comprising a polypeptide consisting of an amino acid sequence having at least 90% identity to the amino acid sequence of SEQ ID NO: 10, and having an insulin activity; and, (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 9, and having an insulin activity.

(17) The polynucleotide according to (16) above, wherein preproinsulin consists of a signal peptide of preproinsulin and the polypeptide according to any one of (i) through (l) below:

(i) a polypeptide consisting of the amino acid sequence of SEQ ID NO: 4;

(j) a polypeptide comprising a polypeptide consisting of an amino acid sequence comprising deletion, substitution, insertion and/or addition of one to several amino acid residues in the amino acid sequence of SEQ ID NO: 4, and having an insulin activity;

(k) a polypeptide comprising a polypeptide consisting of an amino acid sequence having at least 90% identity to the amino acid sequence of SEQ ID NO: 4, and having an insulin activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having an insulin activity.

(18) The polynucleotide according to (17) above, wherein the signal peptide of preproinsulin is a polypeptide consisting of the amino acid sequence of SEQ ID NO: 6.

(19) The polynucleotide according to any one of (11) through (18) above, wherein the fusion protein is a polypeptide according to any one of (m) through (p) below:

(m) a polypeptide consisting of the amino acid sequence of SEQ ID NO: 12;

(n) a polypeptide comprising a polypeptide consisting of an amino acid sequence comprising deletion, substitution, insertion and/or addition of one to several amino acid residues in the amino acid sequence of SEQ ID NO: 12, and having an insulin activity;

(o) a polypeptide comprising a polypeptide consisting of an amino acid sequence having at least 90% identity to the amino acid sequence of SEQ ID NO: 12, and having an insulin activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11, and having an insulin activity.

(20) A recombinant vector comprising the polynucleotide according to any one of (11) through (19) above.

(21) A transformant wherein the recombinant vector according to (20) above is introduced.

(22) The transformant according to (21) above, which is derived from a cell line.

(23) The transformant according to (22) above, which is derived from a mammal.

(24) The transformant according to any one of (21) to (23) above, which is derived from a pancreatic β cell.

(25) A method of observing the extracellular secretion of insulin, which comprises using the transformant according to any one of (21) to (24) above.

(26) A method of identifying the localization of exocytotic site of insulin in a cell, which comprises using the transformant according to any one of (21) to (24) above.

(27) A method of quantifying insulin secreted extracellularly, which comprises using the transformant according to any one of (21) to (24) above.

(28) A method of determining the frequency of insulin secretion, which comprises using the transformant according to any one of (21) to (24) above.

(29) A method of observing the diffusion dynamics of insulin secreted extracellularly, which comprises using the transformant according to any one of (21) to (24) above.

(30) A kit comprising the transformant according to any one of (21) to (24) above.

(31) The kit according to (30) above, which is a kit used for screening a drug.

(32) The kit according to (30) or (31) above, further comprising a luciferin.

(33) A fusion protein of preproinsulin and a luciferase.

(34) The protein according to (33) above, wherein the luciferase is a secretory luciferase.

(35) The protein according to (34) above, wherein the secretory luciferase is *Gaussia* luciferase.

(36) The protein according to (35) above, wherein *Gaussia* luciferase is a protein according to any one of (a) through (d) below.

(a) a protein comprising the amino acid sequence of SEQ ID NO: 8;

(b) a protein consisting of an amino acid sequence in which at least one amino acid residue is deleted, substituted, inserted and/or added in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having a luciferase activity.

(37) The protein according to (36) above, wherein *Gaussia* luciferase is a protein according to any one of (a) through (d) below.

(a) a protein consisting of the amino acid sequence of SEQ ID NO: 8;

(b) a protein consisting of an amino acid sequence comprising deletion, substitution, insertion and/or addition of one to several amino acid residues in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having a luciferase activity.

(38) The protein according to any one of (33) through (37) above, wherein preproinsulin is a polypeptide according to any one of (e) through (h) below.

(e) a polypeptide consisting of the amino acid sequence of SEQ ID NO: 10;

(f) a polypeptide comprising a polypeptide consisting of an amino acid sequence comprising deletion, substitution, insertion and/or addition of one to several amino acid residues in the amino acid sequence of SEQ ID NO: 10, and having an insulin activity;

(g) a polypeptide comprising a polypeptide consisting of an amino acid sequence having at least 90% identity to the amino acid sequence of SEQ ID NO: 10, and having an insulin activity; and, (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 9, and having an insulin activity.

(39) The protein according to (38) above, wherein preproinsulin consists of a signal peptide of preproinsulin and the polypeptide according to any one of (i) through (l) below:

(i) a polypeptide consisting of the amino acid sequence of SEQ ID NO: 4;

(j) a polypeptide comprising a polypeptide consisting of an amino acid sequence comprising deletion, substitution, insertion and/or addition of one to several amino acid residues in the amino acid sequence of SEQ ID NO: 4, and having an insulin activity;

(k) a polypeptide comprising a polypeptide consisting of an amino acid sequence having at least 90% identity to the amino acid sequence of SEQ ID NO: 4, and having an insulin activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having an insulin activity.

(40) The protein according to (39) above, wherein the signal peptide of preproinsulin is a polypeptide consisting of the amino acid sequence of SEQ ID NO: 6.

(41) The protein according to any one of (33) through (40) above, comprising the polypeptide according to any one of (m) through (p) below:

(m) a polypeptide consisting of the amino acid sequence of SEQ ID NO: 12;

(n) a polypeptide comprising a polypeptide consisting of an amino acid sequence comprising deletion, substitution, insertion and/or addition of one to several amino acid residues in the amino acid sequence of SEQ ID NO: 12, and having an insulin activity;

(o) a polypeptide comprising a polypeptide consisting of an amino acid sequence having at least 90% identity to the amino acid sequence of SEQ ID NO: 12, and having an insulin activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11, and having an insulin activity.

The present invention further provides the following features, and so on.

(1B) A method of screening a drug such as a substance inhibiting the secretion and/or activity of MMP-2, a cancer metastasis inhibitor, etc., which comprises using a cell transformed by a polynucleotide encoding a fusion protein of pro-MMP-2 and a luciferase.

(2B) The screening method according to (1B) above, wherein the luciferase is a secretory luciferase.

(3B) The screening method according to (2B) above, wherein the secretory luciferase is *Gaussia* luciferase.

(4B) The screening method according to (3B) above, wherein *Gaussia* luciferase is a protein of any one of (a) through (d) below:

(a) a protein comprising the amino acid sequence of SEQ ID NO: 8;

(b) a protein consisting of an amino acid sequence in which at least one amino acid residue is deleted, substituted, inserted and/or added in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having a luciferase activity.

(5B) The screening method according to (4B) above, wherein *Gaussia* luciferase is a protein of any one of (a) through (d) below:

(a) a protein consisting of the amino acid sequence of SEQ ID NO: 8;

(b) a protein consisting of an amino acid sequence comprising deletion, substitution, insertion and/or addition of one to several amino acid residues in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having a luciferase activity.

(6B) The screening method according to any one of (1B) to (5B) above, wherein pro-MMP-2 is a polypeptide of any one of (e) through (h) below:

(e) a polypeptide consisting of the amino acid sequence of SEQ ID NO: 18;

(f) a polypeptide comprising a polypeptide consisting of an amino acid sequence comprising deletion, substitution, insertion and/or addition of one to several amino acid residues in the amino acid sequence of SEQ ID NO: 18, and having a MMP-2 activity;

(g) a polypeptide comprising a polypeptide consisting of an amino acid sequence having at least 90% identity to the amino acid sequence of SEQ ID NO: 18, and having a MMP-2 activity; and, (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 17, and having a MMP-2 activity.

(7B) The screening method according to (6B) above, wherein pro-MMP-2 consists of a signal peptide of pro-MMP-2 and the polypeptide of any one of (i) through (l) below:

(i) a polypeptide consisting of the amino acid sequence of SEQ ID NO: 14;

(j) a polypeptide comprising a polypeptide consisting of an amino acid sequence comprising deletion, substitution, insertion and/or addition of one to several amino acid residues in the amino acid sequence of SEQ ID NO: 14, and having an insulin activity;

(k) a polypeptide comprising a polypeptide consisting of an amino acid sequence having at least 90% identity to the amino acid sequence of SEQ ID NO: 14, and having an insulin activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 13, and having an insulin activity.

(8B) The screening method according to (7B) above, wherein the signal peptide of pro-MMP-2 is a polypeptide consisting of the amino acid sequence of SEQ ID NO: 16.

(9B) The screening method according to (1B) through (8B) above, wherein the fusion protein is a polypeptide of any one of (m) through (p) below:

(m) a polypeptide consisting of the amino acid sequence of SEQ ID NO: 20;

(n) a polypeptide comprising a polypeptide consisting of an amino acid sequence comprising deletion, substitution, insertion and/or addition of one to several amino acid residues in the amino acid sequence of SEQ ID NO: 20, and having an insulin activity;

(o) a polypeptide comprising a polypeptide consisting of an amino acid sequence having at least 90% identity to the amino acid sequence of SEQ ID NO: 20, and having an insulin activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 19, and having an insulin activity.

(10B) The screening method according to (1B) through (9B) above, which further comprises the step of detecting luminescence using a CCD camera or a photon counting camera.

(11B) A polynucleotide encoding a fusion protein of pro-MMP-2 and a luciferase.

(12B) The polynucleotide according to (11B) above, wherein the luciferase is a secretory luciferase.

(13B) The polynucleotide according to (12B) above, wherein the secretory luciferase is *Gaussia* luciferase.

(14B) The polynucleotide according to (13B) above, wherein *Gaussia* luciferase is a protein of any one of (a) through (d) below:

(a) a protein comprising the amino acid sequence of SEQ ID NO: 8;

(b) a protein consisting of an amino acid sequence in which at least one amino acid residue is deleted, substituted, inserted and/or added in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having a luciferase activity.

(15B) The polynucleotide according to (14B) above, wherein *Gaussia* luciferase is a protein according to any one of (a) through (d) below:

(a) a protein consisting of the amino acid sequence of SEQ ID NO: 8;

(b) a protein consisting of an amino acid sequence comprising deletion, substitution, insertion and/or addition of one to several amino acid residues in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having a luciferase activity.

(16B) The polynucleotide according to any one of (1B) through (15B) above, wherein pro-MMP-2 is a polypeptide according to any one of (e) through (h) below:

(e) a polypeptide consisting of the amino acid sequence of SEQ ID NO: 18;

(f) a polypeptide comprising a polypeptide consisting of an amino acid sequence comprising deletion, substitution, insertion and/or addition of one to several amino acid residues in the amino acid sequence of SEQ ID NO: 18, and having an insulin activity;

(g) a polypeptide comprising a polypeptide consisting of an amino acid sequence having at least 90% identity to the amino acid sequence of SEQ ID NO: 18, and having an insulin activity; and, (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 17, and having an insulin activity.

(17B) The polynucleotide according to (16B) above, wherein pro-MMP-2 consists of a signal peptide of pro-MMP-2 and the polypeptide according to any one of (i) through (l) below:

(i) a polypeptide consisting of the amino acid sequence of SEQ ID NO: 14;

(j) a polypeptide comprising a polypeptide consisting of an amino acid sequence comprising deletion, substitution, insertion and/or addition of one to several amino acid residues in the amino acid sequence of SEQ ID NO: 14, and having an insulin activity;

(k) a polypeptide comprising a polypeptide consisting of an amino acid sequence having at least 90% identity to the amino acid sequence of SEQ ID NO: 14, and having an insulin activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 13, and having an insulin activity.

(18B) The polynucleotide according to (17B) above, wherein the signal peptide of pro-MMP-2 is a polypeptide consisting of the amino acid sequence of SEQ ID NO: 16.

(19B) The polynucleotide according to any one of (11B) through (17B) above, wherein the fusion protein is a polypeptide according to any one of (m) through (p) below:

(m) a polypeptide consisting of the amino acid sequence of SEQ ID NO: 20;

(n) a polypeptide comprising a polypeptide consisting of an amino acid sequence comprising deletion, substitution, insertion and/or addition of one to several amino acid residues in the amino acid sequence of SEQ ID NO: 20, and having an insulin activity;

(o) a polypeptide comprising a polypeptide consisting of an amino acid sequence having at least 90% identity to the amino acid sequence of SEQ ID NO: 20, and having an insulin activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 19, and having an insulin activity.

(20B) A recombinant vector comprising the polynucleotide according to any one of (11B) through (19B) above.

(21B) A transformant wherein the recombinant vector according to (20B) above is introduced.

(22B) The transformant according to (21B) above, which is derived from a cell line.

(23B) The transformant according to (22B) above, which is derived from a mammal.

(24B) The transformant according to any one of (21B) to (23B) above, which is derived from a cancer cell.

(25B) A method of observing the extracellular secretion of MMP-2, which comprises using the transformant according to any one of (21B) to (24B) above.

(26B) A method of identifying the localization of exocytotic site of MMP-2 in a cell, which comprises using the transformant according to any one of (21B) to (24B) above.

(27B) A method of quantifying MMP-2 secreted extracellularly, which comprises using the transformant according to any one of (21B) to (24B) above.

(28B) A method of determining the frequency of insulin secretion, which comprises using the transformant according to any one of (21B) to (24B) above.

(29B) A method of observing the diffusion dynamics of MAP-2 secreted extracellularly, which comprises using the transformant according to any one of (21B) to (24B) above.

(30B) A kit comprising the transformant according to any one of (21B) to (24B) above.

(31B) The kit according to (30B) above, which is a kit used for screening a drug.

(32B) The kit according to (30B) or (31B) above, further comprising a luciferin.

(33B) A fusion protein of pro-MMP-2 and a luciferase.

(34B) The protein according to (33B) above, wherein the luciferase is a secretory luciferase.

(35B) The protein according to (34B) above, wherein the secretory luciferase is *Gaussia* luciferase.

(36B) The protein according to (35B) above, wherein *Gaussia* luciferase is a protein according to any one of (a) through (d) below.

(a) a protein comprising the amino acid sequence of SEQ ID NO: 8;

(b) a protein consisting of an amino acid sequence in which at least one amino acid residue is deleted, substituted, inserted and/or added in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having a luciferase activity.

(37B) The protein according to (36B) above, wherein *Gaussia* luciferase is a protein according to any one of (a) through (d) below.

(a) a protein consisting of the amino acid sequence of SEQ ID NO: 8;

(b) a protein consisting of an amino acid sequence comprising deletion, substitution, insertion and/or addition of one to several amino acid residues in the amino acid sequence of SEQ ID NO: 8, and having a luciferase activity;

(c) a protein consisting of an amino acid sequence having at least 90% identity to the amino acid sequence of SEQ ID NO: 8, and having a luciferase activity; and, (d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having a luciferase activity.

(38B) The protein according to any one of (33B) through (37B) above, wherein pro-MMP-2 is a polypeptide according to any one of (e) through (h) below.

(e) a polypeptide consisting of the amino acid sequence of SEQ ID NO: 18;

(f) a polypeptide comprising a polypeptide consisting of an amino acid sequence comprising deletion, substitution, insertion and/or addition of one to several amino acid residues in the amino acid sequence of SEQ ID NO: 18, and having a MMP-2 activity;

(g) a polypeptide comprising a polypeptide consisting of an amino acid sequence having at least 90% identity to the amino acid sequence of SEQ ID NO: 18, and having a MMP-2 activity; and, (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 18, and having a MMP-2 activity.

(39B) The protein according to (38B) above, wherein pro-MMP-2 consists of a signal peptide of pro-MMP-2 and the polypeptide according to any one of (i) through (l) below:

(i) a polypeptide consisting of the amino acid sequence of SEQ ID NO: 14;

(j) a polypeptide comprising a polypeptide consisting of an amino acid sequence comprising deletion, substitution, insertion and/or addition of one to several amino acid residues in the amino acid sequence of SEQ ID NO: 14, and having a MMP-2 activity;

(k) a polypeptide comprising a polypeptide consisting of an amino acid sequence having at least 90% identity to the amino acid sequence of SEQ ID NO: 14, and having a MMP-2 activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 13, and having a MMP-2 activity.

(40B) The protein according to (39B) above, wherein the signal peptide of pro-MMP-2 is a polypeptide consisting of the amino acid sequence of SEQ ID NO: 16.

(41B) The protein according to any one of (33B) through (40B) above, comprising the polypeptide according to any one of (m) through (p) below:

(m) a polypeptide consisting of the amino acid sequence of SEQ ID NO: 20;

(n) a polypeptide comprising a polypeptide consisting of an amino acid sequence comprising deletion, substitution, insertion and/or addition of one to several amino acid residues in the amino acid sequence of SEQ ID NO: 20, and having a MMP-2 activity;

(o) a polypeptide comprising a polypeptide consisting of an amino acid sequence having at least 90% identity to the amino acid sequence of SEQ ID NO: 20, and having a MMP-2 activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 19, and having a MMP-2 activity.

According to the present invention, the method of drug screening such as screening of insulin secretagogues having a more potent insulin secretagogue activity with minimized side effects (hypoglycemia induction, etc.), etc. can be provided. Furthermore, the transformants in which the polynucleotide encoding the fusion protein used in the screening method is introduced, the screening kit comprising the transformants, etc. can be provided.

DETAILED DESCRIPTION OF THE INVENTION

Figure 1:
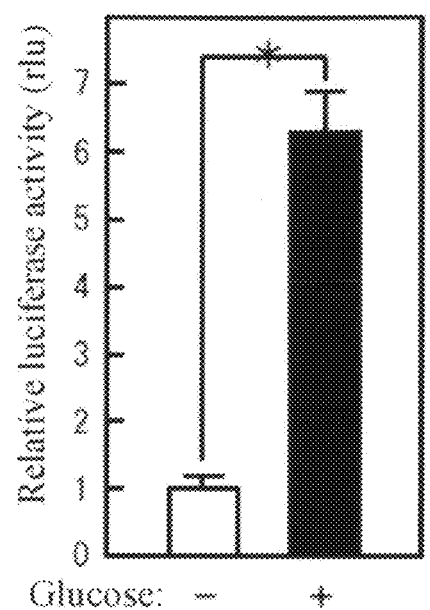
FIG. 1 shows the comparison of activities of the insulin-GLase fusion protein secreted outside cells by the addition or without addition (−, +) to the transformant derived from the MIN6 cell line obtained in EXAMPLE 1-2.

1. Drug Screening Method of the Invention

The drug screening method of the invention is directed to a method of drug screening including screening of a substance that promotes (or regulates) insulin secretion from cells, a substance that inhibits the secretion and/or activity of MMP-2, a cancer metastasis inhibitor, etc., using the cells transformed by the fusion protein of a secretory protein such as preproinsulin or MMP-2 and a luciferase.

More specifically, the drug screening method of the present invention is directed to a method of screening a substance that promotes (or regulates) insulin secretion from cells, which comprises observing the insulin secretion from cells by the bioluminescence imaging method, and comparing the insulin levels secreted in the cases where a test compound is added or not added, using the cell transformed by the polynucleotide encoding the fusion protein of, e.g., preproinsulin and the luciferase.

The drug screening method of the invention is also directed to a method of drug screening including screening of a substance that inhibits the secretion and/or activity of MMP-2, a cancer metastasis inhibitor, etc., by comparing the secretion of MMP-2, etc., which comprises comparing the secretion of MMP-2, etc. in the cases where a test compound is added or not added, using the cell transformed by the polynucleotide encoding the fusion protein of, e.g., pro-MMP-2 and the luciferase.

Hereinafter, the present invention is described in detail with reference to the embodiments.

The drug screening method of the invention includes, for example, Screening method 1, Screening method 2, and so on.

Screening Method 1:

The method of screening a substance that regulates insulin secretion from cells, which comprises Steps (a) through (d) below:

Step (a): the step of culturing a cell transformed by the polynucleotide encoding the fusion protein of preproinsulin and the luciferase in a medium in the presence or absence of a test compound;

Step (b): the step of expressing the fusion protein of the present invention to secrete the fusion protein of the invention into a luciferin-containing medium (outside the cells).

Step (c): the step of observing the fusion protein secreted extracellularly by luminescence imaging; and, Step (d): the step of comparing the expression of the fusion protein in the presence of or in the absence of a test compound.

These steps are explained below in detail.

Step (a)

(1) Luciferase

The luciferase used in the present invention refers to an enzyme which catalyzes the reaction that luciferin as a luminescence substrate is oxidized in the presence of oxygen to form oxyluciferin. This oxidization reaction by the oxygen of luciferin which is catalyzed by a luciferase is called a luciferin-luciferase reaction. The oxyluciferin formed by the luciferin-luciferase reaction is formed in an excited state, and emission of light occurs during a transition to the ground state.

The luciferase used in the present invention is preferably a secretory luciferase, more preferably, a coelenterazine-type luciferase, and particularly preferably *Gaussia* luciferase. Examples of the coelenterazine-type luciferase include *Gaussia* luciferase, *Renilla* (*Renilla reniformis*) luciferase, *Pleuromamma* luciferase, *Metridia* luciferase, *Oplophorus* (*Oplophorus grachlorostris*) luciferase, and the like.

The secretory luciferase refers to a luciferase having a secretory signal peptide, which can be secreted extracellularly.

As used herein, where the luciferase is a secretory luciferase, the luciferase may have a signal peptide or may lack a signal peptide.

*Gaussia* luciferase means a luciferase derived from *Gaussia princeps*. As used herein, *Gaussia* luciferase may have a signal peptide or may lack a signal peptide. In other words, *Gaussia* luciferase lacking a signal peptide is included in *Gaussia* luciferase.

*Gaussia* luciferase used in the present invention includes a protein consisting of the amino acid sequence of SEQ ID NO: 2, a protein consisting of the amino acid sequence of SEQ ID NO: 8, a protein having substantially the same activity or function as the protein consisting of the amino acid sequence of SEQ ID NO: 2, and a protein having substantially the same activity or function as the protein consisting of the amino acid sequence of SEQ ID NO: 8.

The term "substantially the same activity or function" is used to mean that, for example:

(i) the protein described above functions to effect the luciferin-luciferase reaction with luciferin as a luminescence substrate;

(ii) the maximum luminescence intensity (Imax) of the luminescence caused by the luciferin-luciferase reaction with the protein above is ¼ or more, preferably ⅓ or more, more preferably ½ or more and most preferably 1/1.5 or more, than the maximum luminescence intensity of the luminescence caused by the luciferin-luciferase reaction with the amino acid sequence of SEQ ID NO: 8;

(iii) the half-life period of the luminescence caused by the luciferin-luciferase reaction with the protein above is 4 times or less, preferably 3 times or less, more preferably 2 times or less and most preferably 1.5 times or less, than the half-life period of the luminescence caused by the luciferin-luciferase reaction with the amino acid sequence of SEQ ID NO: 8; and so on. The substantially the same activity or function is sometimes also referred to as the "luciferase activity." The luminescence activity or luminescence pattern described above may be measured by the methods described in, e.g., Methods in Enzymology 326, 165-174 (2000), etc. Specifically, luciferin is added to the protein above in the presence of oxygen to initiate the luminescence reaction, and the luminescence activity or luminescence pattern may be measured using a luminescence measurement device, for example, TD-4000 (manufactured by Labo Science), Berthold 960 (manufactured by Berthold, Inc.), etc.

More specifically, the *Gaussia* luciferase used in the present invention includes (a) a protein comprising the amino acid sequence of SEQ ID NO: 8; (b) a protein consisting of an amino acid sequence in which at least one amino acid residue is deleted, substituted, inserted and/or added in the amino acid sequence of SEQ ID NO: 8, and having the luciferase activity; (c) a protein consisting of an amino acid sequence having at least 90% identity to the amino acid sequence of SEQ ID NO: 8, and having the luciferase activity; (d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having the luciferase activity; (a') a protein consisting of the amino acid sequence of SEQ ID NO: 2; (b') a protein consisting of an amino acid sequence in which at least one amino acid residue is deleted, substituted, inserted and/or added in the amino acid sequence of SEQ ID NO: 2, and having the luciferase activity; (c') a protein consisting of an amino acid sequence having at least 90% identity to the amino acid sequence of SEQ ID NO: 8, and having the luciferase activity; and, (d') a protein consisting of an amino acid sequence encoded by a polynucleotide that hybridizes under stringent conditions to a polynucleotide consisting of a nucleotide sequence complementary to the nucleotide sequence of SEQ ID NO: 7, and having the luciferase activity; and the like.

The term "hybridizes under stringent conditions" will be described later.

As used herein, the range of "at least one" in the "amino acid sequence in which at least one amino acid residue is deleted, substituted, inserted and/or added" includes, for example, 1 to 17, 1 to 10, 1 to 9, 1 to 8, 1 to 7, 1 to 6 (1 to several), 1 to 5, 1 to 4, 1 to 3, 1 or 2, and 1. A smaller number of the amino acids deleted, substituted, inserted and/or added is more preferable in general. Two or more types of modifications from the above deletions, substitutions, insertions and additions in amino acid residues may occur concurrently. Such proteins may be obtained by using the site-specific mutagenesis described in, for example, MOLECULAR CLONING, 3rd. edition; Current Protocols in Molecular Biology; Nuc. Acids. Res., 10, 6487 (1982); Proc. Natl. Acad. Sci. USA, 79, 6409 (1982); Gene 34, 315 (1985); Nuc. Acids. Res., 13, 4431 (1985); or Proc. Natl. Acad. Sci. USA, 82, 488 (1985), etc.

(2) Luciferin

The luciferin used in the present invention refers to a substance which is oxidized to oxyluciferin in the presence of oxygen by the catalytic action of a luciferase. This oxidization reaction by the oxygen of luciferin which is catalyzed by a luciferase is called a luciferin-luciferase reaction. The oxyluciferin formed by the luciferin-luciferase reaction is formed in an excited state, and emission of light occurs during a transition to the ground state. That is, luciferin is a luminescent substrate for the luciferin-luciferase reaction.

The luciferin used in the present invention has a substrate specificity to the luciferin-luciferase reaction and is appropriately chosen depending on the luciferase used. For example, where *Gaussia* luciferase used as the luciferin, coelenterazine (CTZ) is employed. Coelenterazine is used also where other coelenterazine-type luciferases (e.g., *Renilla* luciferase, *Pleuromamma* luciferase, *Metridia* luciferase, *Oplophorus* luciferase, etc.).

(3) Preproinsulin, Proinsulin and Insulin

Insulin is a peptide hormone composed of an A chain consisting of 21 amino acid residues and a B chain consisting of 30 amino acid residues, and plays an important role in the regulation of glucose metabolism. Insulin is formed by enzymatic cleavage of proinsulin as a precursor composed of 86 amino acid residues at the two basic dipeptide portions to produce its A and B chains and then a disulfide bond formation between the two portions. Proinsulin is produced as preproinsulin which is composed of a prepeptide (signal peptide) with 24 amino-acid residues at the N terminus but, immediately after translocation through the rough endoplasmic reticulum, the prepeptide is cleaved to produce proinsulin.

The preproinsulin used in the present invention includes a protein consisting of the amino acid sequence of SEQ ID NO: 10 and a protein having substantially the same activity or function as the protein consisting of the amino acid sequence of SEQ ID NO: 10.

The term "substantially the same activity or function" is used to mean, for example: (i) a function that the substance formed from the protein above by cleavage of a signal peptide, cleavage at the two basic dipeptide portions and disulfide bond formation at the two portions lowers blood glucose levels; (ii) the activity of lowering blood glucose levels by the substance formed from the protein above through cleavage of a signal peptide, cleavage at the two basic dipeptide portions and disulfide bond formation at the two portions is ¼ or more, preferably ⅓ or more, more preferably ½ and most preferably 1/1.5 or more, than the activity of lowering blood glucose levels by insulin formed from the protein consisting of the amino acid sequence of SEQ ID NO: 10, or the like. The substantially the same activity or function is sometimes also referred to as the "insulin activity." The blood glucose-lowering activity described above can be assayed, for example, by administering a test compound to a test animal (mice, rats, spontaneously diabetic model KKAy mice, etc.) and measuring blood glucose levels before and after administration using known blood glucose assay methods, blood glucose meters and blood glucose kits commercially available, etc. Test animals which can be used are, for example, KKAy/Ta mice (CLEA Japan, Inc.). Blood glucose meters, blood glucose kits, etc. which can be used include, for example, Glucocard Diameter α, Diasensor (Arkray Co.), blood glucose meter Glutest Ace (GT-1640) (Sanwa Kagaku Kenkyusho Co.), blood glucose meter Dexter Z (Bayer Medical Ltd.), blood glucose meter Antosense II (Bayer-Sankyo), blood glucose meter Acucheck Comfort (Roche Diagnostics), Glucose CII-Test Wako (Wako Pure Chemicals), and the like.

The level of insulin can be measured using known methods, insulin measurement kits commercially available, etc. For example, the level of insulin can be measured using an insulin measurement kit commercially available (Morinaga Institute of Biological Science, Inc.), etc.

More specifically, the preproinsulin used in the present invention includes, for example, (a) a protein comprising the amino acid sequence of SEQ ID NO: 10; (b) a protein consisting of an amino acid sequence in which at least one amino acid residue is deleted, substituted, inserted and/or added in the amino acid sequence of SEQ ID NO: 10, and having the insulin activity; (c) a polypeptide comprising a polypeptide consisting of an amino acid sequence having at least 90% identity to the amino acid sequence of SEQ ID NO: 10, and having the insulin activity; (d) a polypeptide comprising a polypeptide consisting of an amino acid sequence encoded by a polynucleotide that hybridizes under stringent conditions to a polynucleotide consisting of a nucleotide sequence complementary to the nucleotide sequence of SEQ ID NO: 9, and having the insulin activity, etc.

Preferably, the preproinsulin includes the signal peptide of preproinsulin and one of the polypeptides described in (i) through (l).

(i) a polypeptide consisting of the amino acid sequence of SEQ ID NO: 4;

(j) a polypeptide comprising a polypeptide consisting of an amino acid sequence comprising deletion, substitution, insertion and/or addition of one to several amino acid residues in the amino acid sequence of SEQ ID NO: 4, and having the insulin activity;

(k) a polypeptide comprising a polypeptide consisting of an amino acid sequence having at least 90% identity to the amino acid sequence of SEQ ID NO: 4, and having the insulin activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having the insulin activity.

Preferably, the signal peptide of preproinsulin is a peptide consisting of the amino acid sequence of SEQ ID NO: 6.

The proinsulin used in the present invention includes a protein consisting of the amino acid sequence of SEQ ID NO:

10 and a protein having substantially the same activity or function as the protein consisting of the amino acid sequence of SEQ ID NO: 10.

The term "substantially the same activity or function" is used to mean, for example, (i) a function that the substance formed from the protein above by cleavage of a signal peptide, cleavage at the two basic dipeptide portions and disulfide bond formation at the two portions lowers blood glucose levels; (ii) the activity of lowering blood glucose levels by the substance formed from the protein above through cleavage of a signal peptide, cleavage at the two basic dipeptide portions and disulfide bond formation at the two portions is ¼ or more, preferably ⅓ or more, more preferably ½ and most preferably 1/1.5 or more, than the activity of lowering blood glucose levels by insulin formed from the protein consisting of the amino acid sequence of SEQ ID NO: 10, or the like.

(4) Fusion Protein of the Preproinsulin and the Luciferase

As used herein, the fusion protein of preproinsulin and the luciferase refers to a fusion protein of the preproinsulin described above and the luciferase described above.

As described above, where the luciferase is a secretory luciferase, the luciferase may have a signal peptide or may lack a signal peptide.

In the specification, the fusion protein of preproinsulin and the luciferase is sometimes also referred to as the "fusion protein of the present invention."

The fusion protein of the present invention comprises any one of the polypeptides described in any one of (m) through (p) below:

(m) a polypeptide consisting of the amino acid sequence of SEQ ID NO: 12;

(n) a polypeptide comprising a polypeptide consisting of an amino acid sequence comprising deletion, substitution, insertion and/or addition of one to several amino acid residues in the amino acid sequence of SEQ ID NO: 12, and having the insulin activity;

(o) a polypeptide comprising a polypeptide consisting of an amino acid sequence having at least 90% identity to the amino acid sequence of SEQ ID NO: 12, and having the insulin activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11, and having the insulin activity.

(5) Polynucleotide Encoding the Fusion Protein of the Present Invention

In the specification, the polynucleotide encoding the fusion protein of the preproinsulin and the luciferase described above is sometimes also referred to as the "polynucleotide encoding the fusion protein of the present invention."

In the specification, the polynucleotide encoding the fusion protein of the present invention is sometimes also referred to as the "polynucleotide of the present invention."

The polynucleotide of the present invention may be any polynucleotide as far as it is a polynucleotide comprising the nucleotide sequence encoding the fusion protein of the present invention, and is preferably a DNA.

The DNA includes genomic DNA, genomic DNA library, cDNA derived from the cells or tissues, cDNA library derived from the cells and tissues described above, synthetic DNA, etc. The vector used for the library may be any of bacteriophage, plasmid, cosmid and phagemide, and is not particularly limited. The DNA can also be directly amplified by reverse transcriptase polymerase chain reaction (hereinafter abbreviated as RT-PCR) employing a total RNA or a mRNA fraction prepared from the cells or tissues described above.

The polynucleotide of the invention includes: (m) a polynucleotide encoding a polypeptide consisting of the amino acid sequence of SEQ ID NO: 12; (n) a polynucleotide encoding a polypeptide comprising a polypeptide consisting of an amino acid sequence comprising deletion, substitution, insertion and/or addition of one to several amino acid residues in the amino acid sequence of SEQ ID NO: 12, and having the insulin activity; (o) a polypeptide comprising a polypeptide consisting of an amino acid sequence having at least 90% identity to the amino acid sequence of SEQ ID NO: 12, and having the insulin activity; and, (p) a polynucleotide encoding a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11, and having the insulin activity. The polynucleotide of the present invention is preferably (p2) a polynucleotide further comprising the nucleotide sequence of SEQ ID NO: 11, and more preferably (p3) a polynucleotide consisting of the nucleotide sequence of SEQ ID NO: 11.

As used herein, the "polynucleotide (e.g., a DNA) that hybridizes under stringent conditions" means a polynucleotide (e.g., a DNA) which is obtained by colony hybridization, plaque hybridization, Southern blot hybridization or the like using as a probe the whole or part of the target polynucleotide (for example, a polynucleotide (e.g., a DNA) consisting of a nucleotide sequence complementary to the nucleotide sequence of SEQ ID NO: 11 (for example, a polynucleotide encoding the amino acid sequence encoding the amino acid sequence of SEQ ID NO: 12 (e.g., a DNA)). Specifically, the polynucleotide includes a polynucleotide which can be identified by performing hybridization at 65° C. in the presence of 0.7 to 1.0 mol/L NaCl using a filter on which the DNA derived from colony or plaque is immobilized, and then washing the filter in 0.1 to 2×SSC (saline-sodium citrate) solution (1×SSC solution is composed of 150 mmol/L sodium chloride and 15 mmol/L sodium citrate) at 65° C.

Hybridization may be carried out based on the methods described in laboratory manuals such as Sambrook J. et al., Molecular Cloning: A Laboratory Manual, Third Edition, Cold Spring Harbor Laboratory Press (2001) (hereinafter briefly referred to as Molecular Cloning, 3rd edition), Ausbel F. M. et al., Current Protocols in Molecular Biology, Supplement 1-38, John Wiley and Sons (1987-1997), Glover D. M. and Hames B. D., DNA Cloning 1: Core Techniques, A Practical Approach, Second Edition, Oxford University Press (1995), etc.

As used herein, the "stringent conditions" may be any of low-stringent conditions, medium-stringent conditions and high-stringent conditions. The "low-stringent conditions" are, for example, 5×SSC, 5×Denhardt's solution, 0.5% (w/v) SDS, 50% (v/v) formamide and 32° C. The "medium-stringent conditions" are, for example, 5×SSC, 5×Denhardt's solution, 0.5% (w/v) SDS, 50% (v/v) formamide and 42° C. The "high-stringent conditions" are, for example, 5×SSC, 5×Denhardt's solution, 0.5% (w/v) SDS, 50% (v/v) formamide and 50° C. As the conditions become severer, complementation required for duplex formation becomes higher. Specifically, under these conditions, for example, as the temperature is higher, a DNA with higher homology is expected to be obtained efficiently, although multiple factors are involved in the hybridization stringency including temperature, probe concentration, probe length, ionic strength, time, salt concentration and the like. Those skilled in the art may achieve similar stringency by appropriately choosing these factors.

When a commercially available kit is used for hybridization, for example, Alkphos Direct Labeling Reagents (manufactured by Amersham Pharmacia) can be used. In this case, according to the attached protocol, a membrane is incubated with a labeled probe overnight, the membrane is washed with a primary wash buffer containing 0.1% (w/v) SDS at 55° C. and then the hybridized DNA can be detected.

Other polynucleotides that can be hybridized include DNAs having an identity of approximately 80% or higher, 85% or higher, 88% or higher, 90% or higher, 92% or higher, 95% or higher, 97% or higher. 98% or higher, 99% or higher, 99.3% or higher, 99.5% or higher, 99.7% or higher, 99.8% or higher or 99.9% or higher, to the nucleotide sequence of the target polynucleotide (e.g., DNA), as calculated by homology search software, such as FASTA and BLAST using default parameters.

The polynucleotide encoding a protein consisting of an amino acid sequence in which at least one amino acid residue is deleted, substituted, inserted and/or added in a given amino acid sequence may be obtained, using a site-specific mutagenesis technique (cf., for example, Gotoh, T. et al., Gene, 152, 271-275 (1995); Zoller, M. J. and Smith, M., Methods Enzymol., 100, 468-500 (1983); Kramer, W. et al., Nucleic Acids Res., 12, 9441-9456 (1984); Kramer, W. and Fritz, H. J., Methods Enzymol., 154, 350-367 (1987); Kunkel, T. A., Proc. Natl. Acad. Sci. USA, 82, 488-492 (1985); Kunkel, Methods Enzymol., 85, 2763-2766 (1988), etc.) and methods using amber mutation (cf., for example, the gapped duplex method in Nucleic Acids Res., 12, 9441-9456 (1984), etc.).

Alternatively, a mutation may also be introduced onto the polynucleotide by PCR using a set of primers bearing on each 5' end a sequence in which the target mutation (deletion, addition, substitution and/or insertion) has been introduced (cf., for example, Ho, S. N. et al., Gene, 77, 51 (1989), etc.).

Specific examples of the polynucleotide (i.e., polynucleotide encoding the fusion protein of the preproinsulin and the luciferase) of the present invention include:
(i) a polynucleotide encoding the fusion protein of preproinsulin and a secretory luciferase;
(ii) a polynucleotide encoding the fusion protein of preproinsulin and *Gaussia* luciferase;
(iii) a polynucleotide encoding the fusion protein of preproinsulin and the protein (*Gaussia* luciferase) described in any one of (a) through (d) below;
(a) a protein comprising the amino acid sequence of SEQ ID NO: 8;
(b) a protein consisting of an amino acid sequence in which at least one amino acid residue is deleted, substituted, inserted and/or added in the amino acid sequence of SEQ ID NO: 8, and having the luciferase activity;
(c) a protein consisting of an amino acid sequence having at least 90% identity to the amino acid sequence of SEQ ID NO: 8, and having the luciferase activity; and,
(d) a protein consisting of an amino acid sequence encoded by a polynucleotide that hybridizes under stringent conditions to a polynucleotide consisting of a nucleotide sequence complementary to the nucleotide sequence of SEQ ID NO: 7, and having the luciferase activity;
(iv) a polynucleotide encoding the fusion protein of preproinsulin and the protein (*Gaussia* luciferase) described in any one of (a) through (d) below:
(a) a protein comprising the amino acid sequence of SEQ ID NO: 8;

(b) a protein consisting of an amino acid sequence comprising deletion, substitution, insertion and/or addition of one to several amino acid residues in the amino acid sequence of SEQ ID NO: 8, and having the luciferase activity;
(c) a protein consisting of an amino acid sequence having at least 90% identity to the amino acid sequence of SEQ ID NO: 8, and having the luciferase activity;
(d) a protein consisting of an amino acid sequence encoded by a polynucleotide that hybridizes under high stringent conditions to a polynucleotide consisting of a nucleotide sequence complementary to the nucleotide sequence of SEQ ID NO: 7, and having the luciferase activity;
(v) a polynucleotide encoding the fusion protein of the polypeptide (preproinsulin) described in any one of (e) through (h) below and the luciferase described in any one of (i) through (iv) above:
(e) a polypeptide consisting of the amino acid sequence of SEQ ID NO: 10;
(f) a polypeptide comprising a polypeptide consisting of an amino acid sequence comprising deletion, substitution, insertion and/or addition of one to several amino acid residues in the amino acid sequence of SEQ ID NO: 10, and having the insulin activity;
(g) a polypeptide comprising a polypeptide consisting of an amino acid sequence having at least 90% identity to the amino acid sequence of SEQ ID NO: 10, and having the insulin activity; and,
(h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 9, and having the insulin activity;
(vi) a polynucleotide encoding the fusion protein between a polypeptide (preproinsulin), which consists of the signal peptide of preproinsulin and the polypeptide described in any one of (i) through (l) below, and the luciferase described in any one of (i) through (iv) above:
(i) a polypeptide consisting of the amino acid sequence of SEQ ID NO: 4;
(j) a polypeptide comprising a polypeptide consisting of an amino acid sequence comprising deletion, substitution, insertion and/or addition of one to several amino acid residues in the amino acid sequence of SEQ ID NO: 4, and having the insulin activity;
(k) a polypeptide comprising a polypeptide consisting of an amino acid sequence having at least 90% identity to the amino acid sequence of SEQ ID NO: 4, and having the insulin activity; and,
(l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having the insulin activity.
(vii) a polynucleotide encoding the fusion protein between a polypeptide (preproinsulin), which consists of a polypeptide (signal peptide of preproinsulin) consisting of the amino acid sequence of SEQ ID NO: 6 and the polypeptide described in any one of (i) through (l) below, and the luciferase described in any one of (1) through (4) above:
(i) a polypeptide consisting of the amino acid sequence of SEQ ID NO: 4;
(j) a polypeptide comprising a polypeptide consisting of an amino acid sequence comprising deletion, substitution, insertion and/or addition of one to several amino acid residues in the amino acid sequence of SEQ ID NO: 4, and having the insulin activity;

(k) a polypeptide comprising a polypeptide consisting of an amino acid sequence having at least 90% identity to the amino acid sequence of SEQ ID NO: 4, and having the insulin activity; and, (l) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having the insulin activity;

(viii) a polynucleotide described in any one of (i) through (vii) above, encoding the polypeptide described in any one of (m) through (p) below:

(m) a polypeptide consisting of the amino acid sequence of SEQ ID NO: 12;

(n) a polypeptide comprising a polypeptide consisting of an amino acid sequence comprising deletion, substitution, insertion and/or addition of one to several amino acid residues in the amino acid sequence of SEQ ID NO: 12, and having the insulin activity;

(o) a polypeptide comprising a polypeptide consisting of an amino acid sequence having at least 90% identity to the amino acid sequence of SEQ ID NO: 12, and having the insulin activity; and, (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11, and having the insulin activity; and the like.

The present invention can further provide the recombinant vector and transformant comprising the polynucleotide described above.

(6) Recombinant Vector

The vector capable of expressing the fusion protein of the present invention can be obtained by ligating (inserting) the polynucleotide encoding the fusion protein of the preproinsulin and the luciferase (the polynucleotide of the invention (DNA)) to a suitable vector.

As used herein, the recombinant vector bearing the polynucleotide of the invention is sometimes also referred to as the "recombinant vector of the invention."

More specifically, the recombinant vector may be obtained by cleaving a purified polynucleotide (DNA) with a suitable restriction enzyme, then inserting the resulting fragment into a restriction enzyme site or multicloning site on a suitable vector, and ligating to the vector. The vector for inserting the polynucleotide of the invention includes, for example, but not limited to, plasmids, bacteriophages, animal viruses, and the like. Examples plasmids include plasmids derived from *Escherichia coli* (e.g., pBR322, pBR325, pUC118, pUC119, etc.), plasmids derived from *Bacillus subtilis* (e.g., pUB110 and pTP5), and plasmids derived from yeast (e.g., YEp13, YEp24 and YCp50). An example of bacteriophage is λ phage. Examples of animal viruses include retroviruses, vaccinia viruses, insect viruses (e.g., baculoviruses), etc.

The polynucleotide of the invention is generally ligated downstream of the promoter in a suitable vector in an expressible form. Where the host used for transformation is an animal cell, preferred promoters are promoters from SV40, retrovirus promoters, metallothionein promoters, heat shock promoters, cytomegalovirus promoters, SRα promoters and the like. Where the host is bacteria belonging to the genus *Escherichia*, preferred promoters include Trp promoter, T7 promoter, lac promoter, recA promoter, λPL promoter, lpp promoter, etc. Where the host is bacteria belong to genus *Bacillus*, preferred promoters include SPO1 promoter, SPO2 promoter, penP promoter, etc. Where the host is a yeast, preferred promoters include PHO5 promoter, PGK promoter, GAP promoter, ADH1 promoter, GAL promoter, etc. Where the host is an insect cell, preferred promoters include polyhedrin promoter, P10 promoter, etc.

In addition to the foregoing, the recombinant vector of the invention which can be used may contain, if desired, an enhancer, a splicing signal, a poly(A) addition signal, a ribosome binding sequence (SD sequence), a selective marker and the like. Examples of selective markers include dihydrofolate reductase gene, ampicillin resistance gene, neomycin resistance gene, etc.

(7) Transformant

The transformant can be produced by introducing the recombinant vector comprising the polynucleotide of the invention (i.e., the polynucleotide encoding the fusion protein of the invention) into a suitable host.

In the specification, the transformant comprising the recombinant vector of the present invention is sometimes also referred to as the "transformant of the invention."

The host used to produce the transformant of the invention is not particularly limited, so long as the host is capable of expressing the polynucleotide (DNA) of the invention. Examples include bacteria of the genera *Escherichia*, *Bacillus*, *Pseudomonas* and *Rhizobium*, yeasts, animal cells and insect cells. Bacteria of the genus *Escherichia* include, for example, *Escherichia coli*. Bacteria of the genus *Bacillus* include, for example, *Bacillus subtilis*. Bacteria of the genus *Pseudomonas* include, for example, *Pseudomonas putida*. Bacteria of the genus *Rhizobium* include *Rhizobium meliloti*. Yeasts include, for example, *Saccharomyces cerevisiae* and *Schizosaccharomyces pombe*. Animal cells include, for example, COS cells and CHO cells. Insect cells include, for example, Sf9 and Sf21.

Among others, animal cells and cell lines derived from animal cells are preferred as the host. More preferably, the host is animal cells capable of secreting insulin, pancreatic Langerhans islet β cells and cell lines derived from these cells.

Introduction of the recombinant vector into the host and transformation thereby may be performed by various methods generally used. These methods for introducing the recombinant vector into the host cell include the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. Methods for transforming bacteria of the genus *Escherichia* include, for example, the methods described in Proc. Natl. Acad. Sci. USA, 69, 2110 (1972), Gene, 17, 107 (1982), etc. Methods for transforming bacteria of the genus *Bacillus* include, for example, the methods described in Molecular & General Genetics, 168, 111 (1979). Methods for transforming yeasts include, for example, the methods described in Proc. Natl. Acad. Sci. USA, 75, 1929 (1978). Methods for transforming animal cells include, for example, the methods described in Virology, 52, 456 (1973). Methods for transforming insect cells include, for example, the methods described in Bio/Technology, 6, 47-55 (1988). The transformant comprising the polynucleotide encoding the protein of the invention (polynucleotide of the invention) can be produced in such a way.

(8) Culture of the Transformant of the Invention

The transformant of the invention may be cultured in a conventional manner used for culturing hosts. The transformant is so cultured to produce the fusion protein of the invention, and the fusion protein of the invention is secreted into the culture broth.

The medium for culturing the transformant using bacteria of the genus *Escherichia* or the genus *Bacillus* as a host may be any of a natural medium and a synthetic medium, as far as it is a medium which contains carbon sources, nitrogen sources, inorganic salts, etc. necessary for growth of the transformant, and in which the transformant can be efficiently grown. Examples of carbon sources which may be used are carbohydrates such as glucose, fructose, sucrose, starch, etc.; organic acids such as acetic acid, propionic acid, etc.; alcohols such as ethanol and propanol, and the like. Examples of nitrogen sources which may be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. Antibiotics such as ampicillin or tetracycline may be added to the medium during culture, depending on necessity. Where the transformant transformed by an expression vector using an inducible promoter as the promoter, if necessary, an inducer may also be added to the medium. For example, isopropyl-β-D-thiogalactopyranoside (IPTG), etc. may be added to the medium when a transformant transformed by an expression vector using a Lac promoter is cultured, and indoleacrylic acid (IAA), etc. may be added to the medium when a transformant transformed by an expression vector using a trp promoter is cultured.

When the host is bacteria of the genus *Escherichia*, incubation is performed generally at approximately 15 to 43° C. for approximately 3 to 24 hours. If necessary, aeration and agitation may be applied. When the host is bacteria of the genus *Bacillus*, incubation is performed generally at approximately 30 to 40° C. for approximately 6 to 24 hours. If necessary, aeration and agitation may be applied.

Media for culturing the transformant when the host is yeast include Burkholder's minimal medium (Proc. Natl. Acad. Sci. USA, 77, 4505 (1980)) and an SD medium containing 0.5% (w/v) casamino acids (Proc. Natl. Acad. Sci. USA, 81, 5330 (1984)). Preferably, the pH of the medium is adjusted to approximately 5 to 8. Culture is performed generally at approximately 20 to 35° C. for approximately 24 to 72 hours. If necessary, aeration and agitation may be applied.

Media for culturing the transformant when the host is an animal cell include MEM medium containing approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Culture is performed generally at approximately 30 to 40° C. for approximately 15 to 60 hours. If necessary, aeration and agitation may be applied.

Media for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Culture is performed generally at approximately 27° C. for approximately 3 to 5 hours. If necessary, aeration and agitation may be applied.

The transformant of the invention is cultured under the culture conditions described above (i) in the absence of a test compound or (ii) in the presence of a test compound. Examples of the test compound are peptides, proteins, non-peptide compounds, synthetic compounds, fermentation products, cell extracts, plant extracts, animal tissue extracts, blood plasma and so on. The test compound may form a salt, and a pharmacologically acceptable salt is preferred as the salt of the test compound. Examples of pharmacologically acceptable salts include metal salts, ammonium salts, salts with organic bases, salts with inorganic acids, salts with organic acids, salts with basic or acidic amino acids, and the like. Examples of metal salts include alkali metal salts such as sodium salts, potassium salts, etc.; alkaline earth metal salts such as calcium salts, magnesium salts, barium salts, etc.; aluminum salts, and the like. Examples of salts with organic bases include salts with trimethylamine, triethylamine, pyridine, diethanolamine, triethanolamine, cyclohexylamine, dicyclohexylamine, N,N-dibenzylethylenediamine, etc. Examples of salts with inorganic acids include salts with hydrochloric acid, hydrobromic acid, nitric acid, sulfuric acid, phosphoric acid, etc. Examples of salts with organic acids include salts with formic acid, acetic acid, trifluoroacetic acid, propionic acid, phthalic acid, fumaric acid, oxalic acid, tartaric acid, maleic acid, citric acid, succinic acid, malic acid, methanesulfonic acid, benzoic acid, benzenesulfonic acid, p-toluenesulfonic acid, and the like. Examples of salts with basic amino acids include salts with arginine, lysine, ornithine, etc. Examples of salts with acidic amino acids include salts with aspartic acid, glutamic acid, and the like.

Step (b)
(8) Expression (Formation) of the Fusion Protein of the Invention and its Extracellular Secretion As described above, the transformant of the invention is cultured, whereby the fusion protein of the invention can be expressed (produced) in the transformant and secreted outside the cells (into a medium).

Luciferin which can cause the luciferin-luciferase reaction specifically with the luciferase in the fusion protein of the present invention is previously added to a medium. When the fusion protein of the present invention is secreted extracellularly, the luciferin-luciferase reaction with the luciferin in the medium is caused to emit light. This luminescence is observed, detected or measured, and the localization (distribution), secretion, quantification, etc. of the fusion protein of the present invention can be observed, detected or measured.

Step (c)
(9) Luminescence Imaging

As used herein, luminescence imaging means the observation, detection or measurement of luminescence.

The transformant of the present invention is capable of expressing and secreting the fusion protein of the present invention. The fusion protein of the present invention can cause the luciferin-luciferase reaction between the luciferase in the fusion protein and the luciferin specific to the luciferase above. As described above, light emits by the luciferin-luciferase reaction. By observing, detecting or measuring this luminescence, the localization (distribution), secretion, quantification, etc. of the fusion protein of the present invention can be observed, detected or measured.

Specifically, the luminescence imaging can be performed using an optical detection device (e.g., a camera), including a camera such as a CCD camera, a photon counting camera, etc. (an electron camera), which detects light electronically, a camera such as a film camera, etc. (a film camera or a silver halide camera), which detects light scientifically. A monochrome CCD camera, a 3CCD camera, a single CCD color camera, a digital CCD camera, etc. can be used. Furthermore, a ultra-weak-light detectable CCD camera may also be used and includes an electronically cooled CCD, a liquid nitrogen-cooled CCD, a CCD with imaging intensifier, etc.

Preferably, the ultra-weak-light detectable CCD imaging camera is an EM-CCD camera (e.g., model C9100-13 manufactured by Hamamatsu Photonics K. K., model C9100-14 model manufactured by Hamamatsu Photonics K. K., model QuantEM manufactured by Princeton Instrument Inc., Evolve manufactured by Photometrics Corp., model Night-OWL II LB983 em100 manufactured by Berthold Inc., etc.). The photon counting camera model which may be used includes a device commercially available such as a VIM camera manufactured by Hamamatsu Photonics K. K. The VIM camera manufactured by Hamamatsu Photonics K. K. is equipped with an optical amplifier and a CCD camera.

The luminescence imaging may be performed using a microscope in addition to the optical detection device, preferably using a microscope. Microscopes commercially available may also be used and include, e.g., an inverted microscope such as models IX71 and IX81 manufactured by Olympus Corporation.

The luminescence imaging may also be performed further using an image intensifier (optical amplifier device) such as an optical amplifier tube, a semiconductor optical amplifier device, etc., in addition to the optical detection device, preferably using an optical amplifier device. The optical amplifier device which may be used includes a semiconductor photo-detector (e.g., a GaAsP (gallium arsenic phosphide) image intensifier, etc.), a photomultiplier, etc. The optical amplifier device is preferably a GaAsP image intensifier (e.g., model C8600-04 manufactured by Hamamatsu Photonics K. K.).

Step (d)

(10) Screening of the Compound that Promotes (or Regulates) the Secretion of the Fusion Protein of the Invention or Insulin Secretion from Cells As described above, the transformant of the present invention is cultured in the absence of a test compound and in the presence of the test compound and levels of secretion or the like of the fusion protein of the invention are measured in the respective cases by observing the luminescence caused by the luciferin-luciferase reaction. By comparing the levels of secretion or the like of the fusion protein of the invention in the absence and the presence of the test compound, a substance that promotes (or regulates) the secretion or the like of the fusion protein of the invention or insulin from cells can be screened.

More specifically, the substance that promotes (or regulates) the secretion of the fusion protein of the invention or insulin from cells can be screened by measuring the levels of secretion, etc. of the fusion protein of the present invention when the transformant of the present invention is cultured (i) in the absence of a test compound and the levels of secretion, etc. of the fusion protein of the present invention when the transformant of the present invention is cultured (ii) in the presence of the test compound, and comparing the secretion levels by luminescence imaging.

More specifically, for example, in the case of (ii) above, a test compound which promotes the level of secretion of the fusion protein of the invention by about 10% or more, preferably about 20% or more, more preferably about 30% or more, much more preferably about 40% or more and most preferably about 50% or more, when compared to the case of (i) above, can be selected as a substance that promotes (or regulates) the secretion of the fusion protein or the invention or the insulin secretion, etc.

Screening Method 2:

The method of screening a substance that regulates the secretion of MMP-2 from cells, which comprises Steps (a') through (d') below:

Step (a'): the step of culturing a cell transformed by the polynucleotide encoding the fusion protein of the luciferase and pro-MMP-2 in a medium in the presence or absence of a test compound;

Step (b'): the step of expressing the fusion protein of the present invention to secrete the fusion protein of the invention into a luciferin-containing medium (outside the cells).

Step (c'): the step of observing the fusion protein secreted extracellularly by luminescence imaging; and, Step (d'): the step of comparing the expression and/or activity of the fusion protein or the cancer metastasis suppressing activity, etc. in the presence of or in the absence of a test compound.

The steps are explained below in detail.

Step (a')

(1') Luciferase

The luciferase used in the present invention is as described in the screening method 1 above. The luciferase used includes those listed in the screening method 1 above and preferred examples are the same as well.

(2') Luciferin

The luciferin used in the present invention is as described in the screening method 1 above. The luciferin used includes those listed in the screening method 1 above and preferred examples are the same as well.

(3') pro-MMP-2 and MMP-2

Matrix metalloproteinase (MMP)-2 is a zinc-dependent endopeptidase involved in the degradation and repair of the major components of extracellular matrix and connective tissues. MMP-2 has an activity of degrading type IV collagen as the main components of the basal membrane and denatured collagen (gelatin). MMP-2 also has an activity of disrupting vascular membranes mainly composed of type IV collagen. Based on these activities, MMP-2 plays an important role in tumor metastasis.

MMP-2 is synthesized as pro-MMP-2 in which the signal peptide is appended to the N terminus. pro-MMP-2 is activated through cleavage of the signal peptide to form MMP-2.

The pro-MMP-2 used in the present invention comprises a protein consisting of the amino acid sequence of SEQ ID NO: 18 and a protein having substantially the same activity or function as the protein consisting of the amino acid sequence of SEQ ID NO: 18.

The term "substantially the same activity or function" is used to mean that, for example: (i) the activity of degrading the active protein type IV collagen produced from the protein above via cleavage of the signal peptide or the activity of degrading denatured collagen (gelatin) is ¼ or more, preferably ⅓ or more, more preferably ½ and most preferably 1/1.5 or more, than the type IV collagen degradation activity or denatured collagen (gelatin) degradation activity of MMP-2 produced from the protein consisting of the amino acid sequence of SEQ ID NO: 8, or the like. The substantially the same activity or function is sometimes referred to as "a MMP-2 activity." The type IV collagen degradation activity or denatured collagen (gelatin) degradation activity described above can be assayed by adding the protein described above or MMP-2 to type IV collagen or denatured collagen (gelatin) to perform their degradation reaction for a given period of time and quantitatively determining the type IV collagen or denatured collagen (gelatin) remained using HPLC, gel electrophoresis, etc.

More specifically, the pro-MMP-2 used in the present invention includes, for example, (a') a protein comprising the amino acid sequence of SEQ ID NO: 18; (b') a protein consisting of an amino acid sequence in which at least one amino acid residue is deleted, substituted, inserted and/or added in the amino acid sequence of SEQ ID NO: 18, and having the MMP-2 activity; (c') a protein consisting of an amino acid sequence having at least 90% identity to the amino acid sequence of SEQ ID NO: 18, and having the MMP-2 activity; and, (d') a protein consisting of an amino acid sequence encoded by a polynucleotide that hybridizes under stringent conditions to a polynucleotide consisting of a nucleotide sequence complementary to the nucleotide sequence of SEQ ID NO: 17, and having the MMP-2 activity, and the like.

The pro-MMP-2 used in the present invention further includes, for example, (a') a protein comprising the amino acid sequence of SEQ ID NO: 18; (b') a protein consisting of an amino acid sequence in which at least one amino acid residue is deleted, substituted, inserted and/or added in the amino acid sequence of SEQ ID NO: 18 and having the MMP-2 activity in the form of the active protein which is obtained by cleavage of the signal peptide from the amino acid sequence above; (c') a protein consisting of an amino acid sequence having at least 90% identity to the amino acid sequence of SEQ ID NO: 18, and having the MMP-2 activity in the form of the active protein which is obtained by cleavage of the signal peptide from the amino acid sequence above; and, (d') a protein consisting of an amino acid sequence encoded by a polynucleotide that hybridizes under stringent conditions to a polynucleotide consisting of a nucleotide sequence complementary to the nucleotide sequence of SEQ ID NO: 17, and having the MMP-2 activity in the form of the active protein which is obtained by cleavage of the signal peptide from the amino acid sequence above, and the like.

Preferably, the pro-MMP-2 consists of the signal peptide of pro-MMP-2 and the protein described in any one of (i') through (P) below:

(i') a protein consisting of the amino acid sequence of SEQ ID NO: 14;

(j') a protein comprising a polypeptide consisting of an amino acid sequence comprising deletion, substitution, insertion and/or addition of one to several amino acid residues in the amino acid sequence of SEQ ID NO: 14, and having the MMP-2 activity;

(k') a protein comprising a polypeptide consisting of an amino acid sequence having at least 90% identity to the amino acid sequence of SEQ ID NO: 4, and having the MMP-2 activity; and, (l') a protein comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 3, and having the MMP-2 activity.

Preferably, the signal peptide of pro-MMP-2 is a peptide consisting of the amino acid sequence of SEQ ID NO: 16.

(4') Fusion Protein Between pro-MMP-2 and Luciferase

As used herein, the fusion protein of pro-MMP-2 and the luciferase refers to the pro-MMP-2 described above and the luciferase described above.

As described above, where the luciferase is a secretory luciferase, the luciferase may have a signal peptide or may lack a signal peptide.

In the specification, the fusion protein of pro-MMP-2 and the luciferase is sometimes also referred to as the "fusion protein of the present invention."

The fusion protein of the present invention comprises the protein described in any one of (m') through (p') below:

(m') a protein consisting of the amino acid sequence of SEQ ID NO: 20;

(n') a protein comprising a polypeptide consisting of an amino acid sequence comprising deletion, substitution, insertion and/or addition of one to several amino acid residues in the amino acid sequence of SEQ ID NO: 20, and having the MMP-2 activity;

(o') a protein comprising a polypeptide consisting of an amino acid sequence having at least 90% identity to the amino acid sequence of SEQ ID NO: 20, and having the MMP-2 activity; and, (p') a protein comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 19, and having the MMP-2 activity.

(5') Polynucleotide Encoding the Fusion Protein of pro-MMP-2 and the Luciferase

In the specification, the polynucleotide encoding the fusion protein of pro-MMP-2 and the luciferase is sometimes also referred to as the polynucleotide encoding the fusion protein of the present invention.

In the specification, the polynucleotide encoding the fusion protein described above is sometimes also referred to as the "polynucleotide of the present invention."

The polynucleotide of the present invention may be any polynucleotide as far as it is a polynucleotide comprising the nucleotide sequence encoding the fusion protein of the present invention, and is preferably a DNA.

The polynucleotide of the present invention includes (m') a polynucleotide encoding the protein consisting of the amino acid sequence of SEQ ID NO: 20; (n') a polynucleotide encoding the protein consisting of an amino acid sequence comprising deletion, substitution, insertion and/or addition of one to several amino acid residues in the amino acid sequence of SEQ ID NO: 20, and having the MMP-2 activity; (o') a protein comprising a polypeptide consisting of an amino acid sequence having at least 90% identity to the amino acid sequence of SEQ ID NO: 20, and having the MMP-2 activity; and, (p') a polynucleotide encoding a protein comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 19, and having the MMP-2 activity. The polynucleotide of the present invention is preferably (p2') a polynucleotide comprising the nucleotide sequence of SEQ ID NO: 19, and more preferably (p3') a polynucleotide consisting of the nucleotide sequence of SEQ ID NO: 19.

According to the present invention, the recombinant vector and transformant bearing the polynucleotide of the present invention described above can be further provided.

(6') Recombinant Vector

A vector capable of expressing the fusion protein of the invention can be acquired by ligating (inserting) the polynucleotide encoding the fusion protein of pro-MMP-2 and the luciferase (polynucleotide of the present invention (DNA)) to or into a suitable vector.

In the specification, the recombinant vector bearing the polynucleotide of the present invention is sometimes also referred to as the "recombinant vector of the present invention."

More specifically, the recombinant vector of the present invention can be produced as described above.

(7') Transformant

The transformant can be prepared by introducing into a suitable host the recombinant vector bearing the polynucleotide encoding the fusion protein of this pro-MMP-2 and the luciferase (namely, the polynucleotide encoding the fusion protein of the present invention) thus produced.

In the specification, the transformant bearing the recombinant vector of the present invention is sometimes also referred to as the "transformant of the present invention."

More specifically, the transformant of the present invention can be prepared as described above.

(8') Culture of the Transformant of the Invention

The transformant of the present invention can be cultured in a conventional manner used in the culture of a host, as described above. By the culture, the fusion protein of the invention is produced and the fusion protein of the present invention is secreted into the culture broth.

Step (c')

(9') Luminescence Imaging

The luminescence imaging can be performed as described above.

Step (d')

(10') Screening of a Compound that Promotes (or Regulates) the Secretion of the Fusion Protein of the Invention or MMP-2 Secretion from Cells As described above, the transformant of the present invention is cultured in the absence of a test compound and in the presence of the test compound and levels of secretion or the like of the fusion protein of the invention are measured in the respective cases by observing the luminescence caused by the luciferin-luciferase reaction. By comparing the levels of secretion or the like of the fusion protein of the invention in the absence of the test compound and the presence of the test compound, a substance that promotes (or regulates) the secretion or the like of the fusion protein of the invention or MMP-2 from cells can be screened.

More specifically, the substance that promotes (or regulates) the secretion of the fusion protein of the invention or MMP-2 from cells can be screened by measuring the levels of secretion, etc. of the fusion protein of the present invention when the transformant of the present invention is cultured (i') in the absence of a test compound and the levels of secretion, etc. of the fusion protein of the present invention when the transformant of the present invention is cultured (ii') in the presence of the test compound, and comparing the secretion levels by luminescence imaging.

More specifically, for example, in the case of (ii') above, a test compound which promotes the level of secretion of the fusion protein of the invention by about 10% or more, preferably about 20% or more, more preferably about 30% or more, much more preferably about 40% or more and most preferably about 50% or more, when compared to the case of (i') above, can be selected as a substance that promotes (or regulates) the secretion of the fusion protein or the invention or the MMP-2 secretion, etc.

EXAMPLES

Example 1-1

Construction of Fusion Protein Between Human Preproinsulin (hINS) and *Gaussia* Luciferase (GLase)

The expression vector pcDNA3-hINS-GLuc to express the fusion protein between human preproinsulin and *Gaussia* luciferase was prepared according to the following procedures.

The BamHI-EcoRI cDNA fragment encoding human preproinsulin was obtained by PCR using as a template IMAGE cDNA clone 3950204 (cf. http://image.llnl.gov/image/html/vectors.shtml). Using KOD-plus-DNA polymerase (manufactured by Toyobo Co., Ltd.) and primers hINS-P1 (5'ctc GGATCC AGCCACC ATG GCC CTG TGG ATG CGC CT 3'; BamHI recognition site underlined) (SEQ ID NO: 21) and hINS-P2 (5' ctt GAATTC GTT GCA GTA GTT CTC CAG CTG 3'; EcoRI recognition site underlined) (SEQ ID NO: 22), PCR was carried out under the following cycle conditions: 25 cycles of 15 secs/96° C., 15 secs/55° C. and 45 secs/68° C. The DNA fragment obtained was digested with BamHI and EcoRI and then inserted into the BamHI/EcoRI site of pcDNA3-GLuc-BE vector (described in FEBS Letters, 581, 4551-4556 (2007)) to construct expression vector pcDNA3-hINS-GLuc.

The protein expressed by the expression vector pcDNA3-hINS-GLuc obtained is the fusion protein of insulin signal peptide sequence, proinsulin and *Gaussia* luciferase.

Example 1-2

Construction of a Transformant Using Expression Vector pcDNA3-hINS-GLuc and Assessment of the Transformant Mouse pancreatic β cells, MIN6 strains, were cultured in high glucose DMEM (manufactured by Sigma) supplemented with 10% fetal calf serum (manufactured by Invitrogen) and 50 μM of 2-mercaptoethanol.

The expression vector obtained in EXAMPLE 1-1 was transfected to the MIN6 cell line using LipofectAMINE 2000 (manufactured by Invitrogen). After the transfection, the cells were incubated in a $CO_2$ incubator at 37° C. for 24 hours.

The secretion expression of the fusion *Gaussia* luciferase protein in the transformant was confirmed by measuring the luminescence activity with a Luminometer AB2200 (manufactured by Atto Corporation) using coelenterazine as a luminescent substrate, in accordance with the method described in Biochem. Biophys. Res. Commun., 365, 96-101 (2007). As a result, the luminescence activity in the cultured medium by high glucose (20 mM glucose) stimulation to the transformed MIN6 cells increased by about 7 times as compared to that prior to the treatment (FIG. 1). This revealed that insulin secretion can be assessed in this expression vector pcDNA3-hINS-GLuc-animal culture cell system.

Example 1-3

Imaging of the Extracellular Secretion of Insulin by the Expression of Human Insulin-*Gaussia* Luciferase Fusion Protein The MIN6 cells to visualize insulin secretion were cultured on a 35 mm glass-bottom culture dish coated with poly-D-lysine (manufactured by Mat-Tek).

An EM-CCD camera was used to visualize insulin secreted from cells by the addition of and stimulation with high concentration glucose using a luminescence signal from the insulin-GLase fusion protein.

More specifically, the MIN6 cell line transformed was rinsed 3 times with 3 ml of phosphate buffered saline (PBS) and soaked with 1 ml of a buffer containing 3 μg/ml of coelenterazine. The buffer used was low glucose-modified KRHB buffer (Krebs-Ringer Hepes buffer: 130 mM NaCl, 4.7 mM KCl, 1.2 mM $KH_2PO_4$, 1.2 mM $MgSO_4$, 1.5 mM $CaCl_2$, 10 mM Hepes (pH 7.4), containing 2 mM glucose).

After rinsing 1 ml of the buffer above, luminescence video images of the cells in low-glucose KRHB buffer (2 mM glucose) containing 3 µg/ml of coelenterazine were obtained. In order to acquire luminescence video images of the same cells as described above in high-glucose buffer, 1 ml of KRHB buffer containing 38 mM glucose and 3 µg/ml of coelenterazine was then added to the cultured medium to acquire the luminescence video images.

Visualization by the luminescence imaging method is as follows. The luminescence signals produced from the cells as a result of luciferin-luciferase reaction of *Gaussia* luciferase with coelenterazine were taken at 37° C. using a model IX71 microscope (manufactured by Olympus Corporation) equipped with a thermostat incubator (manufactured by Tokai Hit Co.) and an EM-CCD camera (model C9100-13; 512× 512 pixels, pixel size=16 µm; manufactured by Hamamatsu Photonics K. K.) in a dark box. The following objective lens with a high aperture number (NA) was used. UPLFLN 40× O (NA 1.30), ApoN 60× OTIRFM (NA 1.49) and PlanApo 100× OTIRFM (NA 1.45) (manufactured by Olympus Corporation).

The luminescence video images were recorded onto the hard disk of a computer using an AQUACOSMOS software version 2.6 (manufactured by Hamamatsu Photonics K. K.). The acquisition mode of the luminescence signal data using the AQUACOSMOS software above was used at 1×1 binning, fast scanning and photon-counting level=1. The luminescence video images acquired were processed and analyzed using the software above. In a few cases, the successive luminescence images were acquired using the "MaxTrace" method in the "sequential calculation" menu of the above software and displayed as picture images showing the maximum luminescence intensity.

The luminescence images acquired by the successive luminescence images were superimposed on the bright-field images to display the localization of luminescence signals in the individual cells. In order to analyze the time-lapse change of luminescence intensity change of luminescence intensity in video images, the mean luminescence intensity and maximum luminescence intensity within a particular luminescence region were calculated.

The transformant derived from MIN6 cell line transiently expressing the insulin-GLase fusion protein described above was analyzed by the luminescence imaging method, using an EM-CCD camera-microscope device (objective lens ×60; NA 1.49).

The luminescence signals of insulin-GLase fusion protein by exocytosis from the transformant derived from the MIN6 cell line cultured in a medium under low glucose conditions (2 mM glucose) were little detected when observed in time resolution of 100-500 ms/frame.

After transfection, the insulin-GLase expression vector constructed in Example 1-1 above was cultured for 24 hours. This transiently transfected cell cluster derived from the Min6 cell line (FIG. 2, let: bright-field image) was stimulated by high glucose (20 mM glucose) medium containing coelenterazine. One minute after the onset of stimulation, luminescence video images were acquired for about 11.8 minutes at 100 ms/frame for 7000 frames.

Figure 2:
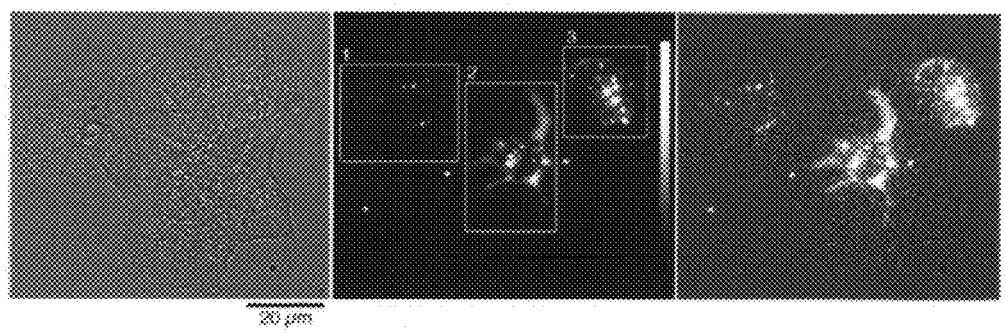
FIG. 2 shows the luminescence images of insulin-GLase fusion protein secreted by stimulation of glucose added to the transformant derived from the MIN6 cell line obtained in EXAMPLE 1-3. Left, bright-field image; center, luminescence signal image; right, image obtained by superimposing the luminescent image on the bright-field image.

After stimulation by 20 mM glucose, luminescence spots showing the secretion of the insulin-GLase fusion protein were frequently observed (FIG. 2, center: images of luminescence signals). By superimposing the bright-field images of the cells on the luminescence images, images of insulin secretion can be acquired. It is thus possible to identify the secretion sites in cells (FIG. 2, right).

Figure 3:
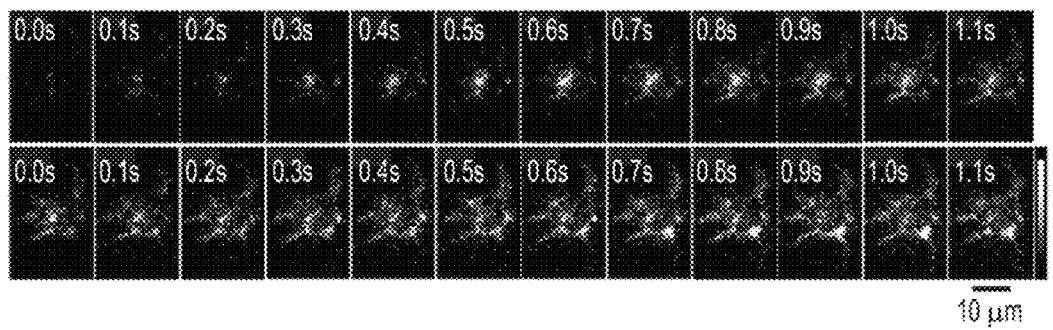
FIG. 3 shows the images of luminescence signals acquired at 100 msec, indicating time-lapse changes of the insulin-GLase fusion protein secreted in a periodic pulsatile manner by stimulation of glucose added to the transformant derived from the MIN6 cell line obtained in EXAMPLE 1-3.

Furthermore, editing of the successive high-speed luminescence images at 100 msec enables real-time imaging of insulin secretion (FIG. 3). As a result, editing of the successive composite images produced from the maximum luminescence intensities of all luminescence images revealed that the insulin-GLase fusion protein was secreted from the intercellular spaces of cell clusters of the transformant of MIN6 cells.

Figure 4:
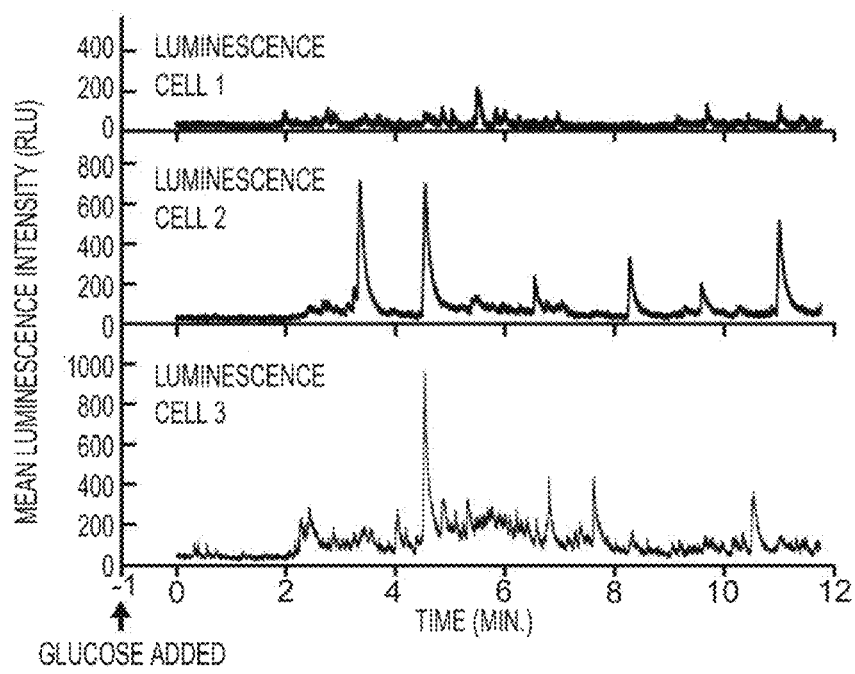
FIG. 4 is graphs formed by quantifying time-lapse changes of the insulin-GLase fusion protein secreted by stimulation of glucose added, in the cell regions 1 to 3 designated in FIG. 2.

The cells exhibiting a secretory luminescence are shown in the cell regions 1 to 3 at the center of FIG. 2, and time-lapse changes of the mean luminescence intensity in the cell regions 1 to 3 were calculated (FIG. 4).

The luminescence signals in the region 2 were detected in the narrow intercellular spaces where the cells interact with each other, and a few minutes after the high glucose stimulation, the luminescence intensity displayed a periodic pattern. The typical peaks of insulin-GLase secretion from the two cells in the regions 2 and 3 were analyzed, respectively (FIG. 4). These peaks represent the mass secretion of insulin-GLase generated by successive appearance of luminescence spots. These many luminescence signals generated by the mass secretion appeared successively around the edges of cells and then diffused in the region of intercellular spaces. This phenomenon was remarkable especially in the cells in the region 2. This enabled the dynamic analysis and quantification of insulin secretion at the same time.

Figure 5:
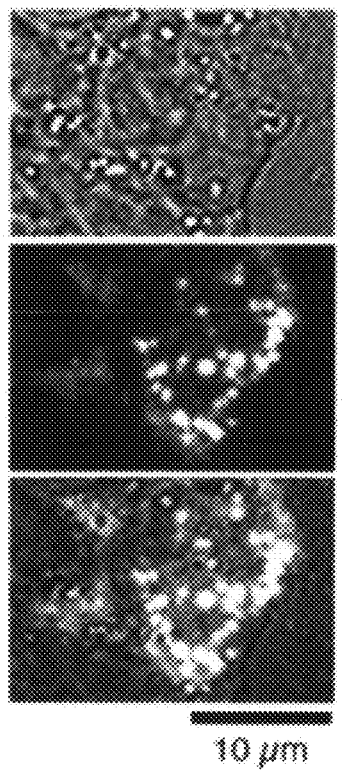
FIG. 5 shows the luminescence images showing the distribution of the insulin-GLase fusion protein secreted by stimulation of glucose added to the transformant derived from the MIN6 cell line obtained in EXAMPLE 1-3. Upper: bright-field image, center: luminescence signal image, lower: image superimposed on the bright-field image.
Figure 6:
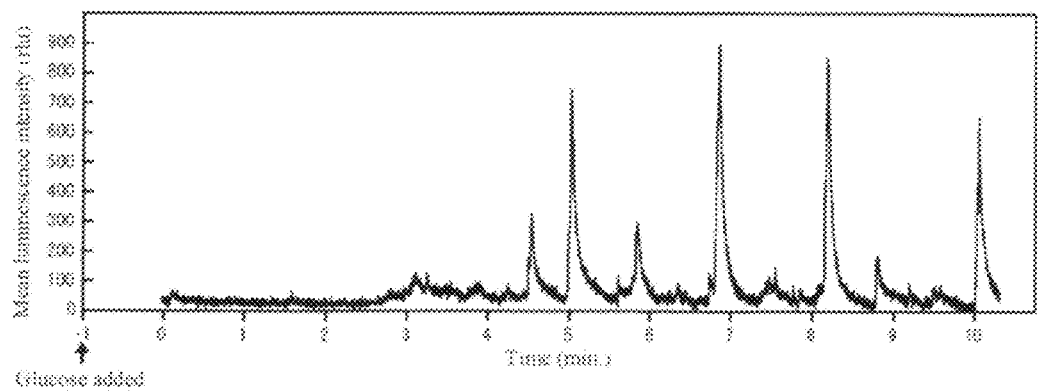
FIG. 6 shows the graphs formed by quantifying time-lapse changes of the insulin-GLase fusion protein secreted in a periodic pulsatile manner by stimulation of glucose added, in the image regions of FIG. 5, from the mean luminescence intensity.

In some other experiments, the cells associated with the close interaction between cells had a tendency to show pulsatile insulin secretion, as compared to the cells in the peripheral region of cell clusters (FIG. 5, FIG. 6).

In addition, the crowd of strong luminescent spots generated by secretion of the insulin-GLase fusion protein inside the cells was concentrated at a depth within 1 µm from the bottom of cell bodies. These data suggest that insulin secretion would be dependent on cell adhesion. These data also suggest that the formation of cell clusters which interact between cells would be important in a periodic secretion of insulin under physiological conditions.

Figure 7:
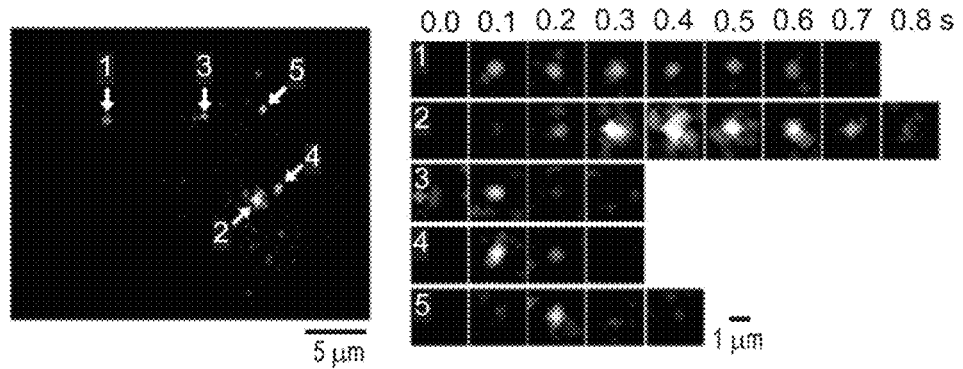
FIG. 7 shows the distribution of the insulin-GLase fusion protein by exocytosis, not secreted in a periodic pulsatile manner, by stimulation of glucose added to the transformant derived from the MIN6 cell line obtained in EXAMPLE 1-3 and the images showing time-lapse changes of the luminescence signal at each luminescence spot for a short period of time (within a second).

In the secretion of the insulin-GLase fusion protein, the sporadic luminescence spots by exocytosis are easy to analyze the size and duration time of luminescence spots generated in a periodic pulsatile manner by secretion of the insulin-GLase fusion protein, as compared to the assembly of sporadic luminescence spots emitted by exocytosis. Many luminescence spots had a size not greater than 1 µm and the duration time of the luminescence spots were between 0.1 and 1 second. These data suggest that luminescence signals by the secretion of each insulin-GLase would be generated by fusion of one cell granule (FIG. 7).

Figure 8:
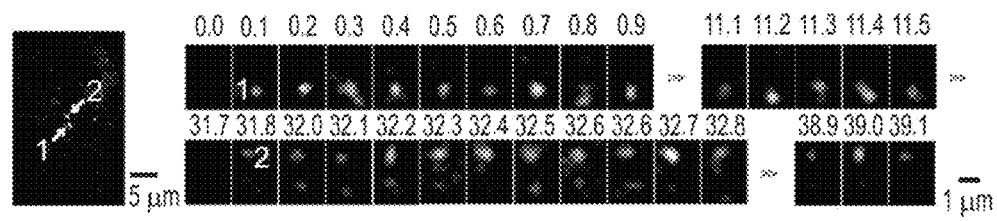
FIG. 8 shows the distribution of the insulin-GLase fusion protein by exocytosis, not secreted in a periodic pulsatile manner, by stimulation of glucose added to the transformant derived from the MIN6 cell line obtained in EXAMPLE 1-3 and the images showing time-lapse changes of the luminescence signal at each luminescence spot for a long period of time (more than a second).

On the other hand, some luminescence signals continued over 1 to 30 seconds. These continuous spots were observed mainly on the bottom side of the cells (FIG. 8). It was first revealed that insulin secretion involved various modes of secretion.

Example 2-1

Figure 9:
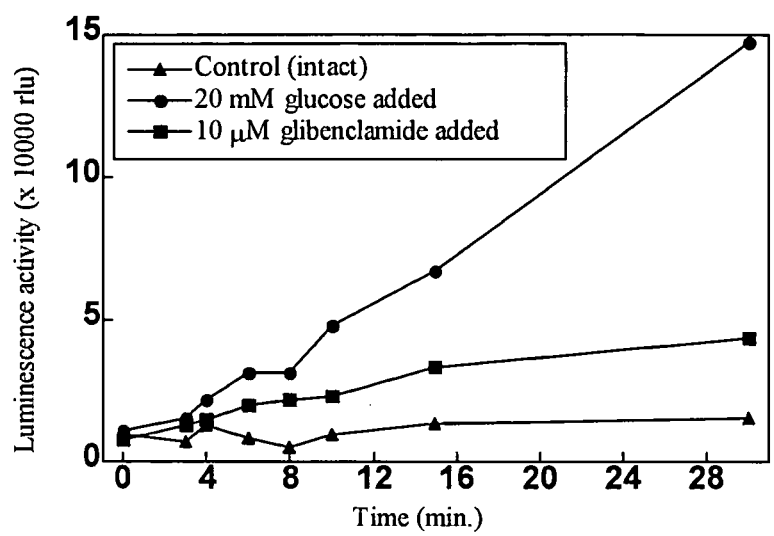
FIG. 9 shows the graphs showing a drug efficacy evaluation of glibenclamide as a hypoglycemic agent using the insulin-GLase-expressed MIN6 cells.

Glibenclamide, which is a sulfonylurea type hypoglycemic agent, promotes the secretion of endogenous insulin to lower blood glucose levels. This promotion of insulin secretion was examined using the insulin-GLase-expressed MIN6 cells to assess the effect. Specifically, the expression vector pcDNA3-hINS-GLuc prepared in EXAMPLE 1-1 was transformed onto MIN6 cells according to the method described in EXAMPLE 1-2 to prepare the insulin-GLase expression cells. After the MIN6 cell line was washed twice with 3 ml of phosphate buffered saline (PBS), 2 ml of low glucose-modified KRHB buffer solution containing 2 mM glucose for control (intact), 20 mM glucose and 10 mM glibenclamide (manufactured by Wako Pure Chemical), respectively, was added and an aliquot of 2 ml was taken every 0, 3, 4, 6, 8, 10, 15 and 30 minutes. The luciferase activity was assayed by the method described in EXAMPLE 1-2. As shown in FIG. 9, it was revealed that insulin secretion was promoted by treating with glibenclamide, indicating that drug efficacy can be assessed in this vector expression cell system.

Embodiment 3-1

Construction of Human Promatrix Metalloproteinase 2 (pro-hMMP-2)-*Gaussia* Luciferase (GLase) Fusion Protein The expression vector pcDNA3-hMMP2-GLuc to express the fusion protein of pro-human matrix metalloproteinase 2 (pro-hMMP-2) having a signal peptide of human matrix metalloproteinase 2 (hMMP-2) and *Gaussia* luciferase (GLase) was constructed as follows.

The coding region of hMMP-2 proprotein was prepared by PCR (cycle conditions: 25 cycles; 15 sec/98° C., 15 sec/55° C., 2 mins/68° C.) using IMAGE cDNA clone 3161383 (cDNA clone prepared by the I.M.A.G.E. consortium). PCR was carried out using KOD-plus-DNA polymerase (manufactured by Toyobo Co., Ltd.) and primer sets of hMMP-2-P1 (5' ggc AAGCTT AGCCACC ATG GAG GCG CTA ATG GCC C 3'; BamHI recognition site underlined) (SEQ ID NO: 23) and hMMP2-P2 (5' ggc GAATTC GCA GCC TAG CCA GTC GGA T 3'; EcoRI recognition site underlined) (SEQ ID NO: 24). The PCR fragment obtained was digested with recognition enzymes BamHI and EcoRI, which was the inserted into the BamHI/EcoRI site of the pcDNA3-GLuc-BE vector (described in FEBS Letters, 581, 4551-4556 (2007)) thereby to construct the expression vector pcDNA3-hMMP2-GLuc. The protein expressed by the expression vector pcDNA3-hMMP2-GLuc obtained is the fusion protein composed of the signal peptide sequence of hMMP-2, hMMP-2 and GLase.

Embodiment 3-2

Preparation of Transformant Using Expression Vector pcDNA3-hMMP2-GLuc

HeLa cells, which is the cell line derived from human uterine cervix carcinoma, were cultured in DMEM medium (manufactured by Sigma) supplemented with 10% fetal calf serum (manufactured by Invitrogen).

The HeLa cell line was transfected by the expression vector pcDNA3-hMMP2-GLuc obtained in EMBODIMENT 3-1, using Fugene HD (manufactured by Roche). After the transfection, the cells were cultured at 37° C. for 24 hours in a $CO_2$ incubator.

Embodiment 3-3

Imaging of Extracellular Secretion of the Human Metalloproteinase 2 (hMMP-2)-GLase Fusion Protein The fusion protein was cultured in a 35 mm uncoated glass-bottom culture dish (manufactured by Asahi Glass Co., Ltd.) and imaging of extracellular secretion of the human metalloproteinase 2 (hMMP-2)-GLase fusion protein was performed in a manner similar to EXAMPLE 1-3 described above.

Figure 10:
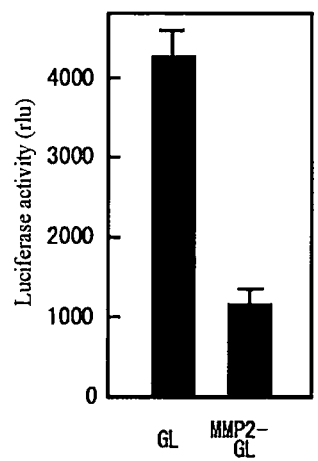
FIG. 10 shows the graph comparing the activities of the hMMP-2-GLase fusion protein (MMP2-GL) secreted from the transformant derived from the HeLa cell line obtained in EMBODIMENT 3-2 and FIG. 11 shows the luminescence images showing the distribution of the hMMP-2-GLase fusion protein secreted from the transformant derived from the HeLa cell line obtained in EMBODIMENT 3-2 in cell membrane. Left, bright-field image, center: luminescence signal image, right: image superimposed on the bright-field image.

When GLase fused to hMMP-2 (hMMP-2-GLase fusion protein) was transiently expressed in HeLa cells for 24 hours, MMP-2-GLase in the medium showed about ⅓ luminescence intensity, as compared to that of GLase alone (FIG. 10). The HeLa cells transiently expressing the hMMP-2-GLase fusion protein and wild type hMMP-2 were analyzed by the immunofluorescence technique and the western blot technique, using anti-MMP-2 antibody and anti-GLase antibody. The hMMP-2-GLase fusion protein showed the localization as in wild type hMMP-2. These results demonstrate that the secretion pathway of hMMP-2-GLase is the same as in wild type hMMP-2.

Figure 11:
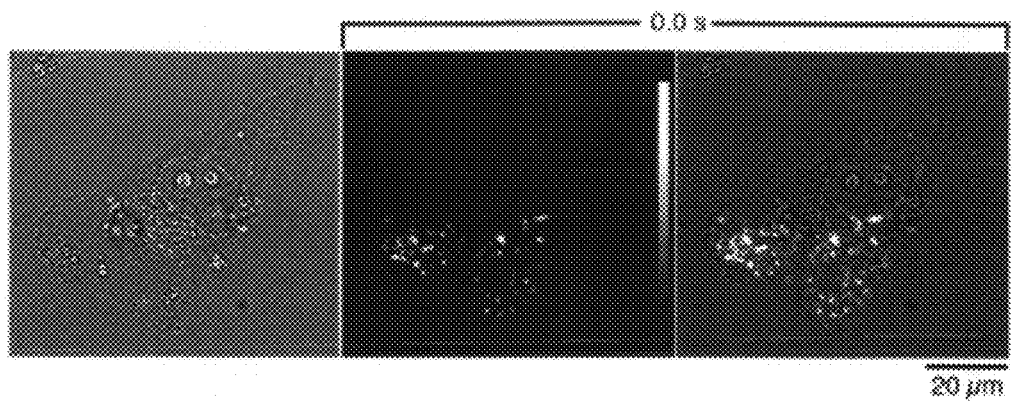

On the other hand, the analysis of luminescence video images (500 msec/frame) in the transformed HeLa cells expressing the hMMP-2-GLase fusion protein demonstrated that the MMP-2 secretion showed cell polarity (FIG. 11). In the HeLa cells expressing the hMMP-2-GLase fusion protein, many bright luminescence spots were observed in the luminescence images immediately after addition of coelenterazine as a luminescent substrate, unlike the HeLa cells expressed by GLase alone. These luminescence spots first appeared stayed on the same place and then slowly diminished to the background level within a minute after addition of coelenterazine. By contrast, the presence of luminescence spots that maintained their luminescence indicates the hMMP-2-GLase fusion protein bound to the cell membrane surface. These continuing luminescence spots move toward the front of a migrating cell to give an uneven distribution. MMP-2 is known to bind integrin or MT1-MMP (MMP14) (this is an activator of MMP-2) on the cell surface. These continuing luminescence spots of the MMP-2-GLase fusion protein show the localization of MMP-2 on the cell surface, bound to the protein described above.

Figure 12:
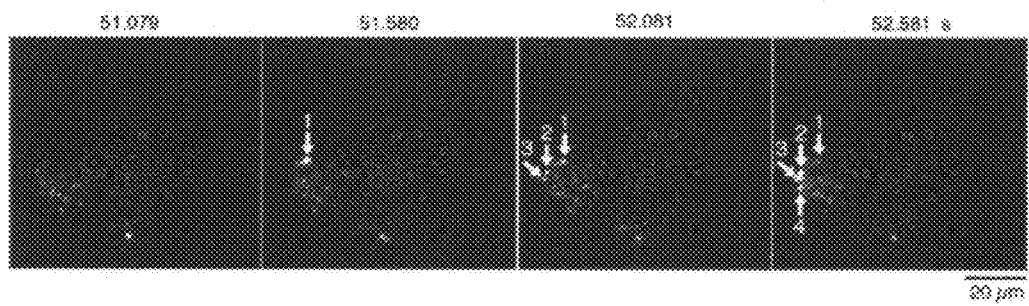
FIG. 12 shows the luminescence images showing the time-lapse distribution of the hMMP-2-GLase fusion protein from the transformant derived from the HeLa cell line obtained in EMBODIMENT 3-2 in cell membrane.

The luminescence spots showing exocytosis of the hMMP-2-GLase fusion protein, which transiently appeared, were observed until or after the continuing luminescence spots disappeared. Under the same imaging conditions (500 msec/frame, 40× objective lens; FIG. 12), the luminescence spots of hMMP-2-GLase transiently appeared were maintained in narrow regions and slowly diffused over a few seconds, unlike the luminescence spots of non-fused GLase alone.

Figure 13:
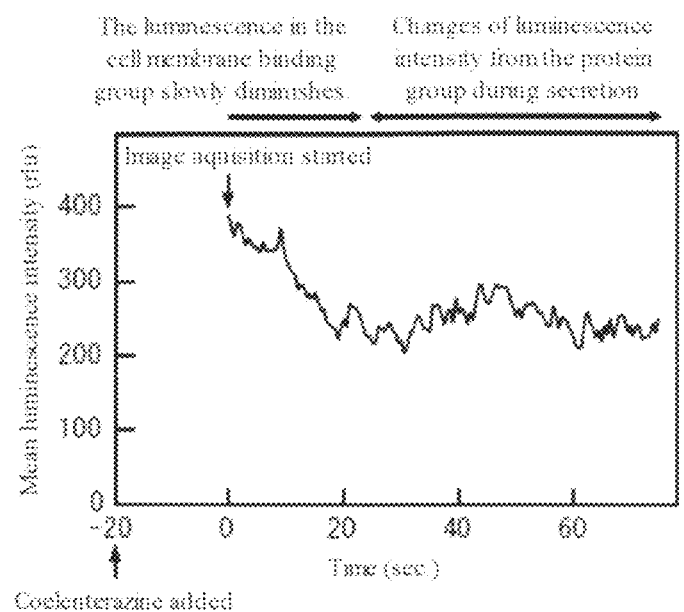
FIG. 13 shows the graph showing changes of the mean luminescence intensity of the hMMP-2-GLase fusion protein from the transformant derived from the HeLa cell line obtained in EXAMPLE 3-2, with the lapse of time.
Figure 14:
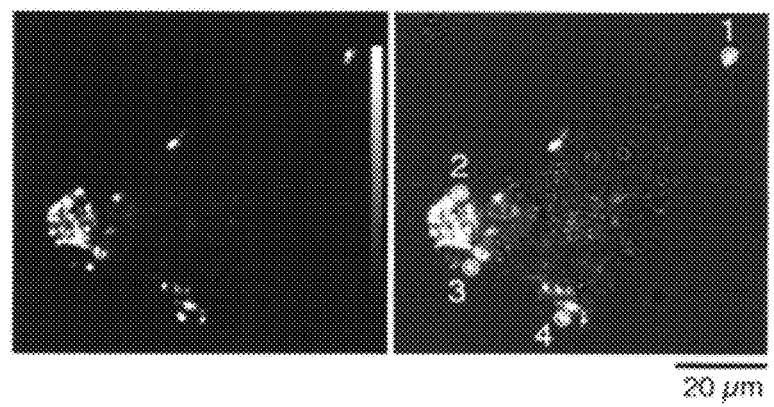
FIG. 14 shows the luminescence images of the hMMP-2-GLase fusion protein from the transformant derived from the HeLa cell line obtained in Example 3-2 in cell membrane. Left: luminescence signal image, right: image superimposed on the bright-field image.

The luminescence spots by secretion of the hMMP-2-GLase fusion protein emerged chiefly around the leading edge of the cells. Successive secretion of the hMMP-2-GLase fusion protein over a few seconds was sometimes observed along the leading edge (FIG. 12). The MMP-2 protease activity may be required to degrade cell adhesion protein and lift up ruffling membranes, and successive secretion of hMMP-2-GLase may be associated with the formation and migration of ruffling membranes at the leading edge. The luminescence signals by hMMP-2-GLase secretion were not stimulated by increased $K^+$ concentrations and clearly were not affected by intracellular ions After the continuous secretory luminescence disappeared (FIG. 13), the maximum luminescence signals (FIG. 14, left) generated from exocytosis of the hMMP-2-GLase fusion protein were superimposed on the bright-field image to produce the composite image (100 frames for about 50 secs.; FIG. 14, right). Localization and frequency of exocytosis phenomenon of the hMMP-2-GLase fusion protein were estimated. This composite image clearly indicates that MMP-2 shows a polar distribution around the leading edge of a migrating cell. The distribution of luminescence spots by the exocytosis was closer to the leading edge, as compared to the distribution of continuing luminescence spots observed at an early stage (FIG. 14). The luminescence video images and composite image (FIG. 14, right) also shows the secretion of the hMMP-2-GLase fusion protein from a migrating cell. These data suggest that hot spots of MMP-2 secretion by the exocytosis phenomenon and punctate spots of MMP-2 remained on the cell surface are localized on the discrete minimal region of plasma membrane.

Figure 15:
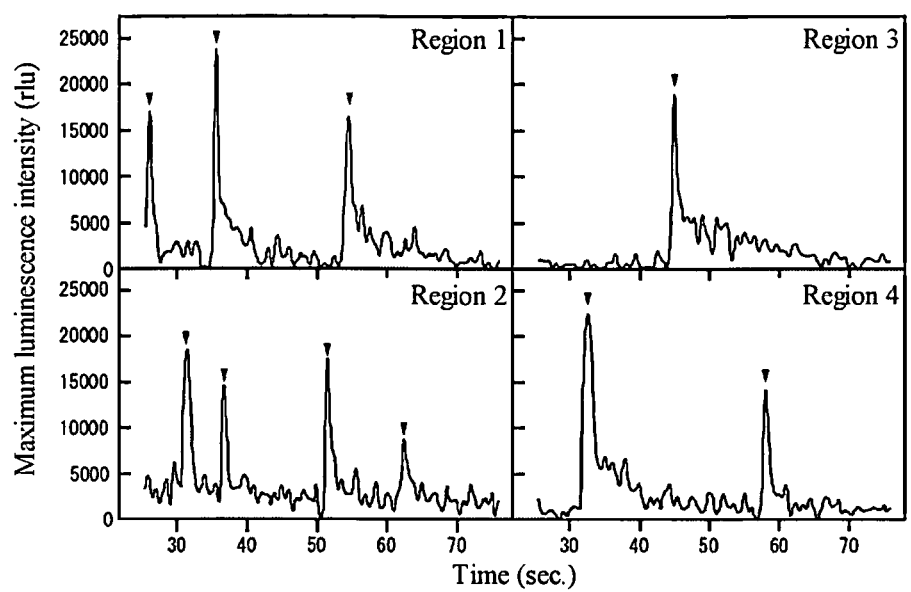
FIG. 15 is graphs formed by quantifying time-lapse changes of the hMMP-2-GLase fusion protein in the luminescence spot regions 1 to 4 designated in FIG. 14, wherein the arrow designates potent secretory luminescence signals.

Next, the frequency of exocytosis in the minimal region of cells was estimated. In FIG. 13, the composite image of the maximum luminescence intensity in the four regions circled in the composite image in FIG. 13 showed several luminescence peaks in each region (FIG. 15). The marked luminescence peaks (designated by the arrow in FIG. 14) in the regions 1 to 4 were measured and found to be 3, 4, 1 and 2, respectively. These numbers represent the number of marked exocytosis that occurred at least during this period (100 frames, about 50 seconds). These data indicate that the exocytosis of the hMMP-2-GLase fusion protein is repeated in the limited minimal region on the cell surface of a migrating cell.

Figure 16:
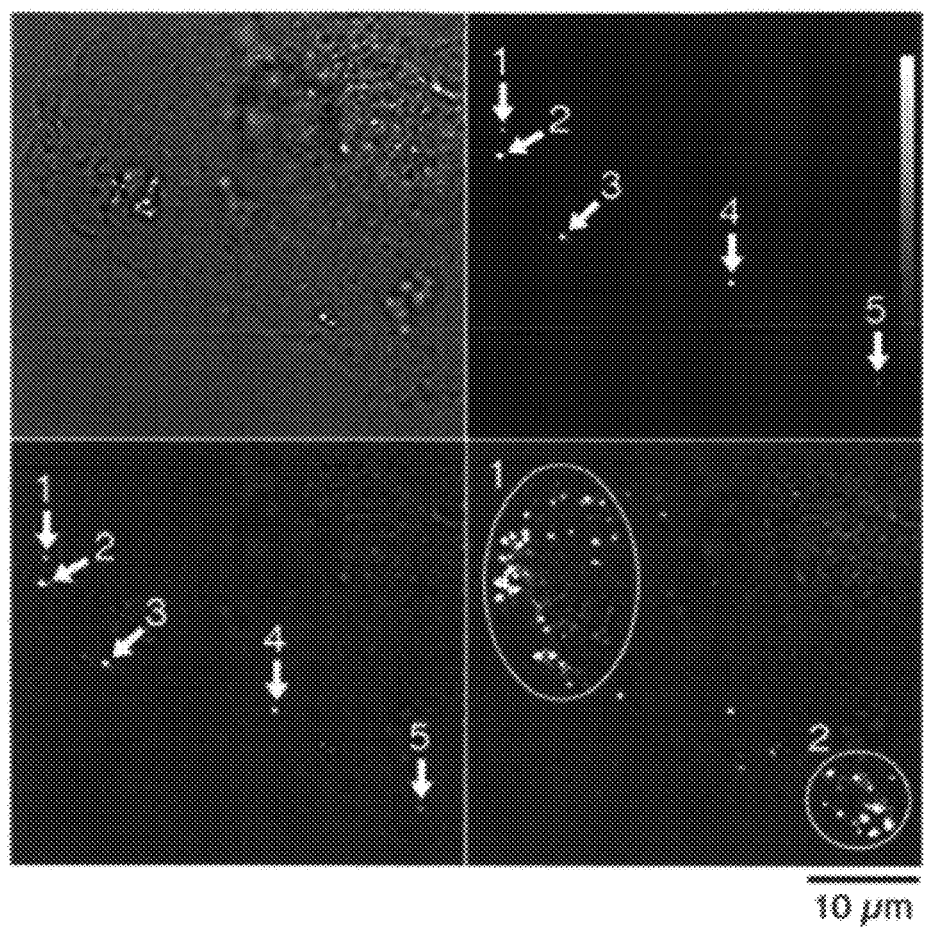
FIG. 16 shows the luminescence images of the hMMP-2-GLase fusion protein from the transformant derived from the HeLa cell line obtained in Example 3-2, at the leading edge. Upper left: bright-field images, upper right: luminescence signal images, lower left: luminescence images superimposed on the bright-field images, lower right: images showing the luminescence spot region at the leading edge appeared for 100 seconds.
Figure 17:
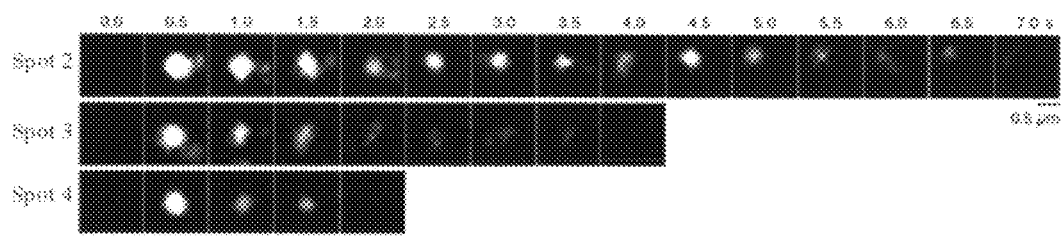
FIG. 17 shows time-lapse changes of the luminescence images of the hMMP-2-GLase fusion protein in the luminescence spots 2, 3 and 4 designated in FIG. 16.

Next, imaging was performed using a 100× objective lens (number of aperture NA, 1.45). Immediately after acquisition of the luminescence video images using a 40× objective lens, the luminescence video images associated with hMMP-2-GLase of the same migrating cell were acquired at 500 ms/frame (200 frames for about 100 seconds). The luminescence spots by each secretion of the hMMP-2-GLase fusion protein at the leading edge were more clearly observed from the luminescence images acquired using a high 100× objective lens. The luminescence spots (FIG. 16, spots 1 to 6) of the luminescence video images in one frame designated by the arrows were determined to be the signals generated by the exocytosis phenomenon, based on the images. The spots 2 to 4 newly emerged in this frame. In spots 2 and 3, the luminescence intensity of the luminescence spots by exocytosis diminished to the background level in 2 to 3 seconds (FIG. 17). Some luminescence spots such as spot 2 which repeatedly appeared suggest hMMP-2 secretion due to continuous membrane fusion of exocytotic secretory granules (FIG. 17).

Most of the luminescence spots from the hMMP-2-GLase fusion protein are less than 1 μm, like these spots. The diameter of the luminescence spot from one exocytotic granule was measured to be 0.1 to 0.4 μm by TIRF and the two-photon imaging method (Science, 297, 1349-1352 (2002)). Accordingly, these luminescence spots are generated either by secretion of MMP-2-GLase fusion protein derived from one exocytic secretory granule or by continuous fusion of secretory vesicles in the minimal region. In the composite image of the maximum luminescence intensity in the video images, distribution of the exocytosis spots at the leading edge can be analyzed with a high resolution. The number of the luminescence spots transiently appeared in the region 1 and region 2 was calculated to be 70 and 20, respectively (FIG. 16, lower right).

The luminescence spots by secretion of the hMMP-2-GLase fusion protein were concentrated at a depth within 1 μm from the bottom side of cells. This suggests that hMMP-2 would be secreted mainly from the bottom side of the cell surface.

These data suggest that the fusion of exocytotic secretory granules including MMP-2 would take place at the leading edge for a short period of time to disrupt cell adhesion and extracellular matrix.

INDUSTRIAL APPLICABILITY

The screening method of the present invention is useful for screening drugs such as insulin secretagogues having an insulin secretagogue activity with minimized side effects (hypoglycemia induction, etc.). The transformant in which a polynucleotide encoding the fusion protein used for the screening method is introduced, the screening kit comprising the transformant, etc. are also useful for screening excellent drugs.

BRIEF DESCRIPTION OF THE SEQUENCES

SEQ ED NO: 1 Nucleotide sequence of the polynucleotide encoding Gaussia luciferase (GLase)
SEQ ID NO: 2 Amino acid sequence of Gaussia luciferase
SEQ ID NO: 3 Nucleotide sequence of the polynucleotide encoding human proinsulin
SEQ ID NO: 4 Amino acid sequence of human proinsulin
SEQ ID NO: 5 Nucleotide sequence of the polynucleotide encoding the signal peptide of human preproinsulin
SEQ ID NO: 6 Amino acid sequence of the signal peptide of human preproinsulin SEQ ID NO: 7 Nucleotide sequence of the polynucleotide encoding Gaussia luciferase (GLase (K18-D185)) lacking the signal sequence, used in Example 1-1 and EMBODIMENT 3-1
SEQ ID NO: 8 Amino acid sequence of the polypeptide (GLase (K18-D185)) encoded by the polynucleotide consisting of the nucleotide sequence represented by SEQ ID NO: 7
SEQ ID NO: 9 Nucleotide sequence of the polynucleotide encoding human preproinsulin used in EXAMPLE 1-1
SEQ ID NO: 10 Amino acid sequence of the polypeptide (human preproinsulin) encoded by the polynucleotide consisting of the nucleotide sequence represented by SEQ ID NO: 9
SEQ ID NO: 11 Nucleotide sequence of the polynucleotide encoding the fusion protein of human preproinsulin and Gaussia luciferase (GLase (K18-D185)) lacking the signal sequence, used in EXAMPLE 1-1
SEQ ID NO: 12 Amino acid sequence of the polypeptide encoded by the polynucleotide consisting of the nucleotide sequence represented by SEQ ID NO: 11
SEQ ID NO: 13 Nucleotide sequence of the polynucleotide encoding human MMP-2
SEQ ID NO: 14 Amino acid sequence of human MMP-2
SEQ ID NO: 15 Nucleotide sequence of the polynucleotide encoding the signal sequence of human pro-MMP-2
SEQ ID NO: 16 Amino acid sequence of the signal sequence of human pro-MMP-2
SEQ ID NO: 17 Nucleotide sequence of the polynucleotide encoding human pro-MMP-2 used in EMBODIMENT 3-1
SEQ ID NO: 18 Amino acid sequence of the polypeptide (human pro-MMP-2) encoded by the polynucleotide represented by SEQ ID NO: 17
SEQ ID NO: 19 Nucleotide sequence of the polynucleotide encoding the fusion protein of human pro-MMP-2 and Gaussia luciferase (GLase (K18-D185)) lacking the signal sequence, used in EMBODIMENT 3-1
SEQ ID NO: 20 Amino acid sequence of the polypeptide encoded by the polynucleotide represented by SEQ ID NO: 19
SEQ ID NO: 21 Nucleotide sequence of the primer used in EXAMPLE 1-1
SEQ ID NO: 22 Nucleotide sequence of the primer used in EXAMPLE 1-1
SEQ ID NO: 23 Nucleotide sequence of the primer used in EMBODIMENT 3-1
SEQ ID NO: 24 Nucleotide sequence of the primer used in EMBODIMENT 3-1

The invention claimed is:

1. A method of screening a substance regulating insulin secretion from a cell, which comprises:
   contacting a cell transformed with a polynucleotide encoding a fusion protein of preproinsulin and a luciferase with a test substance, and
   detecting luminescence of the luciferase to measure a level of insulin secretion,
   wherein the luciferase is *Gaussia* luciferase, and
   wherein *Gaussia* luciferase is a protein of any one of (a) through (c) below:
   (a) a protein comprising the amino acid sequence of SEQ ID NO: 8;
   (b) a protein consisting of an amino acid sequence comprising deletion, substitution, insertion and/or addition of 1 to 10 amino acid residues in the amino acid sequence of SEQ ID NO: 8, and having substantially the same activity as a protein consisting of the amino acid sequence of SEQ ID NO: 8;
   (c) a protein consisting of an amino acid sequence having at least 90% identity to the amino acid sequence of SEQ ID NO: 8, and having substantially the same activity as the protein consisting of the amino acid sequence of SEQ ID NO: 8; and,
   wherein the preproinsulin consists of a signal peptide of preproinsulin and the polypeptide of any one of (i) through (k) below:
   (i) a polypeptide consisting of the amino acid sequence of SEQ ID NO: 4;
   (j) a polypeptide comprising a polypeptide consisting of an amino acid sequence comprising deletion, substitution, insertion and/or addition of 1 to 10 amino acid residues in the amino acid sequence of SEQ ID NO: 4, and having an insulin activity;
   (k) a polypeptide comprising a polypeptide consisting of an amino acid sequence having at least 90% identity to the amino acid sequence of SEQ ID NO: 4, and having an insulin activity; and,
   wherein the signal peptide of preproinsulin is a polypeptide consisting of the amino acid sequence of SEQ ID NO: 6.

2. The screening method according to claim 1, wherein the any one of (e) through (g) below:
   (e) a polypeptide consisting of the amino acid sequence of SEQ ID NO: 10;
   (f) a polypeptide comprising a polypeptide consisting of an amino acid sequence comprising deletion, substitution, insertion and/or addition of 1 to 10 amino acid residues in the amino acid sequence of SEQ ID NO: 10, and having an insulin activity;
   (g) a polypeptide comprising a polypeptide consisting of an amino acid sequence having at least 90% identity to the amino acid sequence of SEQ ID NO: 10, and having an insulin activity; and,
   (h) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 9 wherein the high stringent conditions are 5×SSC, 5×Denhardt's solution, 0.5% (w/v) SDS, 50% (v/v) formamide and 50° C., and having an insulin activity.

3. The screening method according to claim 1, wherein the fusion any one of (m) through (o) below:
- (m) a polypeptide consisting of the amino acid sequence of SEQ ID NO: 12;
- (n) a polypeptide comprising a polypeptide consisting of an amino acid sequence comprising deletion, substitution, insertion and/or addition of 1 to 10 amino acid residues in the amino acid sequence of SEQ ID NO: 12, and having an insulin activity;
- (o) a polypeptide comprising a polypeptide consisting of an amino acid sequence having at least 90% identity to the amino acid sequence of SEQ ID NO: 12, and having an insulin activity; and,
- (p) a polypeptide comprising a polypeptide consisting of an amino acid sequence encoded by a polynucleotide that hybridizes under high stringent conditions to a polynucleotide consisting of a nucleotide sequence complementary to the nucleotide sequence of SEQ ID NO: 11 wherein the high stringent conditions are 5×SSC, 5×Denhardt's solution, 0.5% (w/v) SDS, 50% (v/v) formamide and 50° C., and having an insulin activity.

4. The screening method according to claim 1, which further comprises the step of detecting luminescence using a CCD camera or a photon counting camera.

5. A method of screening a substance regulating insulin secretion from a cell, which comprises:
  contacting a cell transformed with a polynucleotide encoding a fusion protein of preproinsulin and a luciferase with a test substance, and
  detecting luminescence of the luciferase to measure a level of insulin secretion, wherein the luciferase is *Gaussia* luciferase, and
wherein *Gaussia* luciferase is a protein of any one of (a) through (c) below:
- (a) a protein consisting of the amino acid sequence of SEQ ID NO: 8;
- (b) a protein consisting of an amino acid sequence comprising deletion, substitution, insertion and/or addition of 1 to 5 amino acid residues in the amino acid sequence of SEQ ID NO: 8, and having substantially the same activity as a protein consisting of the amino acid sequence of SEQ ID NO: 8;
- (c) a protein consisting of an amino acid sequence having at least 90% identity to the amino acid sequence of SEQ ID NO: 8, and having substantially the same activity as the protein consisting of the amino acid sequence of SEQ ID NO: 8; and, wherein the preproinsulin consists of a signal peptide of preproinsulin and the polypeptide of any one of (i) through (k) below:
- (i) a polypeptide consisting of the amino acid sequence of SEQ ID NO: 4;
- (j) a polypeptide comprising a polypeptide consisting of an amino acid sequence comprising deletion, substitution, insertion and/or addition of 1 to 10 amino acid residues in the amino acid sequence of SEQ ID NO: 4, and having an insulin activity;
- (k) a polypeptide comprising a polypeptide consisting of an amino acid sequence having at least 90% identity to the amino acid sequence of SEQ ID NO: 4, and having an insulin activity; and, wherein the signal peptide of preproinsulin is a polypeptide consisting of the amino acid sequence of SEQ ID NO: 6.

* * * * *

SEQUENCE LISTING

<160> NUMBER OF SEQ ID NOS: 24

<210> SEQ ID NO 1
<211> LENGTH: 555
<212> TYPE: DNA
<213> ORGANISM: Gaussia princeps
<220> FEATURE:
<221> NAME/KEY: CDS
<222> LOCATION: (1)..(555)

<400> SEQUENCE: 1

| | | | | | | | | | | | | | | | | |
|---|---|---|---|---|---|---|---|---|---|---|---|---|---|---|---|---|
| atg | gga | gtc | aaa | gtt | ctg | ttt | gcc | ctg | atc | tgc | atc | gct | gtg | gcc | gag | 48 |
| Met | Gly | Val | Lys | Val | Leu | Phe | Ala | Leu | Ile | Cys | Ile | Ala | Val | Ala | Glu | |
| 1 | | | | 5 | | | | | 10 | | | | | 15 | | |

| gcc | aag | ccc | acc | gag | aac | aac | gaa | gac | ttc | aac | atc | gtg | gcc | gtg | gcc | 96 |
|---|---|---|---|---|---|---|---|---|---|---|---|---|---|---|---|---|
| Ala | Lys | Pro | Thr | Glu | Asn | Asn | Glu | Asp | Phe | Asn | Ile | Val | Ala | Val | Ala | |
| | | | 20 | | | | | 25 | | | | | 30 | | | |

| agc | aac | ttc | gcg | acc | acg | gat | ctc | gat | gct | gac | cgc | ggg | aag | ttg | ccc | 144 |
|---|---|---|---|---|---|---|---|---|---|---|---|---|---|---|---|---|
| Ser | Asn | Phe | Ala | Thr | Thr | Asp | Leu | Asp | Ala | Asp | Arg | Gly | Lys | Leu | Pro | |
| | | 35 | | | | | 40 | | | | | 45 | | | | |

| ggc | aag | aag | ctg | ccg | ctg | gag | gtg | ctc | aaa | gag | atg | gaa | gcc | aat | gcc | 192 |
|---|---|---|---|---|---|---|---|---|---|---|---|---|---|---|---|---|
| Gly | Lys | Lys | Leu | Pro | Leu | Glu | Val | Leu | Lys | Glu | Met | Glu | Ala | Asn | Ala | |
| 50 | | | | | 55 | | | | | 60 | | | | | | |

| cgg | aaa | gct | ggc | tgc | acc | agg | ggc | tgt | ctg | atc | tgc | ctg | tcc | cac | atc | 240 |
|---|---|---|---|---|---|---|---|---|---|---|---|---|---|---|---|---|
| Arg | Lys | Ala | Gly | Cys | Thr | Arg | Gly | Cys | Leu | Ile | Cys | Leu | Ser | His | Ile | |
| 65 | | | | 70 | | | | | 75 | | | | | 80 | | |

| aag | tgc | acg | ccc | aag | atg | aag | aag | ttc | atc | cca | gga | cgc | tgc | cac | acc | 288 |
|---|---|---|---|---|---|---|---|---|---|---|---|---|---|---|---|---|
| Lys | Cys | Thr | Pro | Lys | Met | Lys | Lys | Phe | Ile | Pro | Gly | Arg | Cys | His | Thr | |
| | | | | 85 | | | | | 90 | | | | | 95 | | |

| tac | gaa | ggc | gac | aaa | gag | tcc | gca | cag | ggc | ggc | ata | ggc | gag | gcg | atc | 336 |
|---|---|---|---|---|---|---|---|---|---|---|---|---|---|---|---|---|
| Tyr | Glu | Gly | Asp | Lys | Glu | Ser | Ala | Gln | Gly | Gly | Ile | Gly | Glu | Ala | Ile | |
| | | | 100 | | | | | 105 | | | | | 110 | | | |

| gtc | gac | att | cct | gag | att | cct | ggg | ttc | aag | gac | ttg | gag | ccc | atg | gag | 384 |
|---|---|---|---|---|---|---|---|---|---|---|---|---|---|---|---|---|
| Val | Asp | Ile | Pro | Glu | Ile | Pro | Gly | Phe | Lys | Asp | Leu | Glu | Pro | Met | Glu | |
| | | 115 | | | | | 120 | | | | | 125 | | | | |

| cag | ttc | atc | gca | cag | gtc | gat | ctg | tgt | gtg | gac | tgc | aca | act | ggc | tgc | 432 |
|---|---|---|---|---|---|---|---|---|---|---|---|---|---|---|---|---|
| Gln | Phe | Ile | Ala | Gln | Val | Asp | Leu | Cys | Val | Asp | Cys | Thr | Thr | Gly | Cys | |
| | 130 | | | | | 135 | | | | | 140 | | | | | |

| ctc | aaa | ggg | ctt | gcc | aac | gtg | cag | tgt | tct | gac | ctg | ctc | aag | aag | tgg | 480 |
|---|---|---|---|---|---|---|---|---|---|---|---|---|---|---|---|---|
| Leu | Lys | Gly | Leu | Ala | Asn | Val | Gln | Cys | Ser | Asp | Leu | Leu | Lys | Lys | Trp | |
| 145 | | | | 150 | | | | | 155 | | | | | 160 | | |

| ctg | ccg | caa | cgc | tgt | gcg | acc | ttt | gcc | agc | aag | atc | cag | ggc | cag | gtg | 528 |
|---|---|---|---|---|---|---|---|---|---|---|---|---|---|---|---|---|
| Leu | Pro | Gln | Arg | Cys | Ala | Thr | Phe | Ala | Ser | Lys | Ile | Gln | Gly | Gln | Val | |
| | | | 165 | | | | | 170 | | | | | 175 | | | |

| gac | aag | atc | aag | ggg | gcc | ggt | ggt | gac | | | | | | | | 555 |
|---|---|---|---|---|---|---|---|---|---|---|---|---|---|---|---|---|
| Asp | Lys | Ile | Lys | Gly | Ala | Gly | Gly | Asp | | | | | | | | |
| | | | 180 | | | | | 185 | | | | | | | | |

<210> SEQ ID NO 2
<211> LENGTH: 185
<212> TYPE: PRT
<213> ORGANISM: Gaussia princeps

<400> SEQUENCE: 2

Met Gly Val Lys Val Leu Phe Ala Leu Ile Cys Ile Ala Val Ala Glu
1               5                   10                  15

Ala Lys Pro Thr Glu Asn Asn Glu Asp Phe Asn Ile Val Ala Val Ala
                20                  25                  30

Ser Asn Phe Ala Thr Thr Asp Leu Asp Ala Asp Arg Gly Lys Leu Pro
            35                  40                  45

```
Gly Lys Lys Leu Pro Leu Glu Val Leu Lys Glu Met Glu Ala Asn Ala
        50                  55                  60

Arg Lys Ala Gly Cys Thr Arg Gly Cys Leu Ile Cys Leu Ser His Ile
 65                  70                  75                  80

Lys Cys Thr Pro Lys Met Lys Lys Phe Ile Pro Gly Arg Cys His Thr
                85                  90                  95

Tyr Glu Gly Asp Lys Glu Ser Ala Gln Gly Gly Ile Gly Glu Ala Ile
                100                 105                 110

Val Asp Ile Pro Glu Ile Pro Gly Phe Lys Asp Leu Glu Pro Met Glu
                115                 120                 125

Gln Phe Ile Ala Gln Val Asp Leu Cys Val Asp Cys Thr Thr Gly Cys
        130                 135                 140

Leu Lys Gly Leu Ala Asn Val Gln Cys Ser Asp Leu Leu Lys Lys Trp
145                 150                 155                 160

Leu Pro Gln Arg Cys Ala Thr Phe Ala Ser Lys Ile Gln Gly Gln Val
                165                 170                 175

Asp Lys Ile Lys Gly Ala Gly Gly Asp
                180                 185

<210> SEQ ID NO 3
<211> LENGTH: 258
<212> TYPE: DNA
<213> ORGANISM: Homo sapiens
<220> FEATURE:
<221> NAME/KEY: CDS
<222> LOCATION: (1)..(258)

<400> SEQUENCE: 3 ttt gtg aac caa cac ctg tgc ggc tca cac ctg gtg gaa gct ctc tac       48
Phe Val Asn Gln His Leu Cys Gly Ser His Leu Val Glu Ala Leu Tyr
 1               5                  10                  15 cta gtg tgc ggg gaa cga ggc ttc ttc tac aca ccc aag acc cgc cgg       96
Leu Val Cys Gly Glu Arg Gly Phe Phe Tyr Thr Pro Lys Thr Arg Arg
                20                  25                  30 gag gca gag gac ctg cag gtg ggg cag gtg gag ctg ggc ggg ggc cct      144
Glu Ala Glu Asp Leu Gln Val Gly Gln Val Glu Leu Gly Gly Gly Pro
            35                  40                  45 ggt gca ggc agc ctg cag ccc ttg gcc ctg gag ggg tcc ctg cag aag      192
Gly Ala Gly Ser Leu Gln Pro Leu Ala Leu Glu Gly Ser Leu Gln Lys
 50                  55                  60 cgt ggc att gtg gaa caa tgc tgt acc agc atc tgc tcc ctc tac cag      240
Arg Gly Ile Val Glu Gln Cys Cys Thr Ser Ile Cys Ser Leu Tyr Gln
 65                  70                  75                  80 ctg gag aac tac tgc aac                                              258
Leu Glu Asn Tyr Cys Asn
                85

<210> SEQ ID NO 4
<211> LENGTH: 86
<212> TYPE: PRT
<213> ORGANISM: Homo sapiens

<400> SEQUENCE: 4

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
                20                  25                  30

Glu Ala Glu Asp Leu Gln Val Gly Gln Val Glu Leu Gly Gly Gly Pro
            35                  40                  45
```

```
Gly Ala Gly Ser Leu Gln Pro Leu Ala Leu Glu Gly Ser Leu Gln Lys
 50                  55                  60

Arg Gly Ile Val Glu Gln Cys Cys Thr Ser Ile Cys Ser Leu Tyr Gln
 65                  70                  75                  80

Leu Glu Asn Tyr Cys Asn
                 85

<210> SEQ ID NO 5
<211> LENGTH: 72
<212> TYPE: DNA
<213> ORGANISM: Homo sapiens
<220> FEATURE:
<221> NAME/KEY: CDS
<222> LOCATION: (1)..(72)

<400> SEQUENCE: 5 atg gcc ctg tgg atg cgc ctc ctg ccc ctg ctg gcg ctg ctg gcc ctc    48
Met Ala Leu Trp Met Arg Leu Leu Pro Leu Leu Ala Leu Leu Ala Leu
 1               5                  10                  15 tgg gga cct gac cca gcc gca gcc                                    72
Trp Gly Pro Asp Pro Ala Ala Ala
             20

<210> SEQ ID NO 6
<211> LENGTH: 24
<212> TYPE: PRT
<213> ORGANISM: Homo sapiens

<400> SEQUENCE: 6

Met Ala Leu Trp Met Arg Leu Leu Pro Leu Leu Ala Leu Leu Ala Leu
 1               5                  10                  15

Trp Gly Pro Asp Pro Ala Ala Ala
             20

<210> SEQ ID NO 7
<211> LENGTH: 504
<212> TYPE: DNA
<213> ORGANISM: Gaussia princeps
<220> FEATURE:
<221> NAME/KEY: CDS
<222> LOCATION: (1)..(504)

<400> SEQUENCE: 7 aag ccc acc gag aac aac gaa gac ttc aac atc gtg gcc gtg gcc agc    48
Lys Pro Thr Glu Asn Asn Glu Asp Phe Asn Ile Val Ala Val Ala Ser
 1               5                  10                  15 aac ttc gcg acc acg gat ctc gat gct gac cgc ggg aag ttg ccc ggc    96
Asn Phe Ala Thr Thr Asp Leu Asp Ala Asp Arg Gly Lys Leu Pro Gly
             20                  25                  30 aag aag ctg ccg ctg gag gtg ctc aaa gag atg gaa gcc aat gcc cgg   144
Lys Lys Leu Pro Leu Glu Val Leu Lys Glu Met Glu Ala Asn Ala Arg
         35                  40                  45 aaa gct ggc tgc acc agg ggc tgt ctg atc tgc ctg tcc cac atc aag   192
Lys Ala Gly Cys Thr Arg Gly Cys Leu Ile Cys Leu Ser His Ile Lys
     50                  55                  60 tgc acg ccc aag atg aag aag ttc atc cca gga cgc tgc cac acc tac   240
Cys Thr Pro Lys Met Lys Lys Phe Ile Pro Gly Arg Cys His Thr Tyr
 65                  70                  75                  80 gaa ggc gac aaa gag tcc gca cag ggc ggc ata ggc gag gcg atc gtc   288
Glu Gly Asp Lys Glu Ser Ala Gln Gly Gly Ile Gly Glu Ala Ile Val
                 85                  90                  95 gac att cct gag att cct ggg ttc aag gac ttg gag ccc atg gag cag   336
Asp Ile Pro Glu Ile Pro Gly Phe Lys Asp Leu Glu Pro Met Glu Gln
```

```
ttc atc gca cag gtc gat ctg tgt gtg gac tgc aca act ggc tgc ctc      384
Phe Ile Ala Gln Val Asp Leu Cys Val Asp Cys Thr Thr Gly Cys Leu
            115                 120                 125 aaa ggg ctt gcc aac gtg cag tgt tct gac ctg ctc aag aag tgg ctg      432
Lys Gly Leu Ala Asn Val Gln Cys Ser Asp Leu Leu Lys Lys Trp Leu
130                 135                 140 ccg caa cgc tgt gcg acc ttt gcc agc aag atc cag ggc cag gtg gac      480
Pro Gln Arg Cys Ala Thr Phe Ala Ser Lys Ile Gln Gly Gln Val Asp
145                 150                 155                 160 aag atc aag ggg gcc ggt ggt gac                                      504
Lys Ile Lys Gly Ala Gly Gly Asp
                165
```

<210> SEQ ID NO 8
<211> LENGTH: 168
<212> TYPE: PRT
<213> ORGANISM: Gaussia princeps

<400> SEQUENCE: 8

```
Lys Pro Thr Glu Asn Asn Glu Asp Phe Asn Ile Val Ala Val Ala Ser
1               5                   10                  15

Asn Phe Ala Thr Thr Asp Leu Asp Ala Asp Arg Gly Lys Leu Pro Gly
                20                  25                  30

Lys Lys Leu Pro Leu Glu Val Leu Lys Glu Met Glu Ala Asn Ala Arg
            35                  40                  45

Lys Ala Gly Cys Thr Arg Gly Cys Leu Ile Cys Leu Ser His Ile Lys
        50                  55                  60

Cys Thr Pro Lys Met Lys Lys Phe Ile Pro Gly Arg Cys His Thr Tyr
65                  70                  75                  80

Glu Gly Asp Lys Glu Ser Ala Gln Gly Gly Ile Gly Glu Ala Ile Val
                85                  90                  95

Asp Ile Pro Glu Ile Pro Gly Phe Lys Asp Leu Glu Pro Met Glu Gln
            100                 105                 110

Phe Ile Ala Gln Val Asp Leu Cys Val Asp Cys Thr Thr Gly Cys Leu
        115                 120                 125

Lys Gly Leu Ala Asn Val Gln Cys Ser Asp Leu Leu Lys Lys Trp Leu
    130                 135                 140

Pro Gln Arg Cys Ala Thr Phe Ala Ser Lys Ile Gln Gly Gln Val Asp
145                 150                 155                 160

Lys Ile Lys Gly Ala Gly Gly Asp
                165
```

<210> SEQ ID NO 9
<211> LENGTH: 330
<212> TYPE: DNA
<213> ORGANISM: Homo sapiens
<220> FEATURE:
<221> NAME/KEY: CDS
<222> LOCATION: (1)..(330)

<400> SEQUENCE: 9

```
atg gcc ctg tgg atg cgc ctc ctg ccc ctg ctg gcg ctg ctg gcc ctc       48
Met Ala Leu Trp Met Arg Leu Leu Pro Leu Leu Ala Leu Leu Ala Leu
1               5                   10                  15 tgg gga cct gac cca gcc gca gcc ttt gtg aac caa cac ctg tgc ggc       96
Trp Gly Pro Asp Pro Ala Ala Ala Phe Val Asn Gln His Leu Cys Gly
                20                  25                  30 tca cac ctg gtg gaa gct ctc tac cta gtg tgc ggg gaa cga ggc ttc      144
```

```
Ser His Leu Val Glu Ala Leu Tyr Leu Val Cys Gly Glu Arg Gly Phe
        35                  40                  45 ttc tac aca ccc aag acc cgc cgg gag gca gag gac ctg cag gtg ggg      192
Phe Tyr Thr Pro Lys Thr Arg Arg Glu Ala Glu Asp Leu Gln Val Gly
    50                  55                  60 cag gtg gag ctg ggc ggg ggc cct ggt gca ggc agc ctg cag ccc ttg      240
Gln Val Glu Leu Gly Gly Gly Pro Gly Ala Gly Ser Leu Gln Pro Leu
65                  70                  75                  80 gcc ctg gag ggg tcc ctg cag aag cgt ggc att gtg gaa caa tgc tgt      288
Ala Leu Glu Gly Ser Leu Gln Lys Arg Gly Ile Val Glu Gln Cys Cys
                85                  90                  95 acc agc atc tgc tcc ctc tac cag ctg gag aac tac tgc aac              330
Thr Ser Ile Cys Ser Leu Tyr Gln Leu Glu Asn Tyr Cys Asn
                100                 105                 110

<210> SEQ ID NO 10
<211> LENGTH: 110
<212> TYPE: PRT
<213> ORGANISM: Homo sapiens

<400> SEQUENCE: 10

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110

<210> SEQ ID NO 11
<211> LENGTH: 840
<212> TYPE: DNA
<213> ORGANISM: Artificial
<220> FEATURE:
<223> OTHER INFORMATION: fusion protein
<220> FEATURE:
<221> NAME/KEY: CDS
<222> LOCATION: (1)..(840)

<400> SEQUENCE: 11 atg gcc ctg tgg atg cgc ctc ctg ccc ctg ctg gcg ctg ctg gcc ctc       48
Met Ala Leu Trp Met Arg Leu Leu Pro Leu Leu Ala Leu Leu Ala Leu
1               5                   10                  15 tgg gga cct gac cca gcc gca gcc ttt gtg aac caa cac ctg tgc ggc       96
Trp Gly Pro Asp Pro Ala Ala Ala Phe Val Asn Gln His Leu Cys Gly
            20                  25                  30 tca cac ctg gtg gaa gct ctc tac cta gtg tgc ggg gaa cga ggc ttc      144
Ser His Leu Val Glu Ala Leu Tyr Leu Val Cys Gly Glu Arg Gly Phe
        35                  40                  45 ttc tac aca ccc aag acc cgc cgg gag gca gag gac ctg cag gtg ggg      192
Phe Tyr Thr Pro Lys Thr Arg Arg Glu Ala Glu Asp Leu Gln Val Gly
    50                  55                  60 cag gtg gag ctg ggc ggg ggc cct ggt gca ggc agc ctg cag ccc ttg      240
Gln Val Glu Leu Gly Gly Gly Pro Gly Ala Gly Ser Leu Gln Pro Leu
```

```
                65                  70                  75                  80
gcc ctg gag ggg tcc ctg cag aag cgt ggc att gtg gaa caa tgc tgt    288
Ala Leu Glu Gly Ser Leu Gln Lys Arg Gly Ile Val Glu Gln Cys Cys
                    85                  90                  95 acc agc atc tgc tcc ctc tac cag ctg gag aac tac tgc aac gaa ttc    336
Thr Ser Ile Cys Ser Leu Tyr Gln Leu Glu Asn Tyr Cys Asn Glu Phe
                100                 105                 110 aag ccc acc gag aac aac gaa gac ttc aac atc gtg gcc gtg gcc agc    384
Lys Pro Thr Glu Asn Asn Glu Asp Phe Asn Ile Val Ala Val Ala Ser
                115                 120                 125 aac ttc gcg acc acg gat ctc gat gct gac cgc ggg aag ttg ccc ggc    432
Asn Phe Ala Thr Thr Asp Leu Asp Ala Asp Arg Gly Lys Leu Pro Gly
    130                 135                 140 aag aag ctg ccg ctg gag gtg ctc aaa gag atg gaa gcc aat gcc cgg    480
Lys Lys Leu Pro Leu Glu Val Leu Lys Glu Met Glu Ala Asn Ala Arg
145                 150                 155                 160 aaa gct ggc tgc acc agg ggc tgt ctg atc tgc ctg tcc cac atc aag    528
Lys Ala Gly Cys Thr Arg Gly Cys Leu Ile Cys Leu Ser His Ile Lys
                165                 170                 175 tgc acg ccc aag atg aag aag ttc atc cca gga cgc tgc cac acc tac    576
Cys Thr Pro Lys Met Lys Lys Phe Ile Pro Gly Arg Cys His Thr Tyr
                180                 185                 190 gaa ggc gac aaa gag tcc gca cag ggc ggc ata ggc gag gcg atc gtc    624
Glu Gly Asp Lys Glu Ser Ala Gln Gly Gly Ile Gly Glu Ala Ile Val
                195                 200                 205 gac att cct gag att cct ggg ttc aag gac ttg gag ccc atg gag cag    672
Asp Ile Pro Glu Ile Pro Gly Phe Lys Asp Leu Glu Pro Met Glu Gln
    210                 215                 220 ttc atc gca cag gtc gat ctg tgt gtg gac tgc aca act ggc tgc ctc    720
Phe Ile Ala Gln Val Asp Leu Cys Val Asp Cys Thr Thr Gly Cys Leu
225                 230                 235                 240 aaa ggg ctt gcc aac gtg cag tgt tct gac ctg ctc aag aag tgg ctg    768
Lys Gly Leu Ala Asn Val Gln Cys Ser Asp Leu Leu Lys Lys Trp Leu
                245                 250                 255 ccg caa cgc tgt gcg acc ttt gcc agc aag atc cag ggc cag gtg gac    816
Pro Gln Arg Cys Ala Thr Phe Ala Ser Lys Ile Gln Gly Gln Val Asp
                260                 265                 270 aag atc aag ggg gcc ggt ggt gac                                    840
Lys Ile Lys Gly Ala Gly Gly Asp
    275                 280

<210> SEQ ID NO 12
<211> LENGTH: 280
<212> TYPE: PRT
<213> ORGANISM: Artificial
<220> FEATURE:
<223> OTHER INFORMATION: Synthetic Construct

<400> SEQUENCE: 12

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
65                  70                  75                  80
```

```
Ala Leu Glu Gly Ser Leu Gln Lys Arg Gly Ile Val Glu Gln Cys
            85                  90                  95

Thr Ser Ile Cys Ser Leu Tyr Gln Leu Glu Asn Tyr Cys Asn Glu Phe
        100                 105                 110

Lys Pro Thr Glu Asn Asn Glu Asp Phe Asn Ile Val Ala Val Ala Ser
    115                 120                 125

Asn Phe Ala Thr Thr Asp Leu Asp Ala Asp Arg Gly Lys Leu Pro Gly
130                 135                 140

Lys Lys Leu Pro Leu Glu Val Leu Lys Glu Met Glu Ala Asn Ala Arg
145                 150                 155                 160

Lys Ala Gly Cys Thr Arg Gly Cys Leu Ile Cys Leu Ser His Ile Lys
                165                 170                 175

Cys Thr Pro Lys Met Lys Lys Phe Ile Pro Gly Arg Cys His Thr Tyr
            180                 185                 190

Glu Gly Asp Lys Glu Ser Ala Gln Gly Gly Ile Gly Glu Ala Ile Val
        195                 200                 205

Asp Ile Pro Glu Ile Pro Gly Phe Lys Asp Leu Glu Pro Met Glu Gln
    210                 215                 220

Phe Ile Ala Gln Val Asp Leu Cys Val Asp Cys Thr Thr Gly Cys Leu
225                 230                 235                 240

Lys Gly Leu Ala Asn Val Gln Cys Ser Asp Leu Leu Lys Lys Trp Leu
                245                 250                 255

Pro Gln Arg Cys Ala Thr Phe Ala Ser Lys Ile Gln Gly Gln Val Asp
            260                 265                 270

Lys Ile Lys Gly Ala Gly Gly Asp
        275                 280

<210> SEQ ID NO 13
<211> LENGTH: 1653
<212> TYPE: DNA
<213> ORGANISM: Homo sapiens
<220> FEATURE:
<221> NAME/KEY: CDS
<222> LOCATION: (1)..(1653)

<400> SEQUENCE: 13 tac aac ttc ttc cct cgc aag ccc aag tgg gac aag aac cag atc aca      48
Tyr Asn Phe Phe Pro Arg Lys Pro Lys Trp Asp Lys Asn Gln Ile Thr
1               5                   10                  15 tac agg atc att ggc tac aca cct gat ctg gac cca gag aca gtg gat      96
Tyr Arg Ile Ile Gly Tyr Thr Pro Asp Leu Asp Pro Glu Thr Val Asp
            20                  25                  30 gat gcc ttt gct cgt gcc ttc caa gtc tgg agc gat gtg acc cca ctg     144
Asp Ala Phe Ala Arg Ala Phe Gln Val Trp Ser Asp Val Thr Pro Leu
        35                  40                  45 cgg ttt tct cga atc cat gat gga gag gca gac atc atg atc aac ttt     192
Arg Phe Ser Arg Ile His Asp Gly Glu Ala Asp Ile Met Ile Asn Phe
    50                  55                  60 ggc cgc tgg gag cat ggc gat gga tac ccc ttt gac ggt aag gac gga     240
Gly Arg Trp Glu His Gly Asp Gly Tyr Pro Phe Asp Gly Lys Asp Gly
65                  70                  75                  80 ctc ctg gct cat gcc ttc gcc cca ggc act ggt gtt ggg gga gac tcc     288
Leu Leu Ala His Ala Phe Ala Pro Gly Thr Gly Val Gly Gly Asp Ser
                85                  90                  95 cat ttt gat gac gat gag cta tgg acc ttg gga gaa ggc caa gtg gtc     336
His Phe Asp Asp Asp Glu Leu Trp Thr Leu Gly Glu Gly Gln Val Val
            100                 105                 110 cgt gtg aag tat ggc aac gcc gat ggg gag tac tgc aag ttc ccc ttc     384
```

```
                Arg Val Lys Tyr Gly Asn Ala Asp Gly Glu Tyr Cys Lys Phe Pro Phe
                            115                 120                 125 ttg ttc aat ggc aag gag tac aac agc tgc act gat acc ggc cgc agc        432
Leu Phe Asn Gly Lys Glu Tyr Asn Ser Cys Thr Asp Thr Gly Arg Ser
        130                 135                 140 gat ggc ttc ctc tgg tgc tcc acc acc tac aac ttt gag aag gat ggc        480
Asp Gly Phe Leu Trp Cys Ser Thr Thr Tyr Asn Phe Glu Lys Asp Gly
145                 150                 155                 160 aag tac ggc ttc tgt ccc cat gaa gcc ctg ttc acc atg ggc ggc aac        528
Lys Tyr Gly Phe Cys Pro His Glu Ala Leu Phe Thr Met Gly Gly Asn
                165                 170                 175 gct gaa gga cag ccc tgc aag ttt cca ttc cgc ttc cag ggc aca tcc        576
Ala Glu Gly Gln Pro Cys Lys Phe Pro Phe Arg Phe Gln Gly Thr Ser
        180                 185                 190 tat gac agc tgc acc act gag ggc cgc acg gat ggc tac cgc tgg tgc        624
Tyr Asp Ser Cys Thr Thr Glu Gly Arg Thr Asp Gly Tyr Arg Trp Cys
                195                 200                 205 ggc acc act gag gac tac gac cgc gac aag aag tat ggc ttc tgc cct        672
Gly Thr Thr Glu Asp Tyr Asp Arg Asp Lys Lys Tyr Gly Phe Cys Pro
210                 215                 220 gag acc gcc atg tcc act gtt ggt ggg aac tca gaa ggt gcc ccc tgt        720
Glu Thr Ala Met Ser Thr Val Gly Gly Asn Ser Glu Gly Ala Pro Cys
225                 230                 235                 240 gtc ttc ccc ttc act ttc ctg ggc aac aaa tat gag agc tgc acc agc        768
Val Phe Pro Phe Thr Phe Leu Gly Asn Lys Tyr Glu Ser Cys Thr Ser
                245                 250                 255 gcc ggc cgc agt gac gga aag atg tgg tgt gcg acc aca gcc aac tac        816
Ala Gly Arg Ser Asp Gly Lys Met Trp Cys Ala Thr Thr Ala Asn Tyr
        260                 265                 270 gat gac gac cgc aag tgg ggc ttc tgc cct gac caa ggg tac agc ctg        864
Asp Asp Asp Arg Lys Trp Gly Phe Cys Pro Asp Gln Gly Tyr Ser Leu
                275                 280                 285 ttc ctc gtg gca gcc cac gag ttt ggc cac gcc atg ggg ctg gag cac        912
Phe Leu Val Ala Ala His Glu Phe Gly His Ala Met Gly Leu Glu His
290                 295                 300 tcc caa gac cct ggg gcc ctg atg gca ccc att tac acc tac acc aag        960
Ser Gln Asp Pro Gly Ala Leu Met Ala Pro Ile Tyr Thr Tyr Thr Lys
305                 310                 315                 320 aac ttc cgt ctg tcc cag gat gac atc aag ggc att cag gag ctc tat       1008
Asn Phe Arg Leu Ser Gln Asp Asp Ile Lys Gly Ile Gln Glu Leu Tyr
                325                 330                 335 ggg gcc tct cct gac att gac ctt ggc acc ggc ccc acc ccc aca ctg       1056
Gly Ala Ser Pro Asp Ile Asp Leu Gly Thr Gly Pro Thr Pro Thr Leu
        340                 345                 350 ggc cct gtc act cct gag atc tgc aaa cag gac att gta ttt gat ggc       1104
Gly Pro Val Thr Pro Glu Ile Cys Lys Gln Asp Ile Val Phe Asp Gly
                355                 360                 365 atc gct cag atc cgt ggt gag atc ttc ttc ttc aag gac cgg ttc att       1152
Ile Ala Gln Ile Arg Gly Glu Ile Phe Phe Phe Lys Asp Arg Phe Ile
370                 375                 380 tgg cgg act gtg acg cca cgt gac aag ccc atg ggg ccc ctg ctg gtg       1200
Trp Arg Thr Val Thr Pro Arg Asp Lys Pro Met Gly Pro Leu Leu Val
385                 390                 395                 400 gcc aca ttc tgg cct gag ctc ccg gaa aag att gat gcg gta tac gag       1248
Ala Thr Phe Trp Pro Glu Leu Pro Glu Lys Ile Asp Ala Val Tyr Glu
                405                 410                 415 gcc cca cag gag gag aag gct gtg ttc ttt gca ggg aat gaa tac tgg       1296
Ala Pro Gln Glu Glu Lys Ala Val Phe Phe Ala Gly Asn Glu Tyr Trp
        420                 425                 430
```

-continued

| | | |
|---|---|---|
| atc tac tca gcc agc acc ctg gag cga ggg tac ccc aag cca ctg acc<br>Ile Tyr Ser Ala Ser Thr Leu Glu Arg Gly Tyr Pro Lys Pro Leu Thr<br>435                          440                        445 | 1344 |
| agc ctg gga ctg ccc cct gat gtc cag cga gtg gat gcc gcc ttt aac<br>Ser Leu Gly Leu Pro Pro Asp Val Gln Arg Val Asp Ala Ala Phe Asn<br>450                          455                        460 | 1392 |
| tgg agc aaa aac aag aag aca tac atc ttt gct gga gac aaa ttc tgg<br>Trp Ser Lys Asn Lys Lys Thr Tyr Ile Phe Ala Gly Asp Lys Phe Trp<br>465                          470                        475                        480 | 1440 |
| aga tac aat gag gtg aag aag aaa atg gat cct ggc ttt ccc aag ctc<br>Arg Tyr Asn Glu Val Lys Lys Lys Met Asp Pro Gly Phe Pro Lys Leu<br>                        485                        490                        495 | 1488 |
| atc gca gat gcc tgg aat gcc atc ccc gat aac ctg gat gcc gtc gtg<br>Ile Ala Asp Ala Trp Asn Ala Ile Pro Asp Asn Leu Asp Ala Val Val<br>500                          505                        510 | 1536 |
| gac ctg cag ggc ggt cac agc tac ttc ttc aag ggt gcc tat tac<br>Asp Leu Gln Gly Gly His Ser Tyr Phe Phe Lys Gly Ala Tyr Tyr<br>                      515                        520                        525 | 1584 |
| ctg aag ctg gag aac caa agt ctg aag agc gtg aag ttt gga agc atc<br>Leu Lys Leu Glu Asn Gln Ser Leu Lys Ser Val Lys Phe Gly Ser Ile<br>530                          535                        540 | 1632 |
| aaa tcc gac tgg cta ggc tgc<br>Lys Ser Asp Trp Leu Gly Cys<br>545                          550 | 1653 |

<210> SEQ ID NO 14
<211> LENGTH: 551
<212> TYPE: PRT
<213> ORGANISM: Homo sapiens

<400> SEQUENCE: 14

Tyr Asn Phe Phe Pro Arg Lys Pro Lys Trp Asp Lys Asn Gln Ile Thr
1               5                   10                  15

Tyr Arg Ile Ile Gly Tyr Thr Pro Asp Leu Asp Pro Glu Thr Val Asp
            20                  25                  30

Asp Ala Phe Ala Arg Ala Phe Gln Val Trp Ser Asp Val Thr Pro Leu
        35                  40                  45

Arg Phe Ser Arg Ile His Asp Gly Glu Ala Asp Ile Met Ile Asn Phe
    50                  55                  60

Gly Arg Trp Glu His Gly Asp Gly Tyr Pro Phe Asp Gly Lys Asp Gly
65                  70                  75                  80

Leu Leu Ala His Ala Phe Ala Pro Gly Thr Gly Val Gly Gly Asp Ser
                85                  90                  95

His Phe Asp Asp Asp Glu Leu Trp Thr Leu Gly Glu Gly Gln Val Val
            100                 105                 110

Arg Val Lys Tyr Gly Asn Ala Asp Gly Glu Tyr Cys Lys Phe Pro Phe
        115                 120                 125

Leu Phe Asn Gly Lys Glu Tyr Asn Ser Cys Thr Asp Thr Gly Arg Ser
    130                 135                 140

Asp Gly Phe Leu Trp Cys Ser Thr Thr Tyr Asn Phe Glu Lys Asp Gly
145                 150                 155                 160

Lys Tyr Gly Phe Cys Pro His Glu Ala Leu Phe Thr Met Gly Gly Asn
                165                 170                 175

Ala Glu Gly Gln Pro Cys Lys Phe Pro Phe Arg Phe Gln Gly Thr Ser
            180                 185                 190

Tyr Asp Ser Cys Thr Thr Glu Gly Arg Thr Asp Gly Tyr Arg Trp Cys
        195                 200                 205

Gly Thr Thr Glu Asp Tyr Asp Arg Asp Lys Lys Tyr Gly Phe Cys Pro
    210                 215                 220

Glu Thr Ala Met Ser Thr Val Gly Gly Asn Ser Glu Gly Ala Pro Cys
225                 230                 235                 240

Val Phe Pro Phe Thr Phe Leu Gly Asn Lys Tyr Glu Ser Cys Thr Ser
                245                 250                 255

Ala Gly Arg Ser Asp Gly Lys Met Trp Cys Ala Thr Thr Ala Asn Tyr
            260                 265                 270

Asp Asp Asp Arg Lys Trp Gly Phe Cys Pro Asp Gln Gly Tyr Ser Leu
        275                 280                 285

Phe Leu Val Ala Ala His Glu Phe Gly His Ala Met Gly Leu Glu His
    290                 295                 300

Ser Gln Asp Pro Gly Ala Leu Met Ala Pro Ile Tyr Thr Tyr Thr Lys
305                 310                 315                 320

Asn Phe Arg Leu Ser Gln Asp Ile Lys Gly Ile Gln Glu Leu Tyr
                325                 330                 335

Gly Ala Ser Pro Asp Ile Asp Leu Gly Thr Gly Pro Thr Pro Thr Leu
            340                 345                 350

Gly Pro Val Thr Pro Glu Ile Cys Lys Gln Asp Ile Val Phe Asp Gly
        355                 360                 365

Ile Ala Gln Ile Arg Gly Glu Ile Phe Phe Lys Asp Arg Phe Ile
    370                 375                 380

Trp Arg Thr Val Thr Pro Arg Asp Lys Pro Met Gly Pro Leu Leu Val
385                 390                 395                 400

Ala Thr Phe Trp Pro Glu Leu Pro Glu Lys Ile Asp Ala Val Tyr Glu
                405                 410                 415

Ala Pro Gln Glu Glu Lys Ala Val Phe Phe Ala Gly Asn Glu Tyr Trp
            420                 425                 430

Ile Tyr Ser Ala Ser Thr Leu Glu Arg Gly Tyr Pro Lys Pro Leu Thr
        435                 440                 445

Ser Leu Gly Leu Pro Pro Asp Val Gln Arg Val Asp Ala Ala Phe Asn
    450                 455                 460

Trp Ser Lys Asn Lys Lys Thr Tyr Ile Phe Ala Gly Asp Lys Phe Trp
465                 470                 475                 480

Arg Tyr Asn Glu Val Lys Lys Met Asp Pro Gly Phe Pro Lys Leu
                485                 490                 495

Ile Ala Asp Ala Trp Asn Ala Ile Pro Asp Asn Leu Asp Ala Val Val
            500                 505                 510

Asp Leu Gln Gly Gly Gly His Ser Tyr Phe Phe Lys Gly Ala Tyr Tyr
        515                 520                 525

Leu Lys Leu Glu Asn Gln Ser Leu Lys Ser Val Lys Phe Gly Ser Ile
    530                 535                 540

Lys Ser Asp Trp Leu Gly Cys
545                 550

<210> SEQ ID NO 15
<211> LENGTH: 87
<212> TYPE: DNA
<213> ORGANISM: Homo sapiens
<220> FEATURE:
<221> NAME/KEY: CDS
<222> LOCATION: (1)..(87)

<400> SEQUENCE: 15 atg gag gcg cta atg gcc cgg ggc gcg ctc acg ggt ccc ctg agg gcg      48
Met Glu Ala Leu Met Ala Arg Gly Ala Leu Thr Gly Pro Leu Arg Ala

```
1               5                   10                  15 ctc tgt ctc ctg ggc tgc ctg ctg agc cac gcc gcc gcc                      87
Leu Cys Leu Leu Gly Cys Leu Leu Ser His Ala Ala Ala
        20                  25

<210> SEQ ID NO 16
<211> LENGTH: 29
<212> TYPE: PRT
<213> ORGANISM: Homo sapiens

<400> SEQUENCE: 16

Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala
            20                  25

<210> SEQ ID NO 17
<211> LENGTH: 1893
<212> TYPE: DNA
<213> ORGANISM: Homo sapiens
<220> FEATURE:
<221> NAME/KEY: CDS
<222> LOCATION: (1)..(1893)

<400> SEQUENCE: 17 gcg ccg tcg ccc atc atc aag ttc ccc ggc gat gtc gcc ccc aaa acg        48
Ala Pro Ser Pro Ile Ile Lys Phe Pro Gly Asp Val Ala Pro Lys Thr
1               5                   10                  15 gac aaa gag ttg gca gtg caa tac ctg aac acc ttc tat ggc tgc ccc        96
Asp Lys Glu Leu Ala Val Gln Tyr Leu Asn Thr Phe Tyr Gly Cys Pro
            20                  25                  30 aag gag agc tgc aac ctg ttt gtg ctg aag gac aca cta aag aag atg       144
Lys Glu Ser Cys Asn Leu Phe Val Leu Lys Asp Thr Leu Lys Lys Met
        35                  40                  45 cag aag ttc ttt gga ctg ccc cag aca ggt gat ctt gac cag aat acc       192
Gln Lys Phe Phe Gly Leu Pro Gln Thr Gly Asp Leu Asp Gln Asn Thr
    50                  55                  60 atc gag acc atg cgg aag cca cgc tgc ggc aac cca gat gtg gcc aac       240
Ile Glu Thr Met Arg Lys Pro Arg Cys Gly Asn Pro Asp Val Ala Asn
65                  70                  75                  80 tac aac ttc ttc cct cgc aag ccc aag tgg gac aag aac cag atc aca       288
Tyr Asn Phe Phe Pro Arg Lys Pro Lys Trp Asp Lys Asn Gln Ile Thr
                85                  90                  95 tac agg atc att ggc tac aca cct gat ctg gac cca gag aca gtg gat       336
Tyr Arg Ile Ile Gly Tyr Thr Pro Asp Leu Asp Pro Glu Thr Val Asp
            100                 105                 110 gat gcc ttt gct cgt gcc ttc caa gtc tgg agc gat gtg acc cca ctg       384
Asp Ala Phe Ala Arg Ala Phe Gln Val Trp Ser Asp Val Thr Pro Leu
        115                 120                 125 cgg ttt tct cga atc cat gat gga gag gca gac atc atg atc aac ttt       432
Arg Phe Ser Arg Ile His Asp Gly Glu Ala Asp Ile Met Ile Asn Phe
    130                 135                 140 ggc cgc tgg gag cat ggc gat gga tac ccc ttt gac ggt aag gac gga       480
Gly Arg Trp Glu His Gly Asp Gly Tyr Pro Phe Asp Gly Lys Asp Gly
145                 150                 155                 160 ctc ctg gct cat gcc ttc gcc cca ggc act ggt gtt ggg gga gac tcc       528
Leu Leu Ala His Ala Phe Ala Pro Gly Thr Gly Val Gly Gly Asp Ser
                165                 170                 175 cat ttt gat gac gat gag cta tgg acc ttg gga gaa ggc caa gtg gtc       576
His Phe Asp Asp Asp Glu Leu Trp Thr Leu Gly Glu Gly Gln Val Val
            180                 185                 190
```

```
cgt gtg aag tat ggc aac gcc gat ggg gag tac tgc aag ttc ccc ttc      624
Arg Val Lys Tyr Gly Asn Ala Asp Gly Glu Tyr Cys Lys Phe Pro Phe
    195                 200                 205 ttg ttc aat ggc aag gag tac aac agc tgc act gat acc ggc cgc agc      672
Leu Phe Asn Gly Lys Glu Tyr Asn Ser Cys Thr Asp Thr Gly Arg Ser
210                 215                 220 gat ggc ttc ctc tgg tgc tcc acc acc tac aac ttt gag aag gat ggc      720
Asp Gly Phe Leu Trp Cys Ser Thr Thr Tyr Asn Phe Glu Lys Asp Gly
225                 230                 235                 240 aag tac ggc ttc tgt ccc cat gaa gcc ctg ttc acc atg ggc ggc aac      768
Lys Tyr Gly Phe Cys Pro His Glu Ala Leu Phe Thr Met Gly Gly Asn
            245                 250                 255 gct gaa gga cag ccc tgc aag ttt cca ttc cgc ttc cag ggc aca tcc      816
Ala Glu Gly Gln Pro Cys Lys Phe Pro Phe Arg Phe Gln Gly Thr Ser
        260                 265                 270 tat gac agc tgc acc act gag ggc cgc acg gat ggc tac cgc tgg tgc      864
Tyr Asp Ser Cys Thr Thr Glu Gly Arg Thr Asp Gly Tyr Arg Trp Cys
    275                 280                 285 ggc acc act gag gac tac gac cgc gac aag aag tat ggc ttc tgc cct      912
Gly Thr Thr Glu Asp Tyr Asp Arg Asp Lys Lys Tyr Gly Phe Cys Pro
290                 295                 300 gag acc gcc atg tcc act gtt ggt ggg aac tca gaa ggt gcc ccc tgt      960
Glu Thr Ala Met Ser Thr Val Gly Gly Asn Ser Glu Gly Ala Pro Cys
305                 310                 315                 320 gtc ttc ccc ttc act ttc ctg ggc aac aaa tat gag agc tgc acc agc     1008
Val Phe Pro Phe Thr Phe Leu Gly Asn Lys Tyr Glu Ser Cys Thr Ser
            325                 330                 335 gcc ggc cgc agt gac gga aag atg tgg tgt gcg acc aca gcc aac tac     1056
Ala Gly Arg Ser Asp Gly Lys Met Trp Cys Ala Thr Thr Ala Asn Tyr
        340                 345                 350 gat gac gac cgc aag tgg ggc ttc tgc cct gac caa ggg tac agc ctg     1104
Asp Asp Asp Arg Lys Trp Gly Phe Cys Pro Asp Gln Gly Tyr Ser Leu
    355                 360                 365 ttc ctc gtg gca gcc cac gag ttt ggc cac gcc atg ggg ctg gag cac     1152
Phe Leu Val Ala Ala His Glu Phe Gly His Ala Met Gly Leu Glu His
370                 375                 380 tcc caa gac cct ggg gcc ctg atg gca ccc att tac acc tac acc aag     1200
Ser Gln Asp Pro Gly Ala Leu Met Ala Pro Ile Tyr Thr Tyr Thr Lys
385                 390                 395                 400 aac ttc cgt ctg tcc cag gat gac atc aag ggc att cag gag ctc tat     1248
Asn Phe Arg Leu Ser Gln Asp Asp Ile Lys Gly Ile Gln Glu Leu Tyr
            405                 410                 415 ggg gcc tct cct gac att gac ctt ggc acc ggc ccc acc ccc aca ctg     1296
Gly Ala Ser Pro Asp Ile Asp Leu Gly Thr Gly Pro Thr Pro Thr Leu
        420                 425                 430 ggc cct gtc act cct gag atc tgc aaa cag gac att gta ttt gat ggc     1344
Gly Pro Val Thr Pro Glu Ile Cys Lys Gln Asp Ile Val Phe Asp Gly
    435                 440                 445 atc gct cag atc cgt ggt gag atc ttc ttc ttc aag gac cgg ttc att     1392
Ile Ala Gln Ile Arg Gly Glu Ile Phe Phe Phe Lys Asp Arg Phe Ile
450                 455                 460 tgg cgg act gtg acg cca cgt gac aag ccc atg ggg ccc ctg ctg gtg     1440
Trp Arg Thr Val Thr Pro Arg Asp Lys Pro Met Gly Pro Leu Leu Val
465                 470                 475                 480 gcc aca ttc tgg cct gag ctc ccg gaa aag att gat gcg gta tac gag     1488
Ala Thr Phe Trp Pro Glu Leu Pro Glu Lys Ile Asp Ala Val Tyr Glu
            485                 490                 495 gcc cca cag gag gag aag gct gtg ttc ttt gca ggg aat gaa tac tgg     1536
Ala Pro Gln Glu Glu Lys Ala Val Phe Phe Ala Gly Asn Glu Tyr Trp
        500                 505                 510
```

```
atc tac tca gcc agc acc ctg gag cga ggg tac ccc aag cca ctg acc    1584
Ile Tyr Ser Ala Ser Thr Leu Glu Arg Gly Tyr Pro Lys Pro Leu Thr
            515                 520                 525 agc ctg gga ctg ccc cct gat gtc cag cga gtg gat gcc gcc ttt aac    1632
Ser Leu Gly Leu Pro Pro Asp Val Gln Arg Val Asp Ala Ala Phe Asn
530                 535                 540 tgg agc aaa aac aag aag aca tac atc ttt gct gga gac aaa ttc tgg    1680
Trp Ser Lys Asn Lys Lys Thr Tyr Ile Phe Ala Gly Asp Lys Phe Trp
545                 550                 555                 560 aga tac aat gag gtg aag aag aaa atg gat cct ggc ttt ccc aag ctc    1728
Arg Tyr Asn Glu Val Lys Lys Lys Met Asp Pro Gly Phe Pro Lys Leu
            565                 570                 575 atc gca gat gcc tgg aat gcc atc ccc gat aac ctg gat gcc gtc gtg    1776
Ile Ala Asp Ala Trp Asn Ala Ile Pro Asp Asn Leu Asp Ala Val Val
        580                 585                 590 gac ctg cag ggc ggc ggt cac agc tac ttc ttc aag ggt gcc tat tac    1824
Asp Leu Gln Gly Gly Gly His Ser Tyr Phe Phe Lys Gly Ala Tyr Tyr
    595                 600                 605 ctg aag ctg gag aac caa agt ctg aag agc gtg aag ttt gga agc atc    1872
Leu Lys Leu Glu Asn Gln Ser Leu Lys Ser Val Lys Phe Gly Ser Ile
610                 615                 620 aaa tcc gac tgg cta ggc tgc                                        1893
Lys Ser Asp Trp Leu Gly Cys
625                 630

<210> SEQ ID NO 18
<211> LENGTH: 631
<212> TYPE: PRT
<213> ORGANISM: Homo sapiens

<400> SEQUENCE: 18

Ala Pro Ser Pro Ile Ile Lys Phe Pro Gly Asp Val Ala Pro Lys Thr
1               5                   10                  15

Asp Lys Glu Leu Ala Val Gln Tyr Leu Asn Thr Phe Tyr Gly Cys Pro
            20                  25                  30

Lys Glu Ser Cys Asn Leu Phe Val Leu Lys Asp Thr Leu Lys Lys Met
        35                  40                  45

Gln Lys Phe Phe Gly Leu Pro Gln Thr Gly Asp Leu Asp Gln Asn Thr
    50                  55                  60

Ile Glu Thr Met Arg Lys Pro Arg Cys Gly Asn Pro Asp Val Ala Asn
65                  70                  75                  80

Tyr Asn Phe Phe Pro Arg Lys Pro Lys Trp Asp Lys Asn Gln Ile Thr
                85                  90                  95

Tyr Arg Ile Ile Gly Tyr Thr Pro Asp Leu Asp Pro Glu Thr Val Asp
            100                 105                 110

Asp Ala Phe Ala Arg Ala Phe Gln Val Trp Ser Asp Val Thr Pro Leu
        115                 120                 125

Arg Phe Ser Arg Ile His Asp Gly Glu Ala Asp Ile Met Ile Asn Phe
    130                 135                 140

Gly Arg Trp Glu His Gly Asp Gly Tyr Pro Phe Asp Gly Lys Asp Gly
145                 150                 155                 160

Leu Leu Ala His Ala Phe Ala Pro Gly Thr Gly Val Gly Gly Asp Ser
                165                 170                 175

His Phe Asp Asp Asp Glu Leu Trp Thr Leu Gly Glu Gly Gln Val Val
            180                 185                 190

Arg Val Lys Tyr Gly Asn Ala Asp Gly Glu Tyr Cys Lys Phe Pro Phe
        195                 200                 205
```

```
Leu Phe Asn Gly Lys Glu Tyr Asn Ser Cys Thr Asp Thr Gly Arg Ser
210                 215                 220
Asp Gly Phe Leu Trp Cys Ser Thr Thr Tyr Asn Phe Glu Lys Asp Gly
225                 230                 235                 240
Lys Tyr Gly Phe Cys Pro His Glu Ala Leu Phe Thr Met Gly Gly Asn
                245                 250                 255
Ala Glu Gly Gln Pro Cys Lys Phe Pro Phe Arg Phe Gln Gly Thr Ser
                260                 265                 270
Tyr Asp Ser Cys Thr Thr Glu Gly Arg Thr Asp Gly Tyr Arg Trp Cys
            275                 280                 285
Gly Thr Thr Glu Asp Tyr Asp Arg Asp Lys Lys Tyr Gly Phe Cys Pro
290                 295                 300
Glu Thr Ala Met Ser Thr Val Gly Gly Asn Ser Glu Gly Ala Pro Cys
305                 310                 315                 320
Val Phe Pro Phe Thr Phe Leu Gly Asn Lys Tyr Glu Ser Cys Thr Ser
                325                 330                 335
Ala Gly Arg Ser Asp Gly Lys Met Trp Cys Ala Thr Thr Ala Asn Tyr
                340                 345                 350
Asp Asp Asp Arg Lys Trp Gly Phe Cys Pro Asp Gln Gly Tyr Ser Leu
            355                 360                 365
Phe Leu Val Ala Ala His Glu Phe Gly His Ala Met Gly Leu Glu His
370                 375                 380
Ser Gln Asp Pro Gly Ala Leu Met Ala Pro Ile Tyr Thr Tyr Thr Lys
385                 390                 395                 400
Asn Phe Arg Leu Ser Gln Asp Asp Ile Lys Gly Ile Gln Glu Leu Tyr
                405                 410                 415
Gly Ala Ser Pro Asp Ile Asp Leu Gly Thr Gly Pro Thr Pro Thr Leu
                420                 425                 430
Gly Pro Val Thr Pro Glu Ile Cys Lys Gln Asp Ile Val Phe Asp Gly
            435                 440                 445
Ile Ala Gln Ile Arg Gly Glu Ile Phe Phe Phe Lys Asp Arg Phe Ile
450                 455                 460
Trp Arg Thr Val Thr Pro Arg Asp Lys Pro Met Gly Pro Leu Leu Val
465                 470                 475                 480
Ala Thr Phe Trp Pro Glu Leu Pro Glu Lys Ile Asp Ala Val Tyr Glu
                485                 490                 495
Ala Pro Gln Glu Glu Lys Ala Val Phe Phe Ala Gly Asn Glu Tyr Trp
                500                 505                 510
Ile Tyr Ser Ala Ser Thr Leu Glu Arg Gly Tyr Pro Lys Pro Leu Thr
            515                 520                 525
Ser Leu Gly Leu Pro Pro Asp Val Gln Arg Val Asp Ala Ala Phe Asn
530                 535                 540
Trp Ser Lys Asn Lys Lys Thr Tyr Ile Phe Ala Gly Asp Lys Phe Trp
545                 550                 555                 560
Arg Tyr Asn Glu Val Lys Lys Met Asp Pro Gly Phe Pro Lys Leu
                565                 570                 575
Ile Ala Asp Ala Trp Asn Ala Ile Pro Asp Asn Leu Asp Ala Val Val
            580                 585                 590
Asp Leu Gln Gly Gly Gly His Ser Tyr Phe Phe Lys Gly Ala Tyr Tyr
            595                 600                 605
Leu Lys Leu Glu Asn Gln Ser Leu Lys Ser Val Lys Phe Gly Ser Ile
610                 615                 620
```

```
Lys Ser Asp Trp Leu Gly Cys
625                 630

<210> SEQ ID NO 19
<211> LENGTH: 2490
<212> TYPE: DNA
<213> ORGANISM: Artificial
<220> FEATURE:
<223> OTHER INFORMATION: fusion protein
<220> FEATURE:
<221> NAME/KEY: CDS
<222> LOCATION: (1)..(2490)

<400> SEQUENCE: 19 atg gag gcg cta atg gcc cgg ggc gcg ctc acg ggt ccc ctg agg gcg      48
Met Glu Ala Leu Met Ala Arg Gly Ala Leu Thr Gly Pro Leu Arg Ala
1               5                   10                  15 ctc tgt ctc ctg ggc tgc ctg ctg agc cac gcc gcc gcc gcg ccg tcg      96
Leu Cys Leu Leu Gly Cys Leu Leu Ser His Ala Ala Ala Ala Pro Ser
                20                  25                  30 ccc atc atc aag ttc ccc ggc gat gtc gcc ccc aaa acg gac aaa gag     144
Pro Ile Ile Lys Phe Pro Gly Asp Val Ala Pro Lys Thr Asp Lys Glu
            35                  40                  45 ttg gca gtg caa tac ctg aac acc ttc tat ggc tgc ccc aag gag agc     192
Leu Ala Val Gln Tyr Leu Asn Thr Phe Tyr Gly Cys Pro Lys Glu Ser
        50                  55                  60 tgc aac ctg ttt gtg ctg aag gac aca cta aag aag atg cag aag ttc     240
Cys Asn Leu Phe Val Leu Lys Asp Thr Leu Lys Lys Met Gln Lys Phe
65                  70                  75                  80 ttt gga ctg ccc cag aca ggt gat ctt gac cag aat acc atc gag acc     288
Phe Gly Leu Pro Gln Thr Gly Asp Leu Asp Gln Asn Thr Ile Glu Thr
                85                  90                  95 atg cgg aag cca cgc tgc ggc aac cca gat gtg gcc aac tac aac ttc     336
Met Arg Lys Pro Arg Cys Gly Asn Pro Asp Val Ala Asn Tyr Asn Phe
            100                 105                 110 ttc cct cgc aag ccc aag tgg gac aag aac cag atc aca tac agg atc     384
Phe Pro Arg Lys Pro Lys Trp Asp Lys Asn Gln Ile Thr Tyr Arg Ile
        115                 120                 125 att ggc tac aca cct gat ctg gac cca gag aca gtg gat gat gcc ttt     432
Ile Gly Tyr Thr Pro Asp Leu Asp Pro Glu Thr Val Asp Asp Ala Phe
    130                 135                 140 gct cgt gcc ttc caa gtc tgg agc gat gtg acc cca ctg cgg ttt tct     480
Ala Arg Ala Phe Gln Val Trp Ser Asp Val Thr Pro Leu Arg Phe Ser
145                 150                 155                 160 cga atc cat gat gga gag gca gac atc atg atc aac ttt ggc cgc tgg     528
Arg Ile His Asp Gly Glu Ala Asp Ile Met Ile Asn Phe Gly Arg Trp
                165                 170                 175 gag cat ggc gat gga tac ccc ttt gac ggt aag gac gga ctc ctg gct     576
Glu His Gly Asp Gly Tyr Pro Phe Asp Gly Lys Asp Gly Leu Leu Ala
            180                 185                 190 cat gcc ttc gcc cca ggc act ggt gtt ggg gga gac tcc cat ttt gat     624
His Ala Phe Ala Pro Gly Thr Gly Val Gly Gly Asp Ser His Phe Asp
        195                 200                 205 gac gat gag cta tgg acc ttg gga gaa ggc caa gtg gtc cgt gtg aag     672
Asp Asp Glu Leu Trp Thr Leu Gly Glu Gly Gln Val Val Arg Val Lys
    210                 215                 220 tat ggc aac gcc gat ggg gag tac tgc aag ttc ccc ttc ttg ttc aat     720
Tyr Gly Asn Ala Asp Gly Glu Tyr Cys Lys Phe Pro Phe Leu Phe Asn
225                 230                 235                 240 ggc aag gag tac aac agc tgc act gat acc ggc cgc agc gat ggc ttc     768
Gly Lys Glu Tyr Asn Ser Cys Thr Asp Thr Gly Arg Ser Asp Gly Phe
                245                 250                 255
```

| | | |
|---|---|---|
| ctc tgg tgc tcc acc acc tac aac ttt gag aag gat ggc aag tac ggc<br>Leu Trp Cys Ser Thr Thr Tyr Asn Phe Glu Lys Asp Gly Lys Tyr Gly<br>260 265 270 | | 816 |
| ttc tgt ccc cat gaa gcc ctg ttc acc atg ggc ggc aac gct gaa gga<br>Phe Cys Pro His Glu Ala Leu Phe Thr Met Gly Gly Asn Ala Glu Gly<br>275 280 285 | | 864 |
| cag ccc tgc aag ttt cca ttc cgc ttc cag ggc aca tcc tat gac agc<br>Gln Pro Cys Lys Phe Pro Phe Arg Phe Gln Gly Thr Ser Tyr Asp Ser<br>290 295 300 | | 912 |
| tgc acc act gag ggc cgc acg gat ggc tac cgc tgg tgc ggc acc act<br>Cys Thr Thr Glu Gly Arg Thr Asp Gly Tyr Arg Trp Cys Gly Thr Thr<br>305 310 315 320 | | 960 |
| gag gac tac gac cgc gac aag aag tat ggc ttc tgc cct gag acc gcc<br>Glu Asp Tyr Asp Arg Asp Lys Lys Tyr Gly Phe Cys Pro Glu Thr Ala<br>325 330 335 | | 1008 |
| atg tcc act gtt ggt ggg aac tca gaa ggt gcc ccc tgt gtc ttc ccc<br>Met Ser Thr Val Gly Gly Asn Ser Glu Gly Ala Pro Cys Val Phe Pro<br>340 345 350 | | 1056 |
| ttc act ttc ctg ggc aac aaa tat gag agc tgc acc agc gcc ggc cgc<br>Phe Thr Phe Leu Gly Asn Lys Tyr Glu Ser Cys Thr Ser Ala Gly Arg<br>355 360 365 | | 1104 |
| agt gac gga aag atg tgg tgt gcg acc aca gcc aac tac gat gac gac<br>Ser Asp Gly Lys Met Trp Cys Ala Thr Thr Ala Asn Tyr Asp Asp Asp<br>370 375 380 | | 1152 |
| cgc aag tgg ggc ttc tgc cct gac caa ggg tac agc ctg ttc ctc gtg<br>Arg Lys Trp Gly Phe Cys Pro Asp Gln Gly Tyr Ser Leu Phe Leu Val<br>385 390 395 400 | | 1200 |
| gca gcc cac gag ttt ggc cac gcc atg ggg ctg gag cac tcc caa gac<br>Ala Ala His Glu Phe Gly His Ala Met Gly Leu Glu His Ser Gln Asp<br>405 410 415 | | 1248 |
| cct ggg gcc ctg atg gca ccc att tac acc tac acc aag aac ttc cgt<br>Pro Gly Ala Leu Met Ala Pro Ile Tyr Thr Tyr Thr Lys Asn Phe Arg<br>420 425 430 | | 1296 |
| ctg tcc cag gat gac atc aag ggc att cag gag ctc tat ggg gcc tct<br>Leu Ser Gln Asp Asp Ile Lys Gly Ile Gln Glu Leu Tyr Gly Ala Ser<br>435 440 445 | | 1344 |
| cct gac att gac ctt ggc acc ggc ccc acc ccc aca ctg ggc cct gtc<br>Pro Asp Ile Asp Leu Gly Thr Gly Pro Thr Pro Thr Leu Gly Pro Val<br>450 455 460 | | 1392 |
| act cct gag atc tgc aaa cag gac att gta ttt gat ggc atc gct cag<br>Thr Pro Glu Ile Cys Lys Gln Asp Ile Val Phe Asp Gly Ile Ala Gln<br>465 470 475 480 | | 1440 |
| atc cgt ggt gag atc ttc ttc ttc aag gac cgg ttc att tgg cgg act<br>Ile Arg Gly Glu Ile Phe Phe Phe Lys Asp Arg Phe Ile Trp Arg Thr<br>485 490 495 | | 1488 |
| gtg acg cca cgt gac aag ccc atg ggg ccc ctg ctg gtg gcc aca ttc<br>Val Thr Pro Arg Asp Lys Pro Met Gly Pro Leu Leu Val Ala Thr Phe<br>500 505 510 | | 1536 |
| tgg cct gag ctc ccg gaa aag att gat gcg gta tac gag gcc cca cag<br>Trp Pro Glu Leu Pro Glu Lys Ile Asp Ala Val Tyr Glu Ala Pro Gln<br>515 520 525 | | 1584 |
| gag gag aag gct gtg ttc ttt gca ggg aat gaa tac tgg atc tac tca<br>Glu Glu Lys Ala Val Phe Phe Ala Gly Asn Glu Tyr Trp Ile Tyr Ser<br>530 535 540 | | 1632 |
| gcc agc acc ctg gag cga ggg tac ccc aag cca ctg acc agc ctg gga<br>Ala Ser Thr Leu Glu Arg Gly Tyr Pro Lys Pro Leu Thr Ser Leu Gly<br>545 550 555 560 | | 1680 |
| ctg ccc cct gat gtc cag cga gtg gat gcc gcc ttt aac tgg agc aaa<br>Leu Pro Pro Asp Val Gln Arg Val Asp Ala Ala Phe Asn Trp Ser Lys | | 1728 |

```
aac aag aag aca tac atc ttt gct gga gac aaa ttc tgg aga tac aat       1776
Asn Lys Lys Thr Tyr Ile Phe Ala Gly Asp Lys Phe Trp Arg Tyr Asn
            580                 585                 590 gag gtg aag aag aaa atg gat cct ggc ttt ccc aag ctc atc gca gat       1824
Glu Val Lys Lys Lys Met Asp Pro Gly Phe Pro Lys Leu Ile Ala Asp
        595                 600                 605 gcc tgg aat gcc atc ccc gat aac ctg gat gcc gtc gtg gac ctg cag       1872
Ala Trp Asn Ala Ile Pro Asp Asn Leu Asp Ala Val Val Asp Leu Gln
610                 615                 620 ggc ggc ggt cac agc tac ttc ttc aag ggt gcc tat tac ctg aag ctg       1920
Gly Gly Gly His Ser Tyr Phe Phe Lys Gly Ala Tyr Tyr Leu Lys Leu
625                 630                 635                 640 gag aac caa agt ctg aag agc gtg aag ttt gga agc atc aaa tcc gac       1968
Glu Asn Gln Ser Leu Lys Ser Val Lys Phe Gly Ser Ile Lys Ser Asp
            645                 650                 655 tgg cta ggc tgc gaa ttc aag ccc acc gag aac aac gaa gac ttc aac       2016
Trp Leu Gly Cys Glu Phe Lys Pro Thr Glu Asn Asn Glu Asp Phe Asn
        660                 665                 670 atc gtg gcc gtg gcc agc aac ttc gcg acc acg gat ctc gat gct gac       2064
Ile Val Ala Val Ala Ser Asn Phe Ala Thr Thr Asp Leu Asp Ala Asp
675                 680                 685 cgc ggg aag ttg ccc ggc aag aag ctg ccg ctg gag gtg ctc aaa gag       2112
Arg Gly Lys Leu Pro Gly Lys Lys Leu Pro Leu Glu Val Leu Lys Glu
690                 695                 700 atg gaa gcc aat gcc cgg aaa gct ggc tgc acc agg ggc tgt ctg atc       2160
Met Glu Ala Asn Ala Arg Lys Ala Gly Cys Thr Arg Gly Cys Leu Ile
705                 710                 715                 720 tgc ctg tcc cac atc aag tgc acg ccc aag atg aag aag ttc atc cca       2208
Cys Leu Ser His Ile Lys Cys Thr Pro Lys Met Lys Lys Phe Ile Pro
            725                 730                 735 gga cgc tgc cac acc tac gaa ggc gac aaa gag tcc gca cag ggc ggc       2256
Gly Arg Cys His Thr Tyr Glu Gly Asp Lys Glu Ser Ala Gln Gly Gly
        740                 745                 750 ata ggc gag gcg atc gtc gac att cct gag att cct ggg ttc aag gac       2304
Ile Gly Glu Ala Ile Val Asp Ile Pro Glu Ile Pro Gly Phe Lys Asp
755                 760                 765 ttg gag ccc atg gag cag ttc atc gca cag gtc gat ctg tgt gtg gac       2352
Leu Glu Pro Met Glu Gln Phe Ile Ala Gln Val Asp Leu Cys Val Asp
770                 775                 780 tgc aca act ggc tgc ctc aaa ggg ctt gcc aac gtg cag tgt tct gac       2400
Cys Thr Thr Gly Cys Leu Lys Gly Leu Ala Asn Val Gln Cys Ser Asp
785                 790                 795                 800 ctg ctc aag aag tgg ctg ccg caa cgc tgt gcg acc ttt gcc agc aag       2448
Leu Leu Lys Lys Trp Leu Pro Gln Arg Cys Ala Thr Phe Ala Ser Lys
            805                 810                 815 atc cag ggc cag gtg gac aag atc aag ggg gcc ggt ggt gac                2490
Ile Gln Gly Gln Val Asp Lys Ile Lys Gly Ala Gly Gly Asp
        820                 825                 830

<210> SEQ ID NO 20
<211> LENGTH: 830
<212> TYPE: PRT
<213> ORGANISM: Artificial
<220> FEATURE:
<223> OTHER INFORMATION: Synthetic Construct

<400> SEQUENCE: 20

Met Glu Ala Leu Met Ala Arg Gly Ala Leu Thr Gly Pro Leu Arg Ala
1               5                   10                  15
```

```
Leu Cys Leu Leu Gly Cys Leu Leu Ser His Ala Ala Ala Pro Ser
         20                  25                  30

Pro Ile Ile Lys Phe Pro Gly Asp Val Ala Pro Lys Thr Asp Lys Glu
             35                  40                  45

Leu Ala Val Gln Tyr Leu Asn Thr Phe Tyr Gly Cys Pro Lys Glu Ser
         50                  55                  60

Cys Asn Leu Phe Val Leu Lys Asp Thr Leu Lys Lys Met Gln Lys Phe
65                   70                  75                  80

Phe Gly Leu Pro Gln Thr Gly Asp Leu Asp Gln Asn Thr Ile Glu Thr
                 85                  90                  95

Met Arg Lys Pro Arg Cys Gly Asn Pro Asp Val Ala Asn Tyr Asn Phe
                100                 105                 110

Phe Pro Arg Lys Pro Lys Trp Asp Lys Asn Gln Ile Thr Tyr Arg Ile
             115                 120                 125

Ile Gly Tyr Thr Pro Asp Leu Asp Pro Glu Thr Val Asp Asp Ala Phe
         130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
                165                 170                 175

Glu His Gly Asp Gly Tyr Pro Phe Asp Gly Lys Asp Gly Leu Leu Ala
                180                 185                 190

His Ala Phe Ala Pro Gly Thr Gly Val Gly Gly Asp Ser His Phe Asp
             195                 200                 205

Asp Asp Glu Leu Trp Thr Leu Gly Glu Gly Gln Val Val Arg Val Lys
210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
                245                 250                 255

Leu Trp Cys Ser Thr Thr Tyr Asn Phe Glu Lys Asp Gly Lys Tyr Gly
             260                 265                 270

Phe Cys Pro His Glu Ala Leu Phe Thr Met Gly Gly Asn Ala Glu Gly
         275                 280                 285

Gln Pro Cys Lys Phe Pro Phe Arg Phe Gln Gly Thr Ser Tyr Asp Ser
290                 295                 300

Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
                325                 330                 335

Met Ser Thr Val Gly Gly Asn Ser Glu Gly Ala Pro Cys Val Phe Pro
             340                 345                 350

Phe Thr Phe Leu Gly Asn Lys Tyr Glu Ser Cys Thr Ser Ala Gly Arg
         355                 360                 365

Ser Asp Gly Lys Met Trp Cys Ala Thr Thr Ala Asn Tyr Asp Asp Asp
     370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Thr Lys Asn Phe Arg
             420                 425                 430

Leu Ser Gln Asp Asp Ile Lys Gly Ile Gln Glu Leu Tyr Gly Ala Ser
```

-continued

```
                435                 440                 445
Pro Asp Ile Asp Leu Gly Thr Gly Pro Thr Pro Thr Leu Gly Pro Val
450                 455                 460

Thr Pro Glu Ile Cys Lys Gln Asp Ile Val Phe Asp Gly Ile Ala Gln
465                 470                 475                 480

Ile Arg Gly Glu Ile Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
        515                 520                 525

Glu Glu Lys Ala Val Phe Phe Ala Gly Asn Glu Tyr Trp Ile Tyr Ser
530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
                565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
        595                 600                 605

Ala Trp Asn Ala Ile Pro Asp Asn Leu Asp Ala Val Val Asp Leu Gln
610                 615                 620

Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys Glu Phe Lys Pro Thr Glu Asn Asn Glu Asp Phe Asn
            660                 665                 670

Ile Val Ala Val Ala Ser Asn Phe Ala Thr Thr Asp Leu Asp Ala Asp
        675                 680                 685

Arg Gly Lys Leu Pro Gly Lys Lys Leu Pro Leu Glu Val Leu Lys Glu
690                 695                 700

Met Glu Ala Asn Ala Arg Lys Ala Gly Cys Thr Arg Gly Cys Leu Ile
705                 710                 715                 720

Cys Leu Ser His Ile Lys Cys Thr Pro Lys Met Lys Lys Phe Ile Pro
                725                 730                 735

Gly Arg Cys His Thr Tyr Glu Gly Asp Lys Glu Ser Ala Gln Gly Gly
            740                 745                 750

Ile Gly Glu Ala Ile Val Asp Ile Pro Glu Ile Pro Gly Phe Lys Asp
        755                 760                 765

Leu Glu Pro Met Glu Gln Phe Ile Ala Gln Val Asp Leu Cys Val Asp
770                 775                 780

Cys Thr Thr Gly Cys Leu Lys Gly Leu Ala Asn Val Gln Cys Ser Asp
785                 790                 795                 800

Leu Leu Lys Lys Trp Leu Pro Gln Arg Cys Ala Thr Phe Ala Ser Lys
                805                 810                 815

Ile Gln Gly Gln Val Asp Lys Ile Lys Gly Ala Gly Gly Asp
            820                 825                 830

<210> SEQ ID NO 21
<211> LENGTH: 36
<212> TYPE: DNA
<213> ORGANISM: Artificial
```

```
<220> FEATURE:
<223> OTHER INFORMATION: primer

<400> SEQUENCE: 21
ctcggatcca gccaccatgg ccctgtggat gcgcct                                36

<210> SEQ ID NO 22
<211> LENGTH: 30
<212> TYPE: DNA
<213> ORGANISM: Artificial
<220> FEATURE:
<223> OTHER INFORMATION: primer

<400> SEQUENCE: 22
cttgaattcg ttgcagtagt tctccagctg                                       30

<210> SEQ ID NO 23
<211> LENGTH: 35
<212> TYPE: DNA
<213> ORGANISM: Artificial
<220> FEATURE:
<223> OTHER INFORMATION: primer

<400> SEQUENCE: 23
ggcaagctta gccaccatgg aggcgctaat ggccc                                 35

<210> SEQ ID NO 24
<211> LENGTH: 28
<212> TYPE: DNA
<213> ORGANISM: Artificial
<220> FEATURE:
<223> OTHER INFORMATION: primer

<400> SEQUENCE: 24
ggcgaattcg cagcctagcc agtcggat                                         28
```